US 7,452,541 B2
Nov. 18, 2008

(12) United States Patent
Bachmann et al.

(54) HAPTEN-CARRIER CONJUGATES AND USES THEREOF

(75) Inventors: Martin F. Bachmann, Seuzach (CH); Patrik Maurer, Winterthur (CH)

(73) Assignee: Cytos Biotechnology AG, Zurich-Schlieren (CH)

(*) Notice: Subject to any disclaimer, the term of this patent is extended or adjusted under 35 U.S.C. 154(b) by 366 days.

This patent is subject to a terminal disclaimer.

(21) Appl. No.: 11/125,402

(22) Filed: May 10, 2005

(65) Prior Publication Data

US 2005/0281845 A1    Dec. 22, 2005

Related U.S. Application Data

(62) Division of application No. 10/622,064, filed on Jul. 18, 2003, now Pat. No. 6,932,971.

(60) Provisional application No. 60/396,575, filed on Jul. 18, 2002.

(51) Int. Cl.
*A61K 39/385* (2006.01)
*C07D 401/04* (2006.01)

(52) U.S. Cl. .............. 424/193.1; 424/194.1; 424/196.11; 514/343; 546/279.4

(58) Field of Classification Search ............. None
See application file for complete search history.

(56) References Cited

U.S. PATENT DOCUMENTS

| | | | |
|---|---|---|---|
| 3,819,706 A | 6/1974 | Mehta | |
| 3,885,046 A | 5/1975 | Mehta | |
| 3,888,866 A | 6/1975 | Leute et al. | |
| 4,123,431 A | 10/1978 | Soffer et al. | |
| 4,197,237 A | 4/1980 | Leute et al. | |
| 4,722,840 A | 2/1988 | Valenzuela et al. | |
| 4,788,189 A | 11/1988 | Glazer | |
| 4,918,166 A | 4/1990 | Kingsman et al. | |
| 5,071,651 A | 12/1991 | Sabara et al. | |
| 5,143,726 A | 9/1992 | Thornton et al. | |
| 5,256,409 A | 10/1993 | Blincko | |
| 5,334,394 A | 8/1994 | Kossovsky et al. | |
| 5,374,426 A | 12/1994 | Sabara et al. | |
| 5,580,859 A | 12/1996 | Felgner et al. | |
| 5,698,424 A | 12/1997 | Mastico et al. | |
| 5,739,026 A | 4/1998 | Garoff et al. | |
| 5,766,602 A | 6/1998 | Xiong et al. | |
| 5,770,380 A | 6/1998 | Hamilton et al. | |
| 5,789,245 A | 8/1998 | Dubensky, Jr. et al. | |
| 5,792,462 A | 8/1998 | Johnston et al. | |
| 5,814,482 A | 9/1998 | Dubensky, Jr. et al. | |
| 5,871,747 A | 2/1999 | Gengoux-Sedlik et al. | |
| 5,876,727 A | 3/1999 | Swain et al. | |
| 5,928,647 A | 7/1999 | Rock | |
| 5,939,598 A | 8/1999 | Kucherlapati et al. | |
| 6,004,763 A | 12/1999 | Gengoux et al. | |
| 6,054,312 A | 4/2000 | Larocca et al. | |
| 6,231,864 B1 | 5/2001 | Birkett | |
| 6,232,082 B1 | 5/2001 | Ennifar et al. | |
| 6,380,364 B1 | 4/2002 | Mueller et al. | |
| 6,699,474 B1 | 3/2004 | Cerny | |
| 6,719,978 B2 | 4/2004 | Schiller et al. | |
| 6,932,971 B2 * | 8/2005 | Bachmann et al. ....... 424/193.1 |
| 2002/0064529 A1 | 5/2002 | Bohannon | |
| 2002/0064533 A1 | 5/2002 | Murray | |
| 2002/0081295 A1 | 6/2002 | Schiller et al. | |
| 2003/0157479 A1 | 8/2003 | Bachmann et al. | |
| 2003/0175290 A1 | 9/2003 | Renner et al. | |
| 2003/0175711 A1 | 9/2003 | Renner et al. | |
| 2003/0219459 A1 | 11/2003 | Bachmann et al. | |
| 2004/0033211 A1 | 2/2004 | Bachmann et al. | |
| 2004/0076611 A1 | 4/2004 | Bachmann et al. | |

(Continued)

FOREIGN PATENT DOCUMENTS

EP    0 259 149 B1    12/1993

(Continued)

OTHER PUBLICATIONS

Pentel, et al. A Nicotine Conjugate Vaccine Reduces Nicotine Distribution to Brain and Attenuates Its Behavioral and Cardiovascular Effects in Rats. Pharmacol. Biochem Behavior 2000; 65(1):191-198.*

(Continued)

*Primary Examiner*—Mary R. Mosher
*Assistant Examiner*—Stuart W. Snyder
(74) *Attorney, Agent, or Firm*—Sterne, Kessler, Goldstein & Fox P.L.L.C.

(57) ABSTRACT

The present invention provides compositions comprising a conjugate of a hapten with a carrier in an ordered and repetitive array, and methods of making such compositions. The conjugates and compositions of the invention may comprise a variety of haptens, including hormones, toxins and drugs, especially drugs of addiction such as nicotine. Compositions and conjugates of the invention are useful for inducing immune responses against haptens, which can use useful in a variety of therapeutic, prophylactic and diagnostic regimens. In certain embodiments, immune responses generated using the conjugates, compositions and methods of the present invention are useful to prevent or treat addiction to drugs of abuse and the resultant diseases associated with drug addiction.

45 Claims, 10 Drawing Sheets

U.S. PATENT DOCUMENTS

| | | | |
|---|---|---|---|
| 2004/0076645 A1 | 4/2004 | Bachmann et al. | |
| 2004/0136962 A1 | 7/2004 | Renner et al. | |
| 2004/0141984 A1 | 7/2004 | Bachmann et al. | |

FOREIGN PATENT DOCUMENTS

| | | |
|---|---|---|
| EP | 0 576 357 B1 | 12/1993 |
| EP | 0 385 610 B1 | 3/1994 |
| EP | 0 465 081 B1 | 4/1994 |
| EP | 0 283 505 B1 | 7/1994 |
| EP | 0 425 082 B1 | 4/1995 |
| EP | 0 656 354 B1 | 6/1995 |
| FR | 2695563 | 3/1994 |
| WO | WO 92/03163 A1 | 3/1992 |
| WO | WO 92/11291 A1 | 7/1992 |
| WO | WO 92/13081 A | 8/1992 |
| WO | WO 92/21333 A2 | 12/1992 |
| WO | WO 94/06472 A1 | 3/1994 |
| WO | WO 94/15585 A1 | 7/1994 |
| WO | WO 94/28888 A1 | 12/1994 |
| WO | WO 96/02248 A1 | 2/1996 |
| WO | WO 96/05293 A1 | 2/1996 |
| WO | WO 96/30049 A2 | 10/1996 |
| WO | WO 96/30049 A3 | 10/1996 |
| WO | WO 96/30523 A2 | 10/1996 |
| WO | WO 97/31948 A1 | 9/1997 |
| WO | WO 98/14216 A2 | 4/1998 |
| WO | WO 98/15631 A1 | 4/1998 |
| WO | WO 99/07839 A2 | 2/1999 |
| WO | WO 99/07839 A3 | 2/1999 |
| WO | WO 99/17803 A1 | 4/1999 |
| WO | WO 99/28478 A1 | 6/1999 |
| WO | WO 99/40934 A | 8/1999 |
| WO | WO 99/40934 A1 | 8/1999 |
| WO | WO 99/57289 A2 | 11/1999 |
| WO | WO 99/57289 A3 | 11/1999 |
| WO | WO 99/61054 A1 | 12/1999 |
| WO | WO 99/67293 A1 | 12/1999 |
| WO | WO 00/00462 A1 | 1/2000 |
| WO | WO 00/23955 A1 | 4/2000 |
| WO | WO 00/32227 A2 | 6/2000 |
| WO | WO 00/32227 A3 | 6/2000 |
| WO | WO 00/50461 A1 | 8/2000 |
| WO | WO 00/59928 A1 | 10/2000 |
| WO | WO 01/12176 A2 | 2/2001 |
| WO | WO 01/12176 A3 | 2/2001 |
| WO | WO 01/62284 A2 | 8/2001 |
| WO | WO 01/77158 A1 | 10/2001 |
| WO | WO 01/85208 A2 | 11/2001 |
| WO | WO 01/85208 A3 | 11/2001 |
| WO | WO 02/14478 A2 | 2/2002 |
| WO | WO 02/056905 A2 | 7/2002 |
| WO | WO 02/058635 A2 | 8/2002 |
| WO | WO 02/058635 A3 | 8/2002 |
| WO | WO 03/040105 A1 | 5/2003 |

OTHER PUBLICATIONS

Chackerian, et al. Conjugation of a self-antigen to papillomavirus-like particles allows for efficient induction of protective anutoantibodies. J Clin Invest. 2001; 108(3):415-423.*

Abraham, J.M., et al., "An invertible element of DNA controls phase variation of type 1 fimbriae of *Escherichia coli*," *Proc. Natl. Acad. Sci. USA 82*:5724-5727, National Academy Press (1985).

Abraham, S.N., et al., "Glycerol-Induced Unraveling of the Tight Helical Conformation of *Escherichia coli* Type 1 Fimbriae," *J. Bacteriol. 174*:5145-5148, American Society for Microbiology (1992).

Adhin, M.R., et al., "Nucleotide Sequence from the ssRNA Bacteriophage JP34 Resolves the Discrepancy between Serological and Biophysical Classification," *Virology 170*:238-242, Academic Press, Inc. (1989).

Aguzzi, A., "Prion diseases, blood and the immune system: concerns and reality," *Haematologica* 85:3-10, Il Pensiero Scientifico Editore (Jan. 2000).

Ansel, K.M., et al., "In Vivo-activated CD4 T Cells Upregulate CXC Cheomkine Receptor 5 and Reprogram Their Response to Lymphoid Chemokines," *J. Exp. Med. 190*:1123-1134, The Rockefeller University Press (1999).

Ansel, K.M., et al., "A chemokine-driven positive feedback loop organizes lymphoid follicles," *Nature 406*:309-314, Nature Publishing Group (Jul. 2000).

Antonysamy, M.A., et al., "Evidence for a Role of IL-17 in Organ Allograft Rejection: IL-17 Promotes the Functional Differentiation of Dendritic Cell Progenitors," *J. Immunol. 162*:577-584, The American Association of Immunologists (1999).

Arenberg, D.A., et al., "The murine CC chemokine, 6C-kine, inhibits tumor growth and angiogenesis in a human lung cancer SCID mouse model," *Cancer Immunol. Immunother. 49*:587-592, Springer-Verlag (Jan. 2001).

Arnon, R., et al., "A mimotope peptide-based vaccine against *Schistosoma mansoni*: synthesis and characterization," *Immunology 101*:555-562, Blackwell Science, Ltd. (Dec. 2000).

Bachmann, M.F., and Zinkernagel, R.M., "The influence of virus structure on antibody responses and virus serotype formation," *Immunol. Today 17*:553-558, Elsevier Science, Ltd. (1996).

Bachmann, M.F., and Zinkernagel, R.M., "Neutralizing Antiviral B Cell Responses," *Annu. Rev. Immunol. 15*:235-270, Annual Reviews, Inc. (1997).

Bachmann, M.F., et al., "TRANCE, a Tumor Necrosis Factor Family Member Critical for CD40 Ligand-independent T Helper Cell Activation," *J. Exp. Med. 189*:1025-1031, The Rockefeller University Press (1999).

Banerjee, R.R., and Lazar, M.A., "Dimerization of Resistin and Resistin-like Molecules Is Determined by a Single Cysteine," *J. Biol. Chem. 276*:25970-25973, The American Society for Biochemistry and Molecular Biology, Inc. (Jul. 2001).

Bard, F. et al., "Peripherally administered antibodies against amyloid β-peptide enter the central nervous system and reduce pathology in a mouse model of Alzheimer disease," *Nat. Med. 6*:916-919, Nature Publishing Company (Aug. 2000).

Bass, S., and Yang, M., "Expressing cloned genes in *Escherichia coli*," in *Protein Function: A Practical Approach*, 2nd ed., Creighton, T.E., ed., IRL Press, Oxford, Great Britain, pp. 29-55 (1997).

Bernhagen, J., et al., "Purification, Bioactivity, and Secondary Structure Analysis of Mouse and Human Macrophage Migration Inhibitory Factor (MIF)," *Biochemistry 33*:14144-14155, American Chemical Society (1994).

Biaselle, C.J., and Millar, D.B., "Studies on Triton X-100 detergent micelles," *Biophys. Chem. 3*:355-361, North-Holland Publushing Company (1975).

Bleul, C.C., et al., "The lymphocyte chemoattractant SDF-1 is a ligand for LESTR/fusin and blocks HIV-1 entry," *Nature 382*:829-833, Nature Publishing Group (1996).

Blomfield, I.C., et al., "Type 1 Fimbriation and *fimE* Mutants of *Escherichia coli* K-12," *J. Bacteriol. 173*:5298-5307, American Society for Microbiology (1991).

Blomfield, I.C., et al., "Integration host factor stimulates both FimB- and FimE-mediated site-specific DNA inversion that controls phase variation of type 1 fimbriae expression in *Escherichia coli*," *Mol. Microbiol. 23*:705-717, Blackwell Science, Ltd. (1997).

Boder, E.T., and Wittrup, K.D., "Yeast Surface Display for Directed Evolution of Protein Expression, Affinity, and Stability," *Methods Enzymol. 328*:430-444, Academic Press (Oct. 2000).

Bonci, A., et al., "Relatedness and Phylogeny Within the Family of Periplasmic Chaperones Involved in the Assembly of Pili or Capsule-Like Structures of Gram-Negative Bacteria," *J. Mol. Evol. 44*:299-309, Springer-Verlag (1997).

Brandner, S., et al., "A crucial role for B cells in neuroinvasive scrapie," *Transfus. Clin. Biol. 6*:17-23, Elsevier, Paris (1999).

Brinton, Jr., C.C., "The structure, function, synthesis and genetic control of bacterial pili and a molecular model for DNA and RNA transport in gram negative bacteria," *Trans. N.Y. Acad. Sci. 27*:1003-1054, New York Academy of Sciences (1965).

Brown, K.D., et al., "A family of small inducible proteins secreted by leukocytes are members of a new superfamily that includes leukocyte and fibroblast-derived inflammatory agents, growth factors, and indicators of various activation processes," *J. Immunol.* 142:679-687, The American Association of Immunologists (1989).

Brown, P.M., et al., "A Single-Step Purification of Biologically Active Recombinant Human Interleukin-5 from a Baculovirus Expression System," *Protein Expr. Purif.* 6:63-71, Academic Press, Inc. (1995).

Brown, K.L., et al., "Scrapie replication in lymphoid tissues depends on prion protein-expressing follicular dendritic cells," *Nat. Med.* 11:1308-1312, Nature Publishing Company (1999).

Bullitt, E., et al., "Development of pilus organelle subassemblies in vitro depends on chaperone uncapping of a beta zipper," *Proc. Natl. Acad. Sci. USA* 93:12890-12895, National Academy Press (1996).

Bullitt, E., and Makowski, L., "Bacterial Adhesion Pili Are Heterologous Assemblies of Similar Subunits," *Biophys. J.* 74:623-632, Biophysical Society (1998).

Burger, J.A., et al., "Blood-derived nurse-like cells protect chronic lymphocytic leukemia B cells from spontaneous apoptosis through stromal cell-derived factor-1," *Blood* 96:2655-2663, The American Society of Hematology (Oct. 2000).

Burghoff, R.L., et al., "Utilization of the Mouse Large Intestine To Select an *Escherichia coli* F-18 DNA Sequence That Enhances Colonizing Ability and Stimulates Synthesis of Type 1 Fimbriae," *Infect. Immun.* 61:1293-1300, American Society for Microbiology (1993).

Cannon-Carlson S., et al., "Expression, Purification, and Characterization of Recombinant Human Interleukin-13 from NS-O Cells," *Protein Expr. Purif.* 12:239-248, Academic Press (1998).

Chabaud, M., et al., "Enhancing Effect of IL-17 on IL-1-Induced IL-6 and Leukemia Inhibitory Factor Production by Rheumatoid Arthritis Synoviocytes and Its Regulation by Th2 Cytokines," *J. Immunol.* 161: 409-414, The American Association of Immunologists (1998).

Chabaud, M., et al., "Human Interleukin-17. A T Cell-Derived Proinflammatory Cytokine Produced by the Rheumatoid Synovium," *Arthritis Rheum.* 42:963-970, Wiley-Liss, Inc. (1999).

Chabaud, M., et al., "Contribution of Interleukin 17 to synovium matrix destruction in rheumatoid arthritis," *Cytokine* 12:1092-1099, Cell Press (Jul. 2000).

Clark, H.F, et al., "Comparative Characterization of a C-Type Virus-Producing Cell Line (VSW) and a Virus-Free Cell Line (VH2) From *Vipera russelli*," *J. Natl. Cancer Inst.* 51:645-657, Oxford University Press (1973).

Clark-Lewis, I., et al., "Chemical Synthesis, Purification, and Characterization of Two Inflammatory Proteins, Neutrophil Activating Peptide 1 (Interleukin-8) and Neutrophil Activating Peptide 2," *Biochemistry* 30:3128-3135, American Chemical Society (1991).

Coffman, R.L., et al., "Antibody to Interleukin-5 Inhibits Helminth-Induced Eosinophilia in Mice," *Science* 245:308-310, American Association for the Advancement of Science (1989).

Cohen, C., and Parry D.A.D, "α-Helical coiled coils-a widespread motif in proteins," *Trends Biochem. Sci.* 11:245-248, Elsevier Science Publishing B.V. (1986).

Corti, M., et al., "GM1-ganglioside-Triton X-100 mixed micelles: changes of micellar properties studied by laser-light scattering and enzymatic methods," *Chem. Phys. Lipids* 28:197-214, Elsevier/North-Holland Scientific Publishers, Ltd. (1981).

Coutelier, J.-P., et al., "IgG2a Restriction of murine antibodies elicited by viral infections," *J. Exp. Med.* 165:64-69, The Rockefeller University Press (1987).

Crump, M.P., et al., "Solution Structure of Eotaxin, a Chemokine That Selectively Recruits Eosinophils in Allergic Inflammation," *J. Biol. Chem.* 273:22471-22479, The American Society for Biochemistry and Molecular Biology, Inc. (1998).

Davis, N.L., et al., "In Vitro Synthesis of Infectious Venezuelan Equine Encephalitis Virus RNA from a cDNA Clone: Analysis of a Viable Deletion Mutant," *Virology 171*:189-204, Academic Press (1989).
Daugherty, P.S., et al., "Development of an optimized expression system for the screening of antibody libraries displayed on the *Escherichia coli* surface," *Protein Eng. 12*:613-621, Oxford University Press (1999).
Dealwis, C., et al., "Crystal structure of chemically synthesized [N33A] stromal cell-derived factor 1α, a potent ligand for the HIV-1 "fusin" coreceptor," *Proc. Natl. Acad. Sci. USA 95*:6941-6946, National Academy Press (Jun. 2001).
Dodson, K.W., et al., "Outer-membrane PapC molecular usher discriminately recognized periplasmic chaperone-pilus subunit complexes," *Proc. Natl. Acad. Sci. USA 90*:3670-3674, National Academy Press (1993).
Dudler, J., et al., "Effect of interleukin 17 on proteoglycan degradation in murine knee joints," *Ann. Rheum. Dis. 59*:529-532, BMJ Publishing Group (Jul. 2000).
Eckhardt, S.G., et al., "Hepatitis B Virus Core Antigen Has Two Nuclear Localization Sequences in the Arginine-Rich Carboxyl Terminus," *J. Virol. 65*:575-582, American Society for Microbiology (1991).
Eisenmesser, E.Z., et al., "Expression, Purification, Refolding, and Characterization of Recombinant Human Interleukin-13: Utilization of Intracellular Processing," *Protein Expr. Purif. 20*:186-195, Academic Press (Nov. 2000).
Eisenmesser, E.Z., et al., "Solution Structure of Interleukin-13 and Insights into Receptor Engagement," *J. Mol. Biol. 310*:231-241, Academic Press (Jun. 2001).
Eisenstein, B.I., "Phase Variation of Type 1 Fimbriae in *Escherichia coli* Is Under Transcriptional Control," *Science 214*:337-339, American Association for the Advancement of Science (1981).
Elisseeva, E.L., et al., "NMR Studies of Active N-terminal Peptides of Stromal Cell-derived Factor-1," *J. Biol. Chem. 275*:26799-26805, The American Society for Biochemistry and Molecular Biology, Inc. (Sep. 2000).
Eshdat, Y., et al., "Dissociation and Reassembly of *Escherichia coli* Type 1 Pili," *J. Bacteriol. 148*:308-314, American Society for Microbiology (1981).
Ettinger, R., et al., "A Critical Role for Lymphotoxin-β Receptor in the Development of Diabetes in Nonobese Diabetic Mice," *J. Exp. Med. 193*:1333-1339, The Rockefeller University Press (Jun. 2001).
Fehr, T., et al., "Role of Repetitive Antigen Patterns for Induction of Antibodies Against Antibodies," *J Exp. Med. 185*:1785-1792, The Rockefeller University Press (1997).
Folkman, J., and Klagsbrun, M., "Angiogenic Factors," *Science 235*:442-447, American Association for the Advancement of Science (1987).
Folkman, J., "Angiogenesis in cancer, vascular, rheumatoid and other disease," *Nat. Med. 1*:27-31, Nature Publishing Company (1995).
Forssmann, U., et al., "Eotaxin-2, a Novel CC Chemokine that Is Selective for the Chemokine Receptor CCR3, and Acts Like Eotaxin on Human Eosinophil and Basophil Leukocytes," *J. Exp. Med. 185*:2171-2176, The Rockefeller University Press (1997).
Fossiez, F., et al., "T Cell Interleukin-17 Induces Stromal Cells to Produce Proinflammatory and Hematopoietic Cytokines," *J. Exp. Med. 183*:2593-2603, The Rockefeller University Press (1996).
Fossiez F., et al., "Interleukin-17," *Intern. Rev. Immunol. 16*:541-551, Harwood Academic Publishers (1998).
Fujiwara, K., et al., "Novel preparation method of immunogen for hydrophobic hapten, enzyme immunoassay for daunomycin and adriamycin," *J. Immunol. Methods 45*:195-203, Elsevier/North-Holland Biomedical Press (1981).
Gally, D.L., et al., "Environmental Regulation of the *fim* Switch Controlling Type 1 Fimbrial Phase Variation in *Escherichia coli* K-12: Effects of Temperature and Media," *J. Bacteriol. 175*:6186-6193, American Society for Microbiology (1993).
Gally, D. L., et al., "Interaction of FimB and FimE with the *fim* switch that controls the phase variation of type 1 fimbriated in *Escherichia coli* K-12," *Mol. Microbiol. 21*:725-738, Blackwell Science, Ltd. (1996).
Gherardi, E. et al., "A single-step procedure for cloning and selection of antibody-secreting hybridomas," *J. Immunol. Methods 126*:61-68, Elsevier (1990).
Golmohammadi, R., et al., "The crystal structure of bacteriophage Qβ at 3.5Å resolution," *Structure 4*:543-554, Current Biology, Ltd. (1996).
Gunn, M.D., et al., "A B-cell-homing chemokine made in lymphoid follicles activates Burkitt's lymphoma receptor-1," *Nature 391*:799-803, Nature Publishing Group (1998).

Hanes, J., et al., "Picomolar affinity antibodies from a fully synthetic naive library selected and evolved by ribosome display," *Nat. Biotechnol. 18*:1287-1292, Nature Publishing Company (Dec. 2000).

Hanson, M.S., et al., "Purification of the *Escherichia coli* Type 1 Pilin and Minor Pilus Proteins and Partial Characterization of the Adhesin Protein," *J. Bacteriol. 170*:3350-3358, American Society for Microbiology (1988).

Hanson, M.S., and Brinton, Jr., C.C., "Identification and charaterization of *E. coli* type-1 pilus tip adhesion protein," *Nature 332*:265-268, Nature Publishing Group (1988).

Harrison, J.L., et al., "Screening of Phage Antibody Libraries," *Methods Enzymol. 267*:83-109, Macmillan Publishers, Ltd. (1996).

Haslam, D.B., et al., "The amino-terminal domain of the P-pilus adhesin determines receptor specificity," *Mol. Microbiol. 14*:399-409, Blackwell Scientific Publications (1994).

Hedrick, J.A., and Zlotnik, A., "Identification and Characterization of Novel β Chemokine Containing Six Conserved Cysteines," *J. Immunol. 159*: 1589-1593, The American Association of Immunologists (1997).

Heveker, N., et al., Dissociation of the signalling and antiviral properties of SDF-1-derived small peptides, *Curr. Biol. 8*:369-376, Current Biology, Ltd. (1998).

Hirel, P.-H., et al., "Extent of N-terminal methionine excision from *Escherichia coli* proteins is governed by the side-chain length of the penultimate amino acid," *Proc. Natl. Acad. Sci. USA 86*:8247-8251, National Academy Press (1989).

Holmes, W.D., et al., "Solution Studies of Recombinant Human Stromal-Cell-Derived Factor-1," *Prot. Expr. Purif. 21*:367-377, Academic Press (Apr. 2001).

Holmgren, A., et al., "Conserved immunoglobulin-like features in a family of periplasmic pilus chaperones in bacteria," *EMBO J. 11*:1617-1622, Oxford University Press (1992).

Holmgren, A., and Bränden, C.-I., "Crystal structure of chaperone protein PapD reveals an immunoglobulin fold," *Nature 342*:248-251, Nature Publishing Group (1989).

Hultgren, S.J., et al., "The PapG adhesin of uropathogenic *Escherichia coli* contains separate regions for receptor binding and for the incorporation into the pilus," *Proc. Nat. Acad. Sci. USA 86*:4357-4361, National Academy Press (1989).

Hultgren, S.J., et al., "PapD and superfamily of periplasmic immunoglobulin-like pilus chaperones," *Adv. Prot. Chem. 44*:99-123, Academic Press, Inc. (1993).

Hultgren, S.J., et al., "Pilus and Nonpilus Bacterial Adhesins: Assembly and Function in Cell Recognition," *Cell 73*:887-901, Cell Press (1993).

Hultgren, S.J., et al., "Bacterial Adhesins and Their Assembly," in *Escherichia coli and Salmonella*, Neidhardt, F.C., et al., eds., ASM Press, Washington, D.C. pp. 2730-2756 (1996).

Humbles, A.A., et al., "Kinetics of Eotaxin Generation and Its Relationship to Eosinophil Accumulation in Allergic Airways Disease: Analysis in a Guinea Pig Model In Vivo," *J. Exp. Med. 186*:601-612, The Rockefeller University Press (1997).

Hung, D.L., et al., "Molecular basis of two subfamilies of immunoglobulin-like chaperones," *EMBO J. 15*:3792-3805, Oxford University Press (1996).

Hung, D.L. and Hultgren, S.J., "Pilus Biogenesis via the Chaperone/Usher Pathway: An Integration of Structure and Function," *J. Struct. Biol. 124*:201-220, Academic Press (1998).

Ikeda, T., et al., "Determination of Three Isoforms of the Receptor Activator of Nuclear Factor-κB Ligand and Their Differential Expression in Bone and Thymus," *Endocrinology 142*:1419-1426, The Endocrine Society (Apr. 2001).

Ingley E., et al., "Production and purification of recombinant human interleukin-5 from yeast and baculovirus expression systems," *Eur. J. Biochem. 196*:623-629, Blackwell Science, Ltd. (1991).

Jacob-Dubuisson, F., et al., "PapD chaperone function in pilus biogenesis depends on oxidant and chaperone-like activities of DsbA," *Proc. Natl. Acad. Sci. USA 91*:11552-11556, National Academy Press (1994).

Jacob-Dubuisson, F., et al., "Initiation of assembly and association of the structural elements of a bacterial pilus depend on two specialized tip proteins," *EMBO J. 12*:837-847, Oxford University Press (1993).

Jacob-Dubuisson, F., et al., "Chaperone-assisted Self-assembly of Pili Independent of Cellular Energy," *J. Biol. Chem. 269*:12447-12455, The American Society for Biochemistry and Molecular Biology, Inc. (1994).

Jiang, X., et al., "Norwalk Virus Genome Cloning and Characterization," *Science 250*:1580-1583, American Association for the Advancement of Science (1990).

Jones, C.H., et al., "FimC is a periplasmic PapD-like chaperone that directs assembly of type 1 pili in bacteria," *Proc. Natl. Acad. Sci. USA 90*:8397-8401, National Academy Press (1993).

Jones, C.H., et al., "FimH adhesin of type 1 pili is assembled into a fibrillar tip structure in the Enterobacteriaceae," *Proc. Natl. Acad. Sci. USA 92*:2081-2085, National Academy Press (1995).

Josien, R., et al., "TRANCE, a Tumor Necrosis Factor Family Member, Enhances the Longevity and Adjuvant Properties of Dendritic Cells In Vivo," *J. Exp. Med. 191*:495-501, The Rockefeller University Press (Feb. 2000).

Jovanovic, D.V., et al., "IL-17 Stimulates the Production and Expression of Proinflammatory Cytokines, IL-β and TNF-α, by Human Macrophages," *J. Immunol. 160*:3513-3521, The American Association of Immunologists (1998).

Kapp, U., et al., "Interleukin 13 Is Secreted by and Stimulates the Growth of Hodgkin and Reed-Sternberg Cells," *J. Exp. Med. 189*:1939-1945, The Rockefeller University Press (1999).

Kastelein, R.A. et al., "Effect of the sequence upstream from the ribosome-binding site on the yield of protein from the cloned gene for phage MS2 coat protein," *Gene 23*:245-254, Elsevier (1983).

Kim, K.J., et al., "Inhibition of vascular endothelial growth factor-induced angiogenesis suppresses tumour growth in vivo," *Nature 362*:841-844, Nature Publishing Group (1993).

Kim, K.-H., et al., "A Cysteine-rich Adipose Tissue-specific Secretory Factor Inhibits Adipocyte Differentiation," *J. Biol. Chem. 276*:11252-11256, The American Society for biochemistry and Molecular Biology, Inc. (Apr. 2001).

Klemm, P., "The *fimA* gene encoding the type-1 fimbrial subunit of *Escherichia coli*. Nucleotide sequence and primary structure of the protein," *Euro. J. Biochem. 143*:395-399, Blackwell Science, Lts. (1984).

Klemm, P., and Christiansen, G., "Three *fim* genes required for the regulation of length and mediation of adhesion of *Escherichia coli* type 1 fimbriae," Mol. Gen. Genet. 208:439-445, Springer-Verlag (1987).

Klemm, P., et al., "The major subunit of *Escherichia coli* type 1 fimbriate is not required for D-mannose-specific adhesion," *Mol. Microbiol. 4*:553-559, Blackwell Scientific Publications (1990).

Klemm, P., and Christiansen, G., "The *fimD* gene required for cell surface localization of *Escherichia coli* type 1 fimbriae," *Mol. Gen. Genet. 220*:334-338, Springer-Verlag (1990).

Klemm, P., "FimC, a chaperone-like periplasmic protein of *Escherichia coli* involved in biogenesis of type 1 fimbriae," *Res. Microbiol. 143*:831-838, Institut Pasteur/Elsevier (1992).

Klemm, P., and Krogfelt, K.A., "Type 1 Fimbriae of *Escherichia coli*," in *Fimbriae*, Klemm, P., ed., CRC Press, Inc., Boca Raton, FL., pp. 9-26 (1994).

Kodama, S., et al., "Characterization of recombinant murine interleukin 5 expressed in Chinese hamster ovary cells," *Glycobiology 2*:419-427, Oxford University Press (1992).

Kodama, S., et al., "Carbohydrate Structures of Human Interleukin 5 Expressed in Chinese Hamster Ovary Cells," *J. Biochem. (Tokyo) 110*:693-701, Japanese Biochemical Society (1991).

Kopf, M., et al., "IL-5-Deficient Mice Have a Development Defect in CD5[+] B-1 Cells and Lack Eosinophilia but have Normal Antibody and Cytotoxic T Cell Responses," *Immunity 4*:15-24, Cell Press (1996).

Koschel, M., et al., "Extensive Mutagenesis of the Hepatitis B Virus Core Gene and Mapping of Mutations That Allow Capsid Formation," *J. Virol 73*:2153-2160, American Society for Microbiology (1999).

Koths, K., "Structure-Function Studies on Human Macrophage Colony-Stimulating Factor (M-CSF)," *Mol. Reprod. Dev. 46*:31-38, Wiley-Liss, Inc. (1997).

Kozlovska, T.M., et al., "Recombinant RNA phage Qβ capsid particles synthesized and self-assembled in *Escherichia coli*," *Gene* 137:133-137, Elsevier Science Publishers B.V. (1993).

Kozlovskaya, T.M., et al., "Formation of capsid-like structures as a result of the expression of a cloned envelope protein gene from RNA-containing bacteriophage fr," *Dokl. Akad. Nauk. SSSR 287:* 452-455, Erivan Akademiia Nauk Armianskoi Ssr (1986).

Kozlovskaya, T.M., et al., "Formation of capsid-like structures as a result of the expression of a cloned envelope protein gene from RNA-containing bacteriophage fr," STNEasy, Accession No. 1986:219892, CAplus English abstract (1986) (Document NPL111).

Krogfelt, K.A., et al., "Direct Evidence that the FimH Protein Is the Mannose-Specific Adhesin of *Escherichia coli* Type 1 Fimbriae," *Infect. Immun.* 58:1995-1998, American Society for Microbiology (1990).

Kuehn, M.J., et al., "Structural Basis of Pilus Subunit Recognition by the PapD Chaperone," *Science* 262:1234-1241, American Association for the Advancement of Science (1993).

Kunimoto, D.Y, et al., "High-level production of murine interleukin-5 (IL-5) utilizing recombinant baculovirus expression. Purification of the rIL-5 and its us in assessing the biologic role of IL-5 glycosylation," *Cytokine* 3:224-230, W.B. Saunders Company (1991).

Landschulz, W.H., et al., "The Leucine Zipper: A Hypothetical Structure Common to a New Class of DNA Binding Proteins," *Science 240:*1759-1764, American Association for the Advancement of Science (1988).

Leake, C.J., et al., "Cytopathic Effect and Plaque Formation by Arboviruses in a Continuous Cell Line (XTC-2) from the Toad *Xenopus laevis,*" *J. gen. Virol.* 35:335-339, Cambridge University Press (1977).

Lee, K.H., et al., "Two-Dimensional Electrophoresis of Proteins as a Tool in the Metabolic Engineering of Cell Cycle Regulation," *Biotech. Bioeng. 50:*336-340, John Wiley & Sons, Inc. (1996).

Leech, M., et al., "Involvement of macrophage migration inhibitory factor in the evolution of rat adjuvant arthritis," *Arthritis Rheum. 41:*910-917, Arthritis Foundation (1998).

Leech, M., et al. "Regulation of macrophage migration inhibitory factor by endogenous glucocorticoid in rat adjuvant-induced arthritis," *Arthritis Rheum.* 43:827-833, Arthritis Foundation (Apr. 2000).

Liljeström, P., and Garoff, H., "A new generation of animal cell expression vectors based on the semliki forest virus replicon," *Bio/technology 9:*1356-1361, Nature Publishing Company (1991).

Liljeström, P., "Alphavirus expression systems," *Curr. Opin. Biotechnol.* 5:495-500, Current Biology, Ltd. (1994).

Lim, F., et al., "The RNA-binding Site of Bacteriophage Qβ Coat Protein," *J. Biol. Chem.* 271:31839-31845, The American Society for Bichemistry and Molecular Biology, Inc. (1996).

Lin, E.Y., et al., "Colony-stimulating Factor 1 Promotes Progression of Mammary Tumors to Malignancy," *J. Exp. Med. 193:*727-739, The Rockefeller University Press (Mar. 2001).

Lindberg, F., et al., "PapD, a Periplasmic Transport Protein in P-Pilus Biogenesis," *J. Bacteriol. 171:*6052-6058, American Society for Microbiology (1989).

Lo-Man, R., et al., "A recombinant virus-like particle system derived from parvovirus as an efficient antigen carrier to elicit a polarized Th1 immune response without adjuvant," *Eur. J. Immunol. 28:*1401-1407, Wiley-VCH Verlag GmbH (1998).

López, O., et al., "Direct formation of mixed micelles in the solubilization of phospholipid liposomes by Triton X-100," *FEBS Lett. 426:*314-318, Elsevier (1998).

Lowe, M.A., et al., "Immunoelectron Microscopic Analysis of Elongation of Type 1 Fimbriae in *Escherichia coli*," *J. Bacteriol.* 169:157-163, American Society for Microbiology (1987).

Lu, D., et al., "Identification of the Residues in the Extracellular Region of KDR Important for Interaction with Vascular Endothelial Growth Factor and Neutralizing Anti-KDR Antibodies," *J. Biol. Chem.* 275:14321-14330, The American Society for Biochemistry and Molecular Biology, Inc. (May 2000).

Lum, L., et al., "Evidence for a Role of a Tumor Necrosis Factor-α(TNF-α)-converting Enzyme-like Protease in Shedding of TRANCE, a TNF Family Member Involved in Osteoclastogenesis and Dendritic Cell Survival," *J. Biol. Chem.* 274:13613-13618, The American Society for Biochemistry and Molecular Biology, Inc. (1999).

Lundstrom, K., "Alphaviruses as expression vectors," *Curr. Opin. Biotechnol.* 8:578-582, Current Biology, Ltd. (1997).

Luther, S.A., et al., "BLC Expression in Pancreatic Islets Causes B Cell Recruitment and Lymphotoxin-Dependent Lymphoid Neogenesis," *Immunity* 12:471-481, Cell Press (May 2000).

Mackay, J.L., and Browning, J.L., "Turning off follicular dendritic cells," *Nature 395:*26-27, Macmillan Magazines, Ltd. (1998).

Martiny-Baron, G., and Marmé, D., "VEGF-mediated tumour angiogenesis: a new target for cancer therapy," *Curr. Opin. Biotechnol.* 6:675-680, Current Biology, Ltd. (1995).

Matsui, S.M., et al., "The Isolation and Characterization of a Norwalk Virus-Specific cDNA," *J. Clin. Invest.* 87:1456-1461, The American Society for Clinical Investigation, Inc. (1991).

Matsumoto, M., et al., "Role of Lymphotoxin and the Type 1 TNF Receptor in the Formation of Germinal Centers," *Science* 271:1289-1291, American Association for the Advancement of Science (1996).

Matthews, W., et al., "A receptor tyrosine kinase cDNA isolated from a population of enriched primitive hematopoietic cells and exhibiting close genetic linkage to *c-kit,*" *Proc. Natl. Acad. Sci. USA* 88:9026-9030, National Academy Press (1991).

Matusevicius, D., et al., "Interleukin-17 mRNA expression in blood and CSF mononuclear cells is augmented in multiple sclerosis," *Mult. Scler.* 5:101-104, Stockton Press (1999).

Mayer, K.L., and Stone, M.J., "NMR Solution Structure and Receptor Peptide Binding of the CC Chemokine Eotaxin-2," *Biochemistry 39:*8382-8395, American Chemical Society (Jul. 2000).

McClain, M.S., et al., "Roles of *fimB* and *fimE* in Site-Specific DNA Inversion Associated with Phase Variation of Type 1 Fimbriae in *Escherichia coli,*" *J. Bacteriol. 173:*5308-5314, American Society for Microbiology (1991).

McPherson, P.S., "Regulatory Role of SH3 Domain-mediated Protein-Protein Interactions in Synaptic Vesicle Endocytosis," *Cell Signal 11:*229-238, Elsevier Science, Inc. (1999).

Mikulowska, A., et al., "Macrophage Migration Inhibitory Factor Is Involved in the Pathogenesis of Collagen Type II-Induced Arthritis in Mice," *J. Immunol.* 158:5514-5517, The American Association of Immunologists (1997).

Millauer, B., et al., "Glioblastoma growth inhibited in vivo by a dominant-negative Flk-1 mutant," *Nature* 367:576-579, Nature Publishing Group (1994).

Min, H., et al., "Osteoprotegerin Reverses Osteoporosis by Inhibiting Endosteal Osteoclasts and Prevents Vascular Calcification by Blocking a Process Resembling Osteoclastogenesis," *J. Exp. Med. 192:*463-474, The Rockefeller University Press (Aug. 2000).

Mitchell, D.L., et al., "Purification and characterization of recombinant murine interleukin-5 glycoprotein, from a Baculovirus expression system," *Biochem. Soc. Trans. 21:*332S, Portland Press (1993).

Montrasio, F. et al., "Impaired Prion Replication in Spleens of Mice Lacking Functional Follicular Dendritic Cells," *Science* 288:1257-1259, American Association for the Advancement of Science (May 2000).

Morein, B., et al., "Iscom, a novel structure for antigenic presentation of membrane proteins from enveloped viruses," *Nature 308:*457-460, Nature Publishing Group (1984).

Moriya, C., et al., "Large quantity production with extreme convenience of human SDF-1α and SDF-1β by a Sendai virus vector," *FEBS Lett.* 425:105-111, Amsterdam Elsevier Science B.V. (1998).

Müller, A., et al., "Involvement of chemokine receptors in breast cancer metastasis," *Nature* 410:50-56, Nature Publishing Group (Mar. 2001).

Murphy, Jr., K.P., et al., "Expression of Human Interleukin-17 in *Pichia pastoris*: Purification and Characterization," *Protein Expr. Purif.* 12:208-214, Academic Press (1998).

Nagira, M., et al., "Molecular Cloning of a Novel Human CC Chemokine Secondary Lymphoid-Tissue Chemokine That Is a Potent Chemoattractant for Lymphocytes and Mapped to Chromosome 9p13," *J. Biol. Chem.* 272:19518-19524, The American Society for Biochemistry and Molecular Biology, Inc. (1997).

Nanki, T., et al., "Stromal Cell-Derived Factor-1-CXC Chemokine Receptor 4 Interactions Play a Central Role in $CD4^+$ Cell Accumulation in Rheumatoid Arthritis Synovium," *J. Immunol. 165*:6590-6598, The American Association of Immunologists (Dec. 2000).

Naureckiene, S., and Uhlin, B.E., "In vitro analysis of mRNA processing by Rnase E in the pap operon of *Esherichia coli*," *Mol. Microbiol. 21*:55-68, Blackwell Science, Ltd. (1996).

Neirynck, S., et al., "A universal influenza A vaccine based on the extracellular domain of the M2 protein," *Nat. Med. 5*:1157-1163, Nature Publishing Company (1999).

Newman, J.V., et al., "Stimulation of *Escherichia coli* F-18Col Type-1 fimbriae synthesis by *leuX*," *FEMS Microbiol. Lett. 122*:281-287, Elsevier (1994).

Ni, C.-Z., et al., "Crystal structure of the coat protein from the GA bacteriophage: Model of the unassembled dimer," *Protein Sci. 5*:2485-2493, Cambridge University Press (1996).

Nilsson, P., et al., "Mutations Affecting mRNA Processing and Fimbrial Biogenesis in the *Escherichia coli pap* Operon," *J. Bacteriol. 178*:683-690, American Society for Microbiology (1996).

Oberlin, E., et al., "The CXC chemokine SDF-1 is the ligand for LESTR/fusin and prevents infection by T-cell-line-adapted HIV-1," *Nature 382*:833-835, Nature Publishing Group (1996).

Ohnishi, Y., et al., "Crystal Structure of Recombinant Native SDF-1α with Additional Mutagenesis Studies: An Attempt at a More Comprehensive Interpretation of Accumulated Structure-Activity Relationship Data," *J. Interferon Cytokine Res. 20*:691-700, Mary Ann Liebert, Inc. (Aug. 2000).

Olszewska, W., et al., "Protection against Measles Virus-Induced Encephalitis by Anti-mimotope Antibodies: The Role of Antibody Affinity," *Virology 272*:98-105, Academic Press (Jun. 2000).

Orndorff, P.E., and Falkow, S., "Identification and Characterization of a Gene Product That Regulates Type 1 Piliation in *Escherichia coli*," *J. Bacteriol. 160*:61-66, American Society for Microbiology (1984).

Orndorff, P.E., and Falkow, S., "Nucleotide Sequence of *pilA*, the Gene Encoding the Structural Component of Type 1 Pili in *Escherichia coli*," *J. Bacteriol. 162*:454-457, American Society for Microbiology (1985).

O'Shea, E.K., et al., "Evidence That the Leucine Zipper Is a Coiled Coil," *Science 243*:538-542, American Association for the Advancement of Science (1989).

O'Shea, E.K., et al., "Mechanism of Specificity in the Fos-Jun Oncoprotein Heterodimer," *Cell 68*:699-708, Cell Press (1992).

Pandit, J., et al., "Three-dimensional Structure of Dimeric Human Recombinant Macrophage Colony-Stimulating Factor," *Science 258*:1358-1362, American Association for the Advancement of Science (1992).

Pierrot, C., et al., "Expression of Rat Interleukin-5 and Generation of Neutralizing Antiserum: a Comparative Study of Rat IL-5 Produced in *Escherichia coli* and Insect Cells," *Biochem. Biophys. Res. Commun. 253*:756-760, Academic Press (1998).

Pierson-Mullany, L.K., et al. "Characterization of polyclonal allergen-specific IgE responses by affinity distributions," *Mol. Immunol. 37*:613-620, Elsevier Science, Ltd. (Aug. 2000).

Piossek, C., et al., "Vascular Endothelial Growth Factor (VEGF) Receptor II-derived Peptides Inhibits VEGF," *J. Biol. Chem. 274*:5612-5619, The American Society for Biochemistry and Molecular Biology, Inc. (1999).

Presta, L.G., et al., "Humanization of an Anti-Vascular Endothelial Growth Factor Monoclonal Antibody for the Therapy of Solid Tumors and Other Disorders," *Cancer Res. 57*:4593-4599, The American Association for Cancer Research (1997).

Priano, C., et al., "A Complete Plasmid-based Complementation System for RNA Coliphage Qβ: Three Proteins of Bacteriophages Qβ (Group III) and SP (Group IV) can be Interchanged," *J. Mol. Biol. 249*:283-297, Academic Press, Ltd. (1995).

Proudfoot, A.E.I., et al., "Preparation and characterization of human interleukin-5 expressed in recombinant *Escherichia coli*," *Biochem. J. 270*:357-361, Portland Press, Ltd. (1990).

Renner, W.A., et al., "Recombinant Cyclin E Expression Activates Proliferation and Obviates Surface Attachment of Chinese Hamster Ovary (CHO) Cells in Protein-Free Medium," *Biotech. Bioeng. 47*:476-482, John Wiley & Sons, Inc. (1995).

Risau, W., "Mechanisms of angiogenesis," *Nature 386*:671-674, Nature Publishing Group (1997).

Ritter, A., et al., "The Pai-associated *leuX* specific tRNA$_5^{Leu}$ affects type 1 fimbriation in pathogenic *Escherichia coli* by control of FimB recombinase expression," *Mol. Microbiol. 25*:871-882, Blackwell Science, Ltd. (1997).

Roesch, P.L., and Blomfield, I.C., "Leucine alters the interaction of the leucine-responsive regulatory protein (Lrp) with the *fim* switch to stimulate site-specific recombination in *Escherichia coli*," *Mol. Microbiol. 27*:751-761, Blackwell Science, Ltd. (1998).

Roher, A.E., et al., "Isolation and Chemical Characterization of Alzheimer's Disease Paired Helical Filament Cytoskeletons: Differentiation from Amyloid Plaque Core Protein," *J. Cell Biol. 107*:2703-2716, The Rockefeller University Press (1988).

Roher, A.E., et al., "Morphological and Biochemical Analyses of Amyloid Plaque Core Proteins Purified from Alzheimer Disease Brain Tissue," *J. Neurochem. 61*:1916-1926, Raven Press, Ltd. (1993).

Romagnani, S., "The Th 1/Th2 paradigm," *Immunol. Today 18*:263-266, Elsevier Science, Ltd. (1997).

Rothenberg, M.E., et al., "Targeted Disruption of the Chemokine Eotaxin Partially Reduces Antigen-induced Tissue Eosinophilia," *J. Exp. Med. 185*:785-790, The Rockefeller University Press (1997).

Rusconi, S., et al., "In vitro inhibition of HIV-1 by Met-SDF-1β alone or in combination with antiretroviral drugs," *Antivir. Ther. 5*:199-204, International Medical Press (Sep. 2000).

Russell, P.W., and Orndorff, P.E., "Lesions in Two *Escherichia coli* Type 1 Pilus Genes Alter Pilus Number and Length without Affecting Receptor Binding," *J. Bacteriol. 174*:5923-5935, American Society for Microbiology (1992).

Santos, L., et al., "Role of macrophage migration inhibitory factor (MIF) in murine antigen-induced arthritis: interaction with glucocorticoids," *Clin. Exp. Immunol. 123*:309-314, Blackwell Science (Feb. 2001).

Saulino, E.T., et al., "Ramifications of kinetic partitioning on usher-mediated pilus biogenesis," *EMBO J. 17*:2177-2185, Oxford University Press (1998).

Schenk, D., et al., "Immunization with amyloid-β attenuates Alzheimer-disease-like pathology in the PDAPP mouse," *Nature 400*:173-177, Nature Publishing Group (1999).

Schlesinger, S., "Alphaviruses—vectors for the expression of heterologous genes," *Trends Biotechnol. 11*:18-22, Elsevier Science Publishers, Ltd. (1993).

Selkoe, D.J., "Translating cell biology into therapeutic advances in Alzheimer's disease," *Nature 399*:A23-A31, Nature Publishing Group (1999).

Slonim, L.N., et al., "Interactive surface in the PapD chaperone cleft is conserved in pilus chaperone superfamily and essential in subunit recognition and assembly," *EMBO J. 11*:4747-4756, Oxford University Press (1992).

Smyth, C.J., et al., "Fimbrial adhesins: similarities and variations in structure and biogenesis," *FEMS Immun. Med. Microbiol. 16*:127-139, Elsevier (1996).

Soto, H., et al., "The CC chemokine 6Ckine binds the CXC chemokine receptor CXCR3," *Proc. Natl. Acad. Sci. USA 95*:8205-8210, National Academy Press (1998).

Soto, G.E., et al., "Periplasmic chaperone recognition motif of subunits mediates quaternary interactions in the pilus," *EMBO J. 17*:6155-6167, Oxford University Press (1998).

Soto, G.E., and Hultgren, S.J., "Bacterial Adhesins: Common Themes and Variations in Architecture and Assembly," *J. Bacteriol. 181*:1059-1071, American Society for Microbiology (1999).

Steppan, C.M., et al., "The hormone resistin links obesity to diabetes," *Nature 409*:307-312, Nature Publishing Group (Jan. 2001).

Stollar, V., "Togaviruses in Cultured Arthropod Cells," in *The Togaviruses. Biology, Structure, Replication*, Schlesinger, R.W., ed., Academic Press, Inc. New York, N.Y., pp. 583-621 (1980).

Strauss, J., and Strauss, E.G., "The Alphaviruses: Gene Expression, Replication, and Evolution," *Microbiol. Rev. 58*:491-562, American Society for Microbiology (1994).

Striker, R.T., et al., "Stable Fiber-forming and Nonfiber-forming Chaperone-Subunit Complexes in Pilus Biogenesis," *J. Biol. Chem. 269*:12233-12239, The American Society for Biochemistry and Molecular Biology, Inc. (1994).

Sturchler-Pierrat, C., et al., "Two amyloid precursor protein transgenic mouse models with Alzheimer disease-like pathology," *Proc. Natl. Acad. Sci. USA 94*:13287-13292, National Academy Press (1997).

Sun, H.-W_., et al., "Crystal structure at the 2.6-Å resolution of human macrophage migration inhibitory factor," *Proc. Natl. Acad. Sci. USA 93*:5191-5196, National Academy Press (1996).

Tang, J.-L., et al., "Interleukin-17 antagonism inhibits acute but not chronic vascular rejection," *Transplantation 72*:348-350, Lippincott Williams & Wilkens (Jul. 2001).

Tanimori, H., et al., "Enzyme immunoassay of neocarzinostatin using β-galactosidase as label," *J. Pharm. Dyn. 4*:812-819, Pharmaceutical Society of Japan (1981).

Teixeira, M.M., et al., "Chemokine-induced Eosinophil Recruitment. Evidence of a Role for Endogenous Eotaxin in an In Vivo Allergy Model in Mouse Skin," *J. Clin. Invest. 100*:1657-1666, The American Society for Clinical Investigation, Inc. (1997).

Tewari, R., et al., "Neutrophil Activation by Nascent FimH Subunits of Type I Fimbriae Purified from the Periplasm of *Escherichia coli*," *J. Biol. Chem. 268*:3009-3015, The American Society for Biochemistry and Molecular Biology, Inc. (1993).

Teunissen, M.B.M., et al., "Interleukin-17 and Interferon-γ Synergize in the Enhancement of Proinflammatory Cytokine Production by Human Keratinocytes," *J. Invest. Dermatol. 111*:645-649, The Society for Investigative Dermatology, Inc. (1998).

Thanassi, D.G., et al., "The PapC usher forms an oligomeric channel: Implications for pilus biogenesis across the outer membrane," *Proc. Natl. Acad. Sci. USA 95*:3146-3151, National Academy Press (1998).

De Togni, P., et al., "Abnormal Development of Peripheral Lymphoid Organs in Mice Deficient in Lymphotoxin," *Science 264*:703-707, American Association for the Advancement of Science (1994).

Topchieva, I., and Karezin, K., "Self-Assembled Supramolecular Micellar Structures Based on Non-ionic Surfactants and Cyclodextrins," *J. Colloid Interface Sci. 213*:29-35, Academic Press (1999).

Twomey, T., et al., "Structure and immunogenicity of experimental foot-and-mouth disease and poliomyelitis vaccines," *Vaccine 13*:1603-1610, Elsevier Science, Ltd. (1995).

Ulrich, R., et al., "Core particles of hepatitis B virus as carrier for foreign epitopes," *Adv. Virus Res. 50*:141-182, Academic Press (1998).

Vicari, A.P., et al., "Antitumor Effects of the Mouse Chemokine 6Ckine/SLC Through Angiostatic and Immunological Mechanisms," *J. Immunol. 165*:1992-2000, The American Association of Immunologists (Aug. 2000).

Visintin, M. et al., "Selection of antibodies for intracellular function using a two-hybrid in vivo system," *Proc. Natl. Acad. Sci. USA 96*:11723-11728, National Academy Press (1999).

Walse, B., et al., "Transferred nuclear Overhauser effect spectroscopy study of a peptide from the PapG pilus subunit bound by the *Escherichia coli* PapD chaperone," *FEBS Lett. 412*:115-120, Elsevier Science B.V. (1997).

Warnes, A., et al., "Expression of the measles virus nucleoprotein gene in *Escherichia coli* and assembly of nucleocapsid-like structures," *Gene 160*:173-178, Elsevier Science B.V. (1995).

Watson, E., et al., "Structure determination of the intact major sialylated oligosaccharide chains of recombinant human erythropoietin expressed in Chinese hamster ovary cells," *Glycobiology 4*:227-237, Oxford University Press (1994).

Wei, Y.Q., et al., "Immunotherapy of tumors with xenogeneic endothelial cells as a vaccine," *Nat. Med. 6*:1160-1166, Nature Publishing Company (Oct. 2000).

Witherell, G.W., and Uhlenbeck, O.C., "Specific RNA Binding by Qβ Coat Protein," *Biochemistry 28*:71-76, American Chemical Society (1989).

Wong, C.K., et al., "Elevation of proinflammatory cytosine (IL-18, IL-17, IL-12) and Th2 cytokine (IL-4) concentrations in patients with systemic lupus erythematosus," *Lupus 9*:589-593, Macmillan Publishers Ltd. (2000).

Wu, Q., et al. "Reversal of Spontaneous Autoimmune Insulitis in Nonobese Diabetic Mice by Soluble Lymphotoxin Receptor," *J. Exp. Med. 193*:1327-1332, The Rockefeller University Press (Jun. 2001).

Wuttke, M., et al., "Structural Characterization of Human Recombinant and Bone-derived Bone Sialoprotein," *J. Biol. Chem. 276*:36839-36848, The American Society for Biochemistry and Molecular Biology, Inc. (Sep. 2001).

Wynne, S.A., et al., "The Crystal Structure of the Human Hepatitis B Virus Capsid," *Mol. Cell 3*:771-780, Cell Press (1999).

Xiong, C., et al., "Sindbis Virus: An Efficient, Broad Host Range Vector for Gene Expression in Animal Cells," *Science 243*:1188-1191, American Association for the Advancement of Science (1989).

Yao, Z., et al., "Human IL-17: A Novel Cytokine Derived from T Cells," *J. Immunol. 155*:5483-5486, The American Association of Immunologists (1995).

Yao, Z., et al., "Molecular characterization of the human interleukin (IL)-17 receptor," *Cytokine 9*:794-800, Academic Press, Ltd. (1997).

Yone, K., et al., "Epitopic Regions for Antibodies against Tumor Necrosis Factor α," *J. Biol. Chem. 270*:19509-19515, The American Society for Biochemistry and Molecular Biology, Inc. (1995).

Yuan, T.-T., et al., "Subtype-Independent Immature Secretion and Subtype-Dependent Replication Deficiency of a Highly Frequent, Naturally Occurring Mutation of Human Hepatitis B Virus Core Antigen," *J. Virol. 73*:10122-10128, American Society for Microbiology (1999).

Zang, M., et al., "Production of Recombinant Proteins in Chinese Hamster Ovary Cells Using A Protein-Free Cell Culture Medium," *Bio/Technology 13*:389-392, Nature Publishing Company (1995).

Zhou, S., and Standring, D.N., "Cys Residues of the Hepatitis B Virus Capsid Protein Are Not Essential for the Assembly of Viral Core Particles but Can Influence Their Stability," *J. Virol. 66*:5393-5398, American Society for Microbiology (1992).

Zimmermann, N., et al., "Murine Eotaxin-2: A Constitutive Eosinophil Chemokine Induced by Allergen Challenge and IL-4 Overexpression," *J. Immunol. 165*:5839-5846, The American Association of Immunologists (Nov. 2000).

Ziolkowska, M., et al., "High Levels of IL-17 in Rheumatoid Arthritis Patient: IL-15 Triggers In Vitro IL-17 Production Via Cyclosporin A-Sensitive Mechanism," *J. Immunol. 164*:2832-2838, The American Association of Immunologists (Mar. 2000).

Zuercher, A.W., et al., "Oral anti-IgE immunization with epitope-displaying phage," *Eur. J. Immunol. 30*:128-135, Wiley-Vch Verlag GmbH (Jan. 2000).

Fehr, T., et al., "T cell-independent type I antibody response against B cell epitopes expressed repetitively on recombinant virus particles," *Proc. Natl. Acad. Sci. USA 95*:9477-9481, National Academy Press (1998).

Frenkel, D., et al., "Generation of auto-antibodies towards Alzheimer's disease vaccination," *Vaccine 19*:2615-2619, Elsevier Science, Ltd. (Mar. 2001).

International Search Report for International Application No. PCT/IB02/00166 mailed on Oct. 29, 2002. European Patent Office, Netherland (2002).

International Search Report for International Application No. PCT/IB02/00168 mailed on Nov. 4, 2002. European Patent Office, Netherlands (2002).

Kozlovska, T.M., et al., "RNA Phage Qβ Coat Protein as a Carrier for Foreign Epitopes," *Intervirology 39*:9-15, S. Karger AG (1996).

Kratz, P.A., et al., "Native display of complete foreign protein domains on the surface of hepatitis B virus capsids," *Proc. Natl. Acad. Sci. USA 96*:1915-1920, National Academy of Sciences (1999).

Nieland, J.D., et al., "Chimeric Papillomavirus Virus-like Particles Induce a Murine Self-Antigen-Specific Protective and Therapeutic Antitumor Immune Response," *J. Cell. Biochem. 73*:145-152, Wiley-Liss, Inc. (1999).

Slepushkin, V.A., et al., "Protection of mice against influenza A virus challenge by vaccination with baculovirus-expressed M2 protein," *Vaccine 13*:1399-1402, Elsevier Science Ltd. (1995).

Vasiljeva, I., et al., "Mosaic Qβ coats as a new presentation model," *FEBS Lett. 431*:7-11, Federation of European Biochemical Societies (1998).

International Search Report for International Application No. PCT/IB 02/00166, mailed Jan. 31, 2003. European Patent Office, Netherlands (2002).

Baba, T.W., et al., "Pathogenicity of Live, Attenuated SIV After Mucosal Infection of Neonatal Macaques," *Science* 267:1820-1825, American Association for the Advancement of Science (1995).

Bachmann, M.F., et al., "Dendritic cells process exogenous viral proteins and virus-like particles for class I presentation to CD8+ cytotoxic T lymphocytes," *Eur. J. Immunol.* 26:2595-2600, VCH Verlagsgesellschaft mbH (1996).

Boorsma, M., et al., "A temperature-regulated replicon-based DNA expression system," *Nat. Biotechnol.* 18:429-432, Nature America, Inc. (Apr. 2000).

Borisova, G., et al., "Hybrid Hepatitis B Virus Nucleocapsid Bearing an Immunodominant Region from Hepatitis B Virus Surface Antigen," *J. Virol.* 67:3696-3701, American Society for Microbiology (1993).

Cesareni, G., "Peptide display on filamentous phage capsids: A new powerful tool to study protein-ligand interaction," *FEBS Lett.* 307:66-70, Elsevier Science Publishers B.V. (1992).

Connor, R.I., et al., "Immunological and Virological Analyses of Persons Infected by Human Immunodeficiency Virus Type 1 while Participating in Trials of Recombinant gp120 Subunit Vaccines," *J. Virol.* 72:1552-1576, American Society for Microbiology (1998).

Crameri, R. and Suter, M., "Display of biologically active proteins on the surface of filamentous phages: a cDNA cloning system for selection of functional gene products linked to the genetic information responsible for their production," *Gene* 137:69-75, Elsevier Science Publishers B.V. (1993).

Daniel, M.D., et al., "Protective Effects of a Live Attenuated SIV Vaccine with a Deletion in the *nef* Gene," *Science* 258:1938-1941, American Association for the Advancement of Science (1992).

de la Cruz, V.F., et al., "Immunogenicity and Epitope Mapping of Foreign Sequences via Genetically Engineered Filamentous Phage," *J. Biol. Chem.* 263:4318-4322, The American Society for Biochemistry and Molecular Biology, Inc. (1988).

Donnelly, J.J., et al., "DNA Vaccines," *Annu. Rev. Immunol.* 15:617-648, Annual Reviews, Inc. (1997).

Ebina, S., et al., "Chemical Modification of Bovine Pancreatic Trypsin Inhibitor for Single Site Coupling of Immunogenic Peptides for NMR Conformational Analysis," *J. Biol. Chem.* 264:7882-7888, The American Society for Biochemistry and Molecular Biology, Inc. (1989).

Esposito, G., et al., "Conformational study of a short *Pertussis* toxin T cell epitope incorporated in a multiple antigen peptide template by CD and two-dimensional NMR: Analysis of the structural effects on the activity of synthetic immunogens," *Eur. J. Biochem.* 217:171-187, Blackwell Science Ltd. on behalf of the Federation of European Biochemical Societies (1993).

Förster, E., et al., "Natural and recombinant enzymatically active or inactive bee venom phospholipase $A_2$ has the same potency to release histamine from basophils in patients with Hymenoptera allergy," *J. Allergy Clin. Immunol.* 95:1229-1235, Mosby-Year Book, Inc. (1995).

Frolov, I., et al., "Alphavirus-based expression vectors: Strategies and applications," *Proc. Natl. Acad. Sci. USA* 93:11371-11377, National Academy Press (1996).

Gilbert, S.C., et al., "A protein particle vaccine containing multiple malaria epitopes," *Nat. Biotechnol.* 15:1280-1284, Nature America Publishing (1997).

Greenstone, H.L., et al., "Chimeric papillomavirus virus-like particles elicit antitumor immunity against the E7 oncoprotein in an HPV16 tumor model," *Proc. Natl. Acad. Sci. USA* 95:1800-1805, National Academy Press (1998).

Hahn, C.S., et al., "Infectious Sindbis virus transient expression vectors for studying antigen processing and presentation," *Proc. Natl. Acad. Sci. USA* 89:2679-2683, National Academy Press (1992).

Harding, C.V., and Song, R., "Phagocytic Processing of Exogenous Particulate Antigens by Macrophages for Presentation by Class I MHC Molecules," *J. Immunol.* 153:4925-4933, The American Association of Immunologists (1994).

Hilleman, M.R., "Six decades of vaccine development—a personal history," *Nat. Med. Vaccine Suppl.* 4:507-514 (May 1998).

Hui, E. K-W. et al., "Hepatitis B viral core proteins with an N-terminal extension can assemble into core-like particles but cannot be enveloped," *J. Gen. Virol.* 80:2647-2659, Society for General Microbiology (1999).

Iannolo, G., et al., "Construction, Exploitation and Evolution of a New Peptide Library Displayed at High Density by Fusion to the Major Coat Protein of Filamentous Phage," *Biol. Chem.* 378:517-521, Walter de Gruyter & Co. (1997).

Iannolo, G., et al., "Modifying Filamentous Phage Capsid: Limits in the Size of the Major Capsid Protein," *J. Mol. Biol.* 248:835-844, Academic Press, Ltd. (1995).

Ikram, H., and Prince, A.M., "A method for coupling the Hepatitis B surface antigen to aldehyde-fixed erythrocytes for use in passive hemagglutination," *J. Virol. Methods* 2:269-275, Elsevier/North-Holland Biomedical Press (1981).

Kovacsovics-Bankowski, M., et al., "Efficient major histocompatibility complex class I presentation of exogenous antigen upon phagocytosis by macrophages," *Proc. Natl. Acad. Sci. USA* 90:4942-4946, National Academy Press (1993).

Lo, K. K-W., et al., "Surface-modified mutants of cytochrome P450cam: enzymatic properties and electrochemistry," *FEBS Lett.* 451:342-346, Elsevier Science B.V. on behalf of the Federation of European Biochemical Societies (1999).

Minenkova, O.O., et al., "Design of specific immunogens using filamentous phage as the carrier," *Gene* 128:85-88, Elsevier Science Publishers B.V. (1993).

Neurath, A.R., et al., "Hepatitis B Virus surface antigen (HBsAg) as carrier for synthetic peptides having an attached hydrophobic tail," *Mol. Immunol.* 26:53-62, Pergamon Press (1989).

Perham, R.N., et al., "Engineering a peptide epitope display system on filamentous bacteriophage," *FEMS Microbiol. Rev.* 17:25-31, Elsevier Science Publishers on behalf of the Federation of European Microbiological Societies (1995).

Petrenko, V.A., et al., "A library of organic landscapes on filamentous phage," *Protein Engin.* 9:797-801, Oxford University Press (1996).

Pumpens, P. and Grens, E., "Hepatitis B core particles as a universal display model: a structure-function basis for development," *FEBS Lett.* 442:1-6, Elsevier Science B.V. on behalf of the Federation of European Biochemical Societies (1999).

Quash, G., et al., "The preparation of latex particles with covalently bound polyamines IgG and measles agglutinins and their use in visual agglutination tests," *J. Immunol. Methods* 22:165-174, Elsevier/North-Holland Biomedical Press (1978).

Raychaudhuri, S., and Rock, K.L., "Fully mobilizing host defense: Building better vaccines," *Nat. Biotechnol.* 16:1025-1031, Nature America, Inc. (1998).

Redfield, R.R., et al., "Disseminated vaccinia in a military recruit with Human Immunodeficiency Virus (HIV) disease," *N. Eng. J. Med.* 316:673-676, Massachusetts Medical Society (1987).

Rudolf, M.P., et al., Molecular Basis for Nonanaphylactogenicty of a Monoclonal Anti-IgE Antibody, *J. Immunol.* 165:813-819, The American Association of Immunologists (Jul. 2000).

Sedlik, C., et al., "Recombinant parvovirus-like particles as an antigen carrier: A novel nonreplicative exogenous antigen to elicit protective antiviral cytotoxic T cells," *Proc. Natl. Acad. Sci. USA* 94:7503-7508, National Academy Press (1997).

Shen, L., et al., "Recombinant Virus Vaccine-Induced SIV-Specific CD8+ Cytotoxic T Lymphocytes," *Science* 252:440-443, American Association for the Advancement of Science (1991).

Townsend, A., and Bodmer, H., "Antigen recognition by class I-restricted T lymphocytes," *Ann. Rev. Immunol.* 7:601-624, Annual Reviews, Inc. (1989).

VanCott, T.C., et al., "Antibodies with Specificity to Native gp120 and Neutralization Activity against Primary Human Immunodeficiency Virus Type 1 Isolates Elicited by Immunization with Oligomeric gp160," *J. Virol.* 71:4319-4330, American Society for Microbiology (1997).

Watkins, S.J., et al., "The 'adenobody' approach to viral targeting: specific and enhanced adenoviral gene delivery," *Gene Ther.* 4:1004-1012, Stockton Press (1997).

Willis, A.E., et al., "Immunological properties of foreign peptides in multiple display on a filamentous bacteriophage," *Gene* 128:79-83, Elsevier Science Publishers B.V. (1993).

International Preliminary Examination Report for International Application No. PCT/IB99/01925, European Patent Office, Munich (Aug. 2000) (not for publication).

International Search Report for International Application No. PCT/IB99/01925, European Patent Office, Netherlands (Jun. 2000) (not for publication).

NCBI Entrez, GenBank Report, Accession No. P03153, from Seeger, C., et al. (Jan. 1990).

NCBI Entrez, GenBank Report, Accession No. X59397, from Jordan, C.T., et al. (Nov. 1991).

NCBI Entrez, GenBank Report, Accession No. 711678A, from Shipolini, R.A., et al. (Jul. 1992).

NCBI Entrez, GenBank Report, Accession No. M27603, from Orndorff, P.E., and Falkow, S. (Apr. 1993).

NCBI Entrez, GenBank Report, Accession No. M20706, from Nassal M. (Apr. 1993).

NCBI Entrez, GenBank Report, Accession No. AAA37490, from Rouvier E. (Jul. 1993).

NCBI Entrez, GenBank Report, Accession No. M90520, from Kew, M.C., et al. (Aug. 1993).

NCBI Entrez, GenBank Report, Accession No. X00981, from Klemm, P. (Sep. 1993).

NCBI Entrez, GenBank Report, Accession No. VCBPQB, from Maita, T., and Konigsberg, W. (Dec. 1993).

NCBI Entrez, GenBank Report, Accession No. AAA16663, from Kozlovaska, T.M., et al. (Mar. 1994).

NCBI Entrez, GenBank Report, Accession No. X02514, from Yanisch-Perron, C., et al. (May 1994).

NCBI Entrez, GenBank Report, Accession No. X85256, from Lai, M.E., et al. (Apr. 1995).

NCBI Entrez, GenBank Report, Accession No. X85259, from Lai, M.E., et al., (Apr. 1995).

NCBI Entrez, GenBank Report, Accession No. X85260, from Lai, M.E., et al. (Apr. 1995).

NCBI Entrez, GenBank Report, Accession No. X85272, from Lai, M.E., et al. (Apr. 1995).

NCBI Entrez, GenBank Report, Accession No. X85275, from Lai, M.E., et al. (Apr. 1995).

NCBI Entrez, GenBank Report, Accession No. X85284, from Lai, M.E., et al. (Apr. 1995).

NCBI Entrez, GenBank Report, Accession No. X85285, from Lai, M.E., et al. (Apr. 1995).

NCBI Entrez, GenBank Report, Accession No. X85286, from Lai, M.E., et al. (Apr. 1995).

NCBI Entrez, GenBank Report, Accession No. X85287, from Lai, M.E., et al. (Apr. 1995).

NCBI Entrez, GenBank Report, Accession No. X85291, from Lai, M.E., et al. (Apr. 1995).

NCBI Entrez, GenBank Report, Accession No. X85293, from Lai, M.E., et al. (Apr. 1995).

NCBI Entrez, GenBank Report, Accession No. X85295, from Lai, M.E., et al. (Apr. 1995).

NCBI Entrez, GenBank Report, Accession No. X85296, from Lai, M.E., et al. (Apr. 1995).

NCBI Entrez, GenBank Report, Accession No. X85297, from Lai, M.E., et al. (Apr. 1995).

NCBI Entrez, GenBank Report, Accession No. X85298, from Lai, M.E., et al. (Apr. 1995).

NCBI Entrez, GenBank Report, Accession No. X85299, from Lai, M.E., et al. (Apr. 1995).

NCBI Entrez, GenBank Report, Accession No. X85301, from Lai, M.E., et al. (Apr. 1995).

NCBI Entrez, GenBank Report, Accession No. X85302, from Lai, M.E., et al. (Apr. 1995).

NCBI Entrez, GenBank Report, Accession No. X85303, from Lai, M.E., et al. (Apr. 1995).

NCBI Entrez, GenBank Report, Accession No. X85305, from Lai, M.E., et al. (Apr. 1995).

NCBI Entrez, GenBank Report, Accession No. X85307, from Lai, M.E., et al. (Apr. 1995).

NCBI Entrez, GenBank Report, Accession No. X85311, from Lai, M.E., et al. (Apr. 1995).

NCBI Entrez, GenBank Report, Accession No. X85314, from Lai, M.E., et al. (Apr. 1995).

NCBI Entrez, GenBank Report, Accession No. X85315, from Lai, M.E., et al. (Apr. 1995).

NCBI Entrez, GenBank Report, Accession No. X85316, from Lai, M.E., et al. (Apr. 1995).

NCBI Entrez, GenBank Report, Accession No. X85317, from Lai, M.E., et al. (Apr. 1995).

NCBI Entrez, GenBank Report, Accession No. X85319, from Lai, M.E., et al. (Apr. 1995).

NCBI Entrez, GenBank Report, Accession No. X80925, from Karayiannis, P. (Dec. 1995.

NCBI Entrez, GenBank Report, Accession No. AAC50341, from Yao, Z., et al. (Jan. 1996).

NCBI Entrez, GenBank Report, Accession No. X72702, from Preisler-Adams, S., et al. (Feb. 1996).

NCBI Entrez, GenBank Report, Accession No. VCBPR7, from Weber, K., et al. (Apr. 1996).

NCBI Entrez, GenBank Report, Accession No. 1604193A, from Gomez, F., et al. (Oct. 1996).

NCBI Entrez, GenBank Report, Accession No. B56338, from Hoffman, D.R. (May 1997).

NCBI Entrez, GenBank Report, Accession No. U95551, from Rao, B.S., et al. (Jun. 1997).

NCBI Entrez, GenBank Report, Accession No. S14764, from Vandermeers, A., et al. (Oct. 1997).

NCBI Entrez, GenBank Report, Accession No. P03611, from Weber K., et al. (Nov. 1997).

NCBI Entrez, GenBank Report, Accession No. AAC14699, from Beekwilder, M.J., et al. (Apr. 1998).

NCBI Entrez, GenBank Report, Accession No. AAC14704, from Beekwilder, M.J., et al. (Apr. 1998).

NCBI Entrez, GenBank Report, Accession No. AF043593, from Gunther, S., et al. (May 1998).

NCBI Entrez, GenBank Report, Accession No. 1POC, from Scott, D.L., et al. (Sep. 1998).

NCBI Entrez, GenBank Report, Accession No. CAA30374, from Inokuchi, Y., et al. (Feb. 1999).

NCBI Entrez, GenBank Report, Accession No. X02496, from Bichko, V., et al. (Apr. 1999).

NCBI Entrez, GenBank Report, Accession No. MFIV62, from Cox, N.J., et al. (Jul. 1999).

NCBI Entrez, GenBank Report, Accession No. VCBPFR, from Wittmann-Liebold, B., et al. (Jul. 1999).

NCBI Entrez, GenBank Report, Accession No. A59055, from Hoffman, D.R., and Schmidt, J.O. (Aug. 1999).

NCBI Entrez, GenBank Report, Accession No. B59055, from Hoffman, D.R., and Schmidt, J.O. (Aug. 1999).

NCBI Entrez, GenBank Report, Accession No. AF051814, from Boyd E.F., and Hartl, D.L. (Sep. 1999.

NCBI Entrez, GenBank Report, Accession No. AF051815, from Boyd, E.F., and Hartl, D.L. (Sep. 1999).

NCBI Entrez, GenBank Report, Accession No. AF110999, from Chang, S.F., et al. (Oct. 1999).

NCBI Entrez, GenBank Report, Accession No. AB033559, from Okamoto, H., et al. (Oct. 1999).

NCBI Entrez, GenBank Report, Accession No. AB010289, from Koseki, T., et al. (Dec. 1999).

NCBI Entrez, GenBank Report, Accession No. AJ132364, from Graupner, S., et al. (Apr. 2000).

NCBI Entrez, GenBank Report, Accession No. AF237482, from Johnson, J.R., et al. (May 2000).

NCBI Entrez, GenBank Report, Accession No. M32138, from Tong, S.P., et al. (Jul. 2000).

NCBI Entrez, GenBank Report, Accession No. AF229646, from Skerker, J.M., and Shapiro, L. (Aug. 2000).

NCBI Entrez, GenBank Report, Accession No. M95589, from Shi, H., et al. (Jan. 2001).

NCBI Entrez, GenBank Report, Accession No. VCBPM2, from Min Jou, W., et al. (Jan. 2001).

NCBI Entrez, GenBank Report, Accession No. AF323080, from Steppan, C.M., et al. (Jan. 2001).

NCBI Entrez, GenBank Report, Accession No. AF323081, from Steppan, C.M., et al. (Jan. 2001).
NCBI Entrez, GenBank Report, Accession No. U14003, from Plunkett, G., III, et al. (Jan. 2001).
NCBI Entrez, GenBank Report, Accession No. AF121239, from Hannoun, C., et al. (Feb. 2001).
NCBI Entrez, GenBank Report, Accession No. AF121240, from Hannoun, C., et al. (Feb. 2001).
NCBI Entrez, GenBank Report, Accession No. AF121242, from Hannoun, C., et al. (Feb. 2001).
NCBI Entrez, GenBank Report, Accession No. X59795, from Lai, M.E., et al. (Mar. 2001).
NCBI Entrez, GenBank Report, Accession No. X65257, from Lai, M.E., et al. (Mar. 2001).
NCBI Entrez, GenBank Report, Accession No. X65258, from Lai, M.E., et al. (Mar. 2001).
NCBI Entrez, GenBank Report, Accession No. AF151735, from Gerner, P., et al. (Apr. 2001).
NCBI Entrez, GenBank Report, Accession No. AJ000636, from Gousset, N., et al. (Nov. 2001).
NCBI Entrez, GenBank Report, Accession No. AAB59424, from Kenten, J.H., et al. (Feb. 2002).
NCBI Entrez, GenBank Report, Accession No. AAC06250, from Beekwilder, M.J., et al. (Mar. 2002).
NCBI Entrez, GenBank Report, Accession No. L09137, from Yanisch-Perron, C., et al. (May 2002).
NCBI Entrez, GenBank Report, Accession No. O09006, from Hromas, R., et al. (Jun. 2002).
NCBI Entrez, GenBank Report, Accession No. P40224, from Nagasawa, T., et al. (Jun. 2002).
NCBI Entrez, GenBank Report, Accession No. P34884, from Bernhagen, J., et al. (Jun. 2002).
NCBI Entrez, GenBank Report, Accession No. P06821, from Winter, G., et al. (Jun. 2002).
NCBI Entrez, GenBank Report, Accession No. P30904, from Sakai, M., et al. (Jun. 2002).
NCBI Entrez, GenBank Report, Accession No. NP_040754, from Inokuchi, Y., et al. (Jun. 2003).
NCBI Entrez, GenBank Report, Accession No. NP_061354, from Ishikawa, S., et al. (Sep. 2003).
NCBI Entrez, GenBank Report, Accession No. NP_031804, from Lenda, D.M., et al. (Sep. 2003).
NCBI Entrez, GenBank Report, Accession No. NP_006410, from Luther, S.A., et al. (Sep. 2003).
NCBI Entrez, GenBank Report, Accession No. NP_000748, from Yao, G.Q., et al. (Sep. 2003).
NCBI Entrez, GenBank Report, Accession No. P03069, from Hinnebusch, A.G., et al. (Sep. 2003).
NCBI Entrez, GenBank Report, Accession No. O00585, from Hromas, R., et al. (Sep. 2003).
NCBI Entrez, GenBank Report, Accession No. P14174, from Weiser, W.Y., et al. (Sep. 2003).
NCBI Entrez, GenBank Report, Accession No. P48061, from Spotila, L.D., et al. (Sep. 2003).
NCBI Entrez, GenBank Report, Accession No. P80003, from Vandermeers, A., et al. (Sep. 2003).
Swiss-Prot/TrEMBL, TN11_Mouse, Primary Accession No. O35235, entered in Swiss-Prot in Oct. 2001.
Swiss-Prot/TrEMBL, TN11_Human, Primary Accession No. O14788, entered in Swiss-Prot in Oct. 2001.
Co-pending U.S. Appl. No. 10/264,267, inventors Bachmann, M., filed Oct. 4, 2002 (Not Published).
Co-pending U.S. Appl. No. 10/289,456, inventors Bachmann et al., filed Nov. 7, 2002.
Co-pending U.S. Appl. No. 10/617,876, inventors Bachmann et al., filed Jul. 14, 2003.
Co-pending U.S. Appl. No. 10/346,190, inventors Bachmann et al., filed Jan. 17, 2003.
Co-pending U.S. Appl. No. 10/622,087, inventors Bachmann et al., filed Jul. 18, 2003.
Co-pending U.S. Appl. No. 10/622,124, inventors Bachmann et al., filed Jul. 18, 2003.

Abad, A., et al., "Comparison of a Monoclonal Antibody-Based Enzyme-Linked Immunosorbent Assay and Gas Chromatography for the Determination of Nicotine in Cigarette Smoke Condensates," Anal Chem. 65:3227-3231, American Chemical Society (1993).
Bonese, K.F., et al., "Changes in heroin self-administration by a rhesus monkey after morphine immunisation," Nature 252:708-710, Nature Publishing Group (1974).
Byrnes-Blake, K.A., et al., "Generation of anti-(+)methamphetamine antibodies is not impeded by (+)methamphetamine administration during active immunization of rats," Int. Immunopharmacol. 1:329-338, Elsevier (Feb. 2001).
Carpino, L.A., "1-Hydroxy-7-azabenzotriazole. An Efficient Peptide Coupling Additive," J. Am. Chem. Soc. 115:4397-4398, American Chemical Society (1993).
Carrera, M.R., et al., "Suppression of psychoactive effects of cocaine by active immunization," Nature 378:727-730, Nature Publishing Group (1995).
Carrera, M.R., et al., "Cocaine vaccines: Antibody protection against relapse in a rat model," Proc. Natl. Acad. Sci. USA 97:6202-6206, National Academy Press (2000).
Carrera, M.R., et al., "A second-generation vaccine protects against the psychoactive effects of cocaine," Proc. Natl. Acad. Sci. USA 98:1988-1992, National Academy Press (Feb. 2001).
Castaldi, G., et al., "Tartaric Acid, an Efficient Chiral Auxiliary: New Asymmetric Synthesis of 2-Alkyl-2-arylacetic Acids," J. Org. Chem. 52:3018-3027, American Chemical Society (1987).
Castro, A., and Prieto, I., "Nicotine antibody production: comparison of two nicotine conjugates in different animal species," Biochem. Biophys. Res. Commun. 67:583-589, Academic Press (1975).
Castro, A., et al, "Nicotine Antibodies: Comparison of Ligand Specificities of Antibodies Produced against Two Nicotine Conjugates," Eur. J. Biochem. 104:331-340, Blackwell Publishing (1980).
Cohen, C., et al., "SR141716, a central cannabinoid ($CB_1$) receptor antagonist, blocks the motivational and dopamine-releasing effects of nicotine in rats," Behav. Pharmacol. 13:451-463, Lippincott Williams & Wilkins (Sep. 2002).
da Costa, C.L., et al., "Stopping Smoking: A prospective, Randomized, Double-Blind Study Comparing Nortriptyline to Placebo," Chest 122:403-408, The American College of Chest Physicians (Aug. 2002).
Fox, B.S., et al., "Efficacy of a therapeutic cocaine vaccine in rodent models," Nat. Med. 2:1129-1132, Nature Publishing Group (1996).
Hardin, J.S., et al., "Pharmacodynamics of a Monoclonal Antiphencyclidine Fab with Broad Selectivity for Phencyclidine-Like Drugs," J. Pharmacol. Exp. Ther. 285:1113-1122, The American Society for Pharmacology and Experimental Therapeutics (1998).
Hieda, Y., et al., "Vaccination against nicotine during continued nicotine administration in rats: immunogenicity of the vaccine and effects on nicotine distribution to brain," Int. J. Immunopharmacol. 22:809-819, Elsevier Science Ltd. (Oct. 2000).
Hieda, Y., et al., "Active Immunization Alters the Plasma Nicotine Concentration in Rats," J. Pharmacol. Exp. Ther. 283:1076-1081, The American Society for Pharmacology and Experimental Therapeutics (1997).
Hieda, Y., et al., "Immunization of rats reduces nicotine distribution to brain," Psychopharmacology (Berl) 143:150-157, Springer-Verlag (1999).
Hodge, L.M., et al., "Immunoglobulin A (IgA) Responses and IgE-Associated Inflammation along the Respiratory Tract after Mucosal but Not Systemic Immunization," Infect. Immun. 69:2328-2338, American Society for Microbiology (Apr. 2001).
Isomura, S., et al., "An Immunotherapeutic Program for the Treatment of Nicotine Addiction: Hapten Design and Synthesis," J. Org. Chem. 66:4115-4121, American Chemical Society (Jun. 2001).
Jorenby, D.E., et al., "A controlled trial of sustained-release bupropion, a nicotine patch, or both for smoking cessation," N. Engl. J. Med. 340:685-691, Massachusetts Medical Society (1999).
Joseph, A.M., et al., "Lack of Efficacy of Transdermal Nicotine in Smoking Cessation," N. Engl. J. Med. 341:1157-1158, Massachusetts Medical Society (1999).

Killian, A., et al., "Effects of Passive Immunization Against Morphine on Heroin Self-Administration," *Pharmacol. Biochem. Behav.* 9:347-352, ANKHO International Inc. (1978).

Klovins, J., et al., "Nucleotide sequence of a ssRNA phage from *Acinetobacter*: kinship to coliphages," *J. Gen. Virol.* 83:1523-1533, Cambridge University Press (Jun. 2002).

Langone, J.J. & VanVunakis, H., "Radioimmunossay of Nicotine, Cotinine, and γ-(3-Pyridyl)-γ-oxo-N-methylbutyramide," *Methods Enzymol.* 84:628-640, Academic Press (1982).

Langone, J.J., et al., "Nicotine and Its Metabolites, Radioimmunoassays for Nicotine and Cotinine," *Biochemistry* 12:5025-5030, American Chemical Society (1973).

Malin, D.H., et al., "Passive immunization against nicotine prevents nicotine alleviation of nicotine abstinence syndrome," *Pharmacol. Biochem. Behav.* 68:87-92, Elsevier Science (Jan. 2001).

Matsushita, H., et al., "Conjugate of bovine serum albumin with nicotine," *Biochem. Biophys. Res. Commun.* 57:1006-1010, Academic Press, Inc. (1974).

Meijler, M.M., et al., "A New Strategy for Improved Nicotine Vaccines Using Confomationally Constrained Haptens," *J. Am. Chem. Soc.* 125:7164-7165, American Chemical Society (Jun. 2003).

Musso, D.L., et al., "Synthesis and Evaluation of the Antidepressant Activity of the Enantiomers of Bupropion," *Chirality* 5:495-500, Wiley-Liss, Inc. (1993).

Noguchi, M., et al., "Conjugate of nicotine and cotinine to bovine serum albumin," *Biochem. Biophys. Res. Commun.* 83:83-86, Academic Press, Inc. (1978).

Pentel, P.R., et al., "A Nicotine Conjugate Vaccine Reduces Nicotine Distribution to Brain and Attenuates Its Behavioral and Cardiovascular Effects in Rats," *Pharmacol. Biochem. Behav.* 65:191-198, Elsevier Science (Jan. 2000).

Proksch, J.W., et al., "Anti-Phencyclidine Monoclonal Antibodies Provide Long-Term Reductions in Brain Phencyclidine Concentrations during Chronic Phencyclidine Administration in Rats," *J. Pharmacol. Exp. Ther.* 292:831-837, The American Society for Pharmacology and Experimental Therapeutics (Mar. 2000).

Simecka, J.W., et al., "Mucosally Induced Immunoglobulin E-Associated Inflammation in the Respiratory tract," *Infect. Immun.* 68:672-679, American Society for Microbiology (Feb. 2000).

"Sindbis Expression System," Version E, Invitrogen Corporation, Carlsbad, CA, Catalog No. K750-1 (Apr. 2002).

Stoll, E., et al., "Revised Amino Acid Sequence of Qβ Coat Protein between Positions 1 and 60," *J. Biol. Chem.* 252:990-993, The American Society for Biochemistry and Molecular Biology (1977).

Yamamoto, S., et al., "A nontoxic mutant of cholera toxin elicits Th2-type responses for enhanced mucosal immunity," *Proc. Natl. Acad. Sci. USA* 94:5267-5272, National Academy Press (1997).

NCBI Entrez, GenBank Report, Accession No. NP_695026, from Inokuchi et al. (Jul. 2003).

NCBI Entrez, PubMed Abstract, PMID: 2205968, Diallo, A., et al., "Morbillivirus group: genome organization and proteins," *Vet. Microbiol.* 23:155-163 (1990).

Milich, D.R., et al., "The Hepatitis B Virus Core and e Antigens Elicit Different Th Cell Subsets: Antigen Structure Can Affect Th Cell Phenotype," *J. Virol.* 71:2192-2201, American Society for Microbiology (1997).

Milich, D.R., et al., "The Hepatitis Nucleocapsid as a Vaccine Carrier Moiety," *Ann. N.Y. Acad. Sci.* 754:187-201, New York Academy of Sciences (1995).

Curtiss, L. K., et al., "The relative immunodominance of haptenic determinants on a complex hapten phage conjugate," *Immunochemistry* 12:949-957, Pergamon Press, Great Britain (Dec. 1975).

Lechner, F., et al., "Virus-like particles as modular system for novel vaccines," *Intervirology* 45:212-217, S. Karger AG, Basel (Jul.-Dec. 2002).

Pumpens, P., et al., "Evaluation of HBs, HBc, and frCP virus-like particles for expression of human papillomavirus 16 E7 oncoprotein epitopes," *Intervirology* 45:24-32, S. Karger AG, Basel (Jan. 2002).

Dialog File 351, Accession No. 1994-111516, unverified Derwent WPI English language abstract for FR2695563 (Document AM10).

Print out of Xenova Group PLC web page, www.xenova.co.uk/t_addiction.html; accessed Oct. 8, 2004.

Print out of Xenova Group PLC web page, www.xenova.co.uk/dc_ta_nic.html; accessed Oct. 8, 2004.

Print out of Xenova Group PLC web page, www.xenova.co.uk/dc_ta_cd.html; accessed Oct. 8, 2004.

Press release by Xenova Group PLC, accessed at www.xenova.co.uk/PressReleases/pr_20040614_01.html; Jun. 14, 2004.

Press release by Xenova Group PLC, accessed at www.xenova.co.uk/PressReleases/pr_20040714_01.html; Jul. 14, 2004.

Print out of CNN web page "New anti-smoking drugs promising," accessed at www.cnn.com/2005/HEALTH/conditions/03/08/anti-smoking.pill.ap/index.html; Mar. 8, 2005.

Cerny, E. H. et al., "Preclinical Development of a Vaccine 'Against Smoking'," *Onkologie* 25:406-411, S. Karger GmbH, Freiburg (Oct. 2002).

Meijler, M.M. et al., "Development of Immunopharmacotherapy Against Drugs of Abuse," *Current Drug Discovery Technologies*, 1:77-89, Bentham Science Publishers Ltd (2004).

\* cited by examiner

HAPTEN-CARRIER CONJUGATES AND USES THEREOF

CROSS-REFERENCE TO RELATED APPLICATONS

This application is a divisional of U.S. application Ser. No. 10/622,064; and claims benefit of the filing date of U.S. Provisional Application No. 60/396,575, filed Jul. 18, 2002; both of which are entirely incorporated herein by reference.

BACKGROUND OF THE INVENTION

1. Field of the Invention

The present invention is in the fields of medicine, public health, immunology, molecular biology and virology.

2. Related Art

Addictive drug abuse disorders carry with them a number of specific, well recognized sequelae that have both societal and economic consequences. These include death, disease, violence, crime, loss of employment, reduced productivity, relationship and familial breakdown, and the spread of HIV and other sexually transmitted diseases. The economic cost to United States society from drug abuse (excluding tobacco) was an estimated $98 billion in 1992, the last year for which reliable data are available ("The economic costs of alcohol and drug abuse in the United States-1992", National Institute on Drug Abuse). These costs include crime ($59.1 billion), premature death ($14.6 billion), impaired productivity/workplace accidents ($14.2 billion), welfare ($10.4 billion), health care ($5.5 billion), and motor vehicle accidents. These costs are borne primarily by government (46%), drug abusers and their families (44%). It is well recognized that drug abuse remains a serious problem in society. Three years after the 1992 study, in 1995, NIDA estimated drug abuse costs to the society was $110 billion.

The per se use of drugs of abuse can have deleterious effects on the user. However, it is recognized that the addictive nature of these drugs are both central to the problems associated with such drug use, and underlie the inability to treat both addicted individuals and reduce the prevalence of drug addiction in the society.

The most widely used addictive drug in the world is tobacco. Nicotine, an alkaloid derived from tobacco leaves, is the principal addictive component of tobacco. In 1999, 46.5 million adults in the United States were current smokers. Cigarette smoking is the single leading cause of preventable death in the United States. According to the Centers for Disease Control and Prevention (CDC) 430,000 annual deaths are attributable to cigarette smoking in the United States. Lung cancer, coronary heart disease, chronic lung disease, and stroke are the main causes of death. Smoking is not only dangerous to individuals, it also results in staggering societal costs. The estimated smoking-attributable cost for medical care in 1993 was more than $50 billion and the cost of lost productivity and forfeited earnings due to smoking-related disability was estimated at $47 billion per year. Thus, the total economic cost associated with nicotine addiction is greater than the combined costs for all other types of addictive drugs.

Despite recent advances in behavioral and pharmacologic treatments, the vast majority of cigarette smokers who try to quit will fail (for overview see Fiore et al. (2000) Treating tobacco use and dependence, clinical practice guideline, US Department of Health and Human Services, Public Health Service). Nicotine replacement therapy is one currently used medication, either in the form of nicotine gum, inhaler, nasal spray or transdermal patches. The efficacy of transdermal nicotine patches alone has been questioned in a placebo-controlled, double-blinded clinical trial (Joseph et al., *N. Engl. J. Med.* (1999), 340:1157-1158; Jorenby et al., *N. Engl. J. Med.* (1999) 340:685-691). Furthermore, adverse effects of nicotine gum such as mouth irritation, sore jaw muscles, dyspepsia, nausea, hiccups and paresthesia and itching, erythema, sleep disturbances, gastrointestinal problems, somnolence, nervousness, dizziness and sweating for the nicotine patch were observed. A treatment with the antidepressant bupropion can increase the abstinence rates at 12 months to about 30% (Jorenby et al., supra).

Novel approaches to the treatment and prevention of addiction, to nicotine and to other drugs, are clearly needed. Immunization strategies to modify the behavioral effects of drugs have been the subject of investigation since 1974. Both active immunization with morphine-6-hemisuccinate-BSA and passive immunization with the resultant antibodies reduced heroin self administration in rhesus monkeys (Bonese, et al. *Nature* 252:708-710 (1974); Killian, et al *Pharmacol. Biochem. Behav.* 9:347-352 (1978).) Immunization has also proven effective against cocaine addiction. Active immunization reduced the effect of subsequent cocaine administration in rats (Carrera et al *Nature* 379:727-730 (1995), and both active and passive immunization was demonstrated to abolish self administration (Fox et al. *Nature Med* 2:1129-1132 (1996)). More recently, immunization with GNC-KLH conjugate abolished self administration in cocaine-addicted rats (Carrera et al *Proc. Nat. Acad Sci USA* 97:6202-62061992 (2000)) and both immunization with GND-KLH conjugate or transfer of anti-cocaine monoclonal antibodies blocked cocaine effects (Carrera et al *Proc. Nat. Acad Sci USA* 98:1988-1992 (2001).

Antibodies have been raised against phencyclidine (PCP) and show effectiveness in reducing PCP levels in the brain, reducing behavioral effects, and show similar abilities to block the physiologic effects of PCP analogs (Hardin et al. *J Pharmacol Exp Ther* 285:1113-1122 (1998); Proksch et al. *J. Pharmacol Exp Ther.* 292:831-837 (2000)). Antibodies have also been successfully raised against methamphetamine in rats (Byrnes-Blake et al. *Int Immunopharmacol* 1:329-338 (2001)). U.S. Pat. No. 5,256,409 discloses a vaccine comprising a carrier protein bound to one hapten from the desipramine/imipramine class of drugs and another hapten from the nortriptyline/amitriptyline class of drugs.

Therefore, immune responses can be raised against drugs, the antibodies can block drug action, and animal models have demonstrated that vaccination is effective as a general approach to the treatment of drug abuse and addiction. It is believed that generating an immune response should block the actions of the drug by preventing it from entering the central nervous system (Carrera et al *Nature* 379:727-730 (1995). By reducing the rewards associated with drug use, the addicted individual is no longer motivated to consume the drug.

As the addictive effect of the drugs is caused by their action in the brain, antibodies in serum should be able to reduce drug delivery to brain. Cerny (WO 92/03163) described a vaccine and immunoserum for use against drugs of abuse. The vaccine consisted of a hapten bound to a carrier protein. Also disclosed therein was the production of antibodies against drugs, and the use of these antibodies in the detoxification of one who has taken the drug.

Nicotine, cocaine, heroin and most drugs of abuse are haptens, which are not immunogenic. Coupling of haptens to protein carriers typically enhances their immunogenicity.

Several different nicotine haptens, carriers and methods of coupling have been described. Matsushita et al. (Biochem.

Biophys. Res. Comm. (1974) 57, 1006-1010) and Castro et al. (Eur. J. Biochem. (1980) 104, 331-340) prepared nicotine haptens conjugated to bovine serum albumin (BSA) via a linker at the 6-position of the nicotine. Elsewhere, Castro et al. (Biochem. Biophys. Res. Commun. (1975) 67, 583-589) disclosed two nicotine albumin conjugates: N-succinyl-6-amino-(+/−)-nicotine-BSA and 6-(sigma-aminocapramido)-(+/−)-nicotine-BSA. Noguchi et al. (Biochem. Biophys. Res. Comm. (1978) 83, 83-86) prepared a nicotine-BSA conjugate with nicotine conjugated at the 1-position of the nicotine. Langone et al. (Biochemistry (1973) 12, 5025-5030 and Meth. Enzymol. (1982) 84, 628-640) prepared the hapten derivative O-succinyl-3'-hydroxymethyl-nicotine and conjugated it to bovine serum albumin and keyhole limpet hemocyanin. According to the procedures of Langone et al. (supra), Abad et al. (Anal. Chem. (1993) 65, 3227-3231) synthesized the nicotine hapten 3'-(hydroxymethyl)-nicotine hemisuccinate and coupled it to bovine serum albumin for immunization of mice to produce monoclonal antibodies to nicotine. Isomura et al. (J. Org. Chem. (2001) 66, 4115-4121) provided methods to synthesize nicotine conjugates linked to the 1'-position of nicotine, which were coupled to keyhole limpet hemocyanin (KLH) and BSA. The conjugate to KLH was used to immunize mice and to produce monoclonal antibodies against nicotine. Svensson et al. (WO 99/61054) disclosed nicotine-haptens conjugated via the pyridine ring and further disclosed a nicotine-hapten conjugated to KLH and the induction of nicotine-specific IgG antibodies using such conjugates. When administered in the presence of complete Freund's adjuvant, nicotine-specific ELISA titres of 1:3000 to 1:15500 were measured, while in the absence of Freund's adjuvant titres of 1:500 to 1:3000 were detected. Ennifar et al. (U.S. Pat. No. 6,232,082) disclosed nicotine haptens coupled via the pyrrolidine ring and disclosed a nicotine-hapten conjugated to recombinant *Psuedomonas aeruginosa* exotoxin A (rEPA) and the induction of nicotine-specific IgG antibodies when the conjugates were administered in the presence of complete Freund's adjuvant. Swain et al. (U.S. Pat. No. 5,876,727) disclosed the coupling of a nicotine hapten to BSA and the induction of nicotine-specific IgG antibodies in mice when the conjugates were given in a mixture with complete Freund's adjuvant.

The feasability of a vaccination against nicotine has been shown in principle (Hieda et al., *J. Pharm. Exp. Ther.* (1997) 283, 1076-1081; Hieda et al., *Psychopharm.* (1999), 143, 150-157; Hieda et al., *Int. J. Immunopharm.* (2000) 22, 809-819; Pentel et al., *Pharm. Biochem. Behav.* (2000), 65, 191-198, Malin et al, *Pharm. Biochem. Behav.* (2001), 68, 87-92). Covalent conjugates of nicotine with KLH or rEPA were produced and injected into mice or rats in the presence of complete Freund's adjuvant, and induced nicotine-specific IgG antibodies. Vaccine efficacy was demonstrated by several different ways. After challenge with nicotine, more nicotine remained bound in serum and nicotine concentrations were lower in the brain in the nicotine-KLH or nicotine-rEPA immunized groups of rats compared to the control group immunized with carrier alone. Immunization also reduced the psychopharmacological activity associated with nicotine, as immunized animals were also less susceptible to the effect of nicotine on locomoter activity, dopamine release (Svensson et al. WO 99/61054) and relief of nicotine withdrawal symptoms.

The above art demonstrates the efficacy of vaccine compositions containing complete Freund's adjuvant to induce immune responses against nicotine. Complete Freund's adjuvant is one of the most potents adjuvants available, however because of its side effects its use is not approved for humans. Therefore, there exists a need for vaccine compositions able to induce strong immune responses against nicotine without the use of complete Freund's adjuvant. Further, while BSA has been used successfully as a carrier in animal models it may not be appropriate for use in human vaccine compositions because of the risk of adverse reactions such as the risk of transmitting prion disease (variant Creutzfeldt-Jakob disease). A further challenge to the development of an effective vaccine against nicotine is the need for an immune response able to rapidly decrease nicotine available for absorption by the brain. Nicotine from cigarettes is taken up by mucosal surfaces especially in the mouth and lungs and transported via the blood to the brain. If nicotine-specific antibodies are to be successful in reducing nicotine delivery to brain, they will have to overcome the very high arterial nicotine concentration that is presented to brain within seconds of inhalation (Hieda et al., 1999, supra). Therefore, high concentrations of nicotine-specific antibodies in the blood, which are mainly of the IgG subtype are needed. In mucosal surfaces IgA antibodies are the primary subtype. Accordingly, in addition to the antibodies in blood, nicotine-specific antibodies of the IgA subtype in the lung would be beneficial for neutralizing nicotine inhaled during smoking before it begins circulating in the blood.

Cholera toxin, a known carrier protein in the art, can induce IgA antibodies, in particular after intranasal administration. Cholera toxin can also act as an adjuvant, eliminating the need for complete Freund's adjuvant in a vaccine composition. However, when cholera toxin is administered as a mucosal adjuvant it stimulates a predominantly $T_H2$-type immune response with increased interleukin-4 levels and associated increments in total and specific IgE antibody levels (Yamamoto et al., (1997) Proc. Natl. Acad. Sci USA 94, 5267-5272). After nasal immunization in the presence of cholera toxin, IgE-associated inflammatory reactions developed within the lungs of mice (Simecka et al., (2000) Infect. Immunol. 68, 672-679, Hodge et al., (2001) Infect. Immunol., 69, 2328-2338). Despite the promise of intranasal immunization in the presence of cholera toxin, there is also the potential to develop adverse immunopathological reactions characterized by pulmonary airway inflammation (Hodge et al., (2001) Infect. Immunol., 69, 2328-2338).

Therefore, there exists a need for carrier systems able to stimulate immune responses against hapten without the use of toxic adjuvants, without the use of poorly tolerated carrier proteins and, in certain situations, without stimulation of potentially pathologic $T_H2$ immune responses. Novel carrier systems meeting these specifications can be used towards the formation of novel conjugates and compositions suitable for the treatment of addiction, among other conditions, for which there is currently an urgent need.

BRIEF SUMMARY OF THE INVENTION

We have found that haptens attached to core particles leading to highly ordered and repetitive hapten arrays are surprisingly effective in inducing immune responses, particularly antibodies, against haptens. Core particles, containing a first attachment site, and haptens, containing a second attachment site, are linked through said first and second attachment sites to form said ordered and repetitive hapten arrays. The interaction between first and second sites may be direct, or may involve at least one other molecule, e.g. a linker.

In one embodiment, the first attachment site naturally occurs in the core particle. Alternatively, the first attachment site is added by chemical coupling or by recombinant techniques. Preferred first attachment sites comprise amino groups, carboxyl groups or sulfhydryl groups. Preferred amino acids comprising a first attachment site are selected from lysine, arginine, cysteine, aspartate, glutamate tyrosine and histidine. Particularly preferred are lysine residues.

Suitable second attachment sites on haptens are amine, amide, carboxyl and sulfhydryl groups. There is a wide range of compounds that have been developed to enable crosslinking of peptides/proteins or conjugation of protein to derivatized molecules, by forming a covalent bond with a reactive group of a protein molecule of the core particle.

Core particles with a first attachment site of the invention include any particle suitable for the formation of ordered repetitive arrays. In some embodiments such core particles include virus-like particles (VLPs), bacteriophage, bacteriophage virus like particles, pili, and the like. In certain embodiments these are HbcAg VLPs, bacteriophage VLP and type I pili. The invention also provides variant forms of the core particles that remain able to form ordered repetitive structure. Variant forms include recombinant and natural forms, and mutant forms of core particles. In certain embodiments, the mutant forms of the core particle include those where the type of first attachment site, or number of said sites, differ from the parent. Alteration of the number of lysine residues on the core particle are particularly preferred.

In certain embodiments, conjugates of the invention comprise haptens suitable for inducing immune responses against a variety of molecules, including but not limited to toxins, hormones and drugs. More preferred are drugs, and yet more preferred are drugs of abuse or addictive drugs. Haptens of the invention contain a second attachment site for linkage to the first attachment site of the core particle, either directly or via at least one linking molecule. In one embodiment, the hapten is suitable for inducing immune responses against cocaine, for example succinylated norcocaine.

Preferred embodiments of the invention are nicotine-hapten conjugates. Nicotine haptens suitable for the conjugates of the present invention can have at least one, preferably one, side chain bonded to any position on either the pyridine or the pyrrolidine ring of the nicotine. Those skilled in the art know how to produce suitable derivatives of nicotine haptens. For example, nicotine may be chemically derivatized at the 3' position to provide an hydroxyl residue that is suitable for reaction with reagents such as succinic anhydride to form O-succinyl-3'-hydroxymethyl-nicotine. This nicotine derivative may be coupled to amino acids of the core particle, such as lysine, using the activation reagent EDC. In a further preferred embodiment the O-succinyl-3'-hydroxymethyl-nicotine can be activated with EDC and the resulting activated carboxylic group is stabilized by N-hydroxysuccinimide. In other embodiments, haptens are produced by acylation of nornicotine with succinic anhydride in methylene chloride in the presence of two equivalents of diisopropylethylamine. Such a nicotine hapten is then coupled to core particles of present invention with an activating reagent e.g. HATU. Other methods and processes for synthesizing haptens suitable for conjugates and compositions or the invention are provided.

The present invention provides compositions comprising a core particle and a hapten, suitable for use in inducing immune responses. Compositions of the invention include vaccine compositions, with or without additional pharmaceutically acceptable excipients or adjuvants. Methods for immunization are provided. More preferred is intranasal immunization.

Compositions of the invention induce immune responses, including the production of antibodies. Therefore, in another embodiment, the invention provides methods of producing said antibodies against such haptens. Such antibodies of the invention are useful in treatment or prevention of diseases and for the detection of haptens, for example in the methods of diagnosing diseases or diseases associated with the presence of one or more haptens in the tissues or circulation of an animal.

In a related embodiment, the invention is useful for the prevention or treatment of diseases, disorders or conditions which include, but are not limited to, poisoning by toxins, disregulation of hormone levels, drug intoxication, or drug addiction and the like. Immunization with the hapten-carrier conjugates of the invention results in an immune response against the hapten, such that immune molecules, particularly antibodies, bind the hapten. Passive transfer of antibodies is also useful for the treatment and prevention of diseases. Treatment of addiction is also useful in the treatment of other diseases and conditions associated with addiction.

We have found that nicotine-hapten conjugates attached to virus-like particles induce high nicotine-specific IgG antibodies. The present invention therefore provides a therapeutic for nicotine addiction, which is based on an ordered and repetitive VLP-nicotine conjugate. This therapeutic is able to induce high titers of anti-nicotine antibodies in a vaccinated animal. High antibody titers are induced even in the absence of adjuvants and encompass not only IgG but also IgA subtypes. Furthermore, this therapeutic is, surprisingly, not associated with induction of potentially pathologic immune responses such as inflammation. Therapeutic compositions of the invention comprise at least one nicotine hapten molecule and a VLP, or at least one nicotine hapten and an alternative core particle such as HbcAg or pili.

Thus, the invention embodies methods of treatment and prevention comprising the use of the conjugates and compositions of the invention. Such methods are useful in the therapy and prophylaxis of diseases, disorders and conditions associated with drugs, hormones and toxins.

In a further embodiment of the invention, a pharmaceutical composition is provided for treating nicotine addiction, palliating nicotine withdrawal symptoms, facilitating smoking cessation or preventing relapse comprising a therapeutically effective combination of the vaccine composition of the invention and an additional agent. In one embodiment, the additional agent is selected from the group consisting of: anti-depressant; nicotine receptor modulator; cannabinoid receptor antagonist; opioid receptor antagonist; monoamine oxidase inhibitor; anxiolytic or any combination of these agents.

Other embodiments of the invention are kits suitable for diagnosis and screening that utilize the conjugates, compositions and methods of the present invention. Other embodiments of the present invention will be apparent to one of ordinary skill in light of what is known in the art, the following drawings and description of the invention, and the claims.

DETAILED DESCRIPTION OF THE INVENTION

Figure 1:
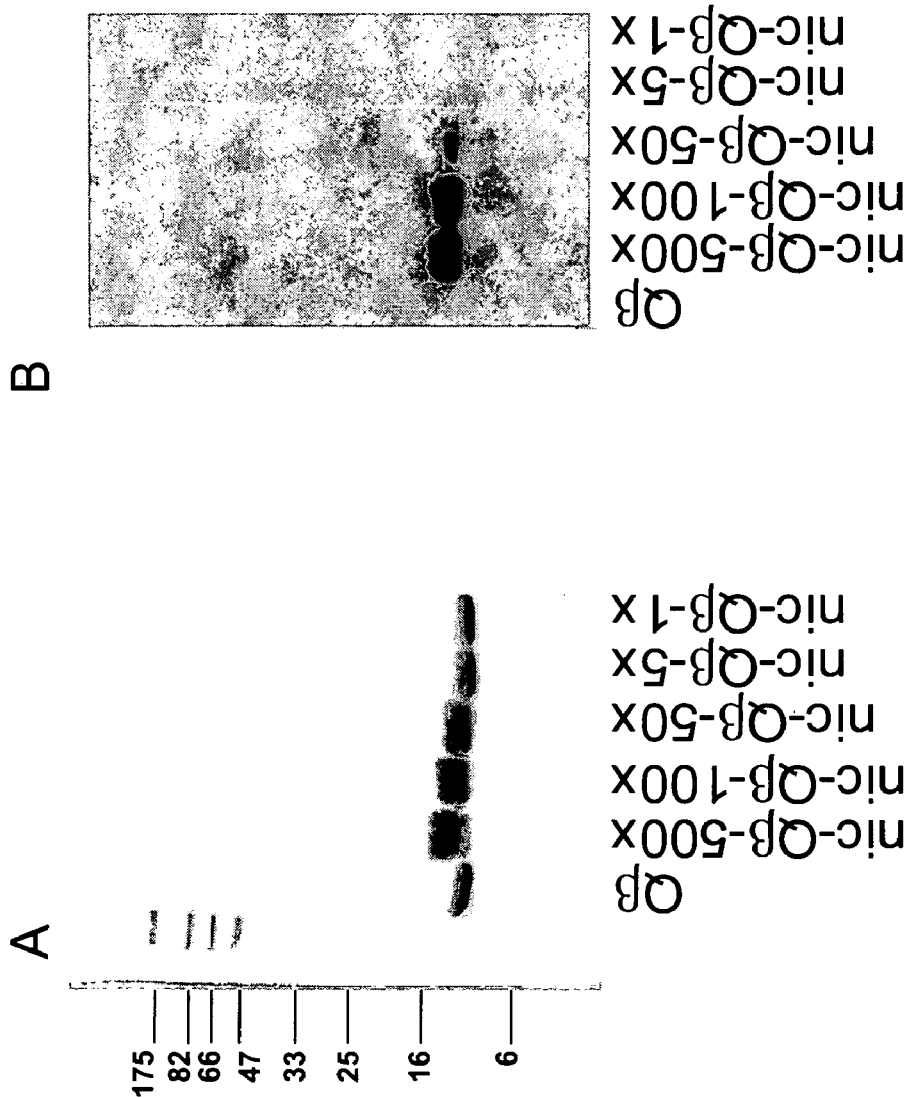
FIGS. 1A and B depict SDS-PAGE and Westernblot analysis of Nic-Qβ conjugates. The nicotine derivate Suc-Nic was coupled to Qβ at different concentrations (1×, 5×, 50×, 100×, and 500× molar excess). Aliquots of the reaction solutions were loaded on a 16% SDS-PAGE gel and stained with Coomassie Blue (A). From a gel run in parallel, proteins were transferred onto nitrocellulose and detected with an antiserum raised against nicotine-cholera toxin followed by a HRPO-conjugated goat anti-mouse IgG and ECL detection (B). Molecular weight markers are given on the left margin.
Figure 2:
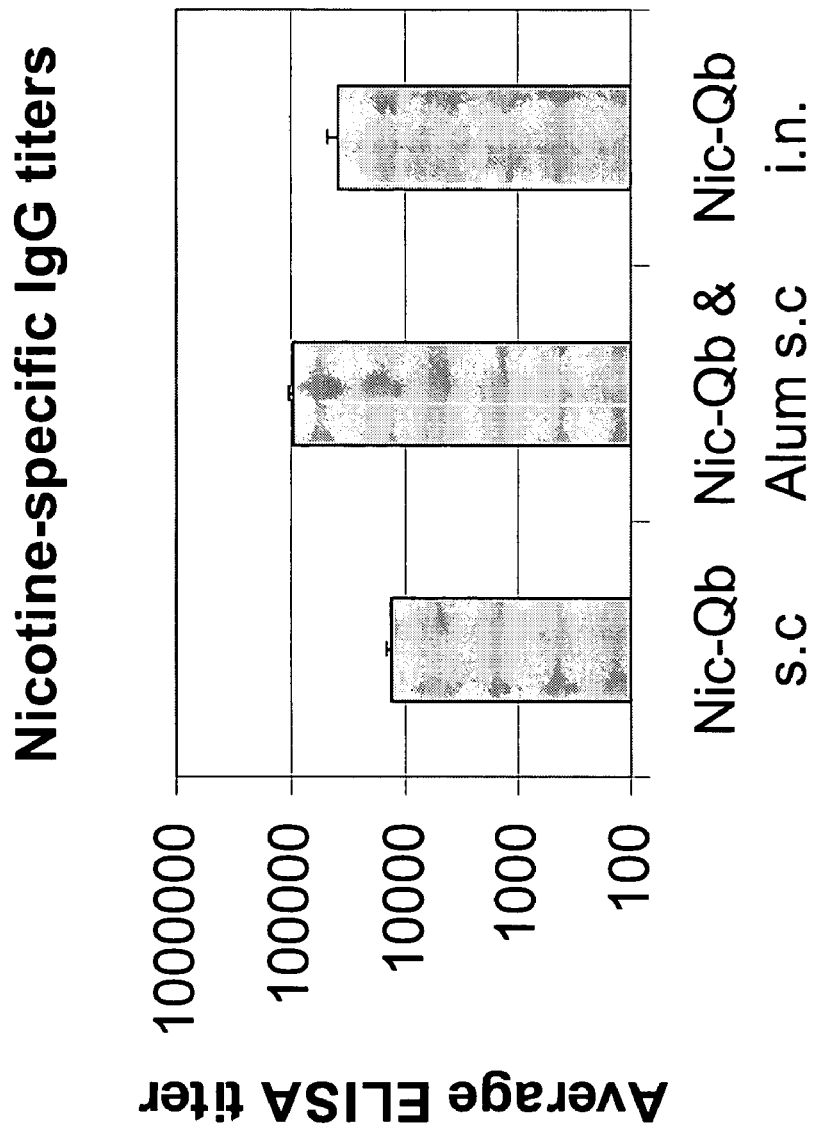
FIG. 2 depicts Nicotine-specific IgG antibodies and IgG titer. Sera from vaccinated mice were tested for reactivity against nicotine coupled to BSA by ELISA. Optical densities at 450 nm obtained for each serum dilution are shown (A). Titers were calculated from the dilution that gives half-maximal optical density (B). Average of three mice in each group are shown.

It is to be understood that both the foregoing general description and the following detailed description are exemplary and explanatory only and are intended to provide further explanation of the invention as claimed.

Definitions

The following definitions are summaries of concepts commonly understood by one of ordinary skill in the relevant art and are provided for the purposes of comprehension of the following invention but are not meant to be a limitation of the invention.

Adjuvant: The term "adjuvant" as used herein refers to non-specific stimulators of the immune response or substances that allow generation of a depot in the host which when combined with the vaccine and pharmaceutical composition, respectively, of the present invention may provide for an even more enhanced immune response. A variety of adjuvants can be used. Examples include complete and incomplete Freund's adjuvant, aluminum hydroxide and modified muramyldipeptide. Further adjuvants are mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art. Further adjuvants that can be administered with the compositions of the invention include, but are not limited to, Monophosphoryl lipid immunomodulator, AdjuVax 100a, QS-21, QS-18, CRL1005, Aluminum salts (Alum), MF-59, OM-174, OM-197, OM-294, and Virosomal adjuvant technology. The adjuvants can also comprise a mixture of these substances.

Immunologically active saponin fractions having adjuvant activity derived from the bark of the South American tree Quillaja Saponaria Molina are known in the art. For example QS21, also known as QA21, is an Hp1c purified fraction from the Quillaja Saponaria Molina tree and it's method of its production is disclosed (as QA21) in U.S. Pat. No. 5,057,540. Quillaja saponin has also been disclosed as an adjuvant by Scott et al, Int. Archs. Allergy Appl. Immun., 1985, 77, 409. Monosphoryl lipid A and derivatives thereof are known in the art. A preferred derivative is 3 de-o-acylated monophosphoryl lipid A. Further preferred adjuvants are described in WO00/00462, the disclosure of which is herein incorporated by reference.

However, an advantageous feature of the present invention is the high immunogenicty of the inventive compositions. As already outlined herein or will become apparent as this specification proceeds, vaccines and pharmaceutical compositions devoid of adjuvants are provided, in further alternative or preferred embodiments, leading to vaccines and pharmaceutical compositions for treating drug addiction, preferably nicotine addiction, being devoid of adjuvants and, thus, having a superior safety profile since adjuvants may cause side-effects. The term "devoid" as used herein in the context of vaccines and pharmaceutical compositions for treating drug addiction, preferably nicotine addiction, refers to vaccines and pharmaceutical compositions that are used without adjuvants.

Animal: As used herein, the term "animal" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

Antibody: As used herein, the term "antibody" refers to molecules which are capable of binding an epitope or antigenic determinant. The term is meant to include whole antibodies and antigen-binding fragments thereof, including single-chain antibodies. Most preferably the antibodies are human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies can be from any animal origin including birds and mammals. Preferably, the antibodies are mammalian e.g. human, murine, rabbit, goat, guinea pig, camel, horse and the like, or other suitable animals e.g. chicken. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598, the disclosure of which is incorporated herein by reference in its entirety.

Active immunization: As used herein, the term "active immunization" refers to the induction of an immune response in an individual, typically an animal, elicited by the administration of an immunogen, vaccine, antigen or hapten-carrier conjugate. By contrast, passive immunization refers to the conferral of immunity in an individual by the transfer of immune molecules or cells into said individual.

Alphavirus: As used herein, the term "alphavirus" refers to any of the RNA viruses included within the genus *Alphavirus*. Descriptions of the members of this genus are contained in Strauss and Strauss, *Microbiol. Rev.*, 58:491-562 (1994). Examples of alphaviruses include Aura virus, Bebaru virus, Cabassou virus, Chikungunya virus, Easter equine encephalomyelitis virus, Fort morgan virus, Getah virus, Kyzylagach virus, Mayoaro virus, Middleburg virus, Mucambo virus, Ndumu virus, Pixuna virus, Tonate virus, Triniti virus, Una virus, Western equine encephalomyelitis virus, Whataroa virus, Sindbis virus (SIN), Semliki forest virus (SFV), Venezuelan equine encephalomyelitis virus (VEE), and Ross River virus.

Antigen: As used herein, the term "antigen" refers to a molecule capable of being bound by an antibody. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and/or T-cell epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

Antigenic determinant: As used herein, the term "antigenic determinant" is meant to refer to that portion of an antigen that is specifically recognized by either B- or T-lymphocytes. B-lymphocytes responding to antigenic determinants produce antibodies, whereas T-lymphocytes respond to antigenic determinants by proliferation and establishment of effector functions critical for the mediation of cellular and/or humoral immunity.

Association: As used herein, the term "association" as it applies to the first and second attachment sites, refers to the binding of the first and second attachment sites that is preferably by way of at least one non-peptide bond. The nature of the association may be covalent, ionic, hydrophobic, polar or any combination thereof, preferably the nature of the association is covalent.

Attachment Site, First: As used herein, the phrase "first attachment site" refers to an element of the core particle to which the second attachment site located on the antigen or antigenic determinant may associate. The first attachment site may be a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. Multiple first attachment sites are present on the surface of the non-natural molecular scaffold in a repetitive configuration.

Attachment Site, Second: As used herein, the phrase “second attachment site” refers to an element associated with the hapten to which the first attachment site on the surface of the non-natural molecular scaffold may associate. The second attachment site of the hapten comprises any chemical moiety, preferably a amine, an amide, a carboxyl, a sulfhydryl, hydroxyl, aldehyde, acylhalogenide, hydrazine, diazonium, or hydrazide, or further chemical moieties able to specifically react with the first attachment site. Moreover, the second attachment site may comprise a polypeptide, a peptide, a sugar, a polynucleotide, a natural or synthetic polymer, a secondary metabolite or compound (biotin, fluorescein, retinol, digoxigenin, metal ions, phenylmethylsulfonylfluoride), a combination thereof, or a chemically reactive group thereof. At least one second attachment site is present on the hapten. The term “hapten” with at least one second attachment site” refers, therefore, to a hapten construct comprising at least the hapten and the second attachment site. However, in particular for a second attachment site, which is not naturally occurring within the hapten, these haptens comprise a linker which associates the hapten with the second attachment site, or more preferably, already comprises or contains the second attachment site.

Bound: As used herein, the term “bound” refers to binding or attachment that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term “bound” is broader than and includes terms such as “coupled,” “fused” and “attached”.

Core particle: As used herein, the term “core particle” refers to a rigid structure with an inherent repetitive organization that provides a foundation for attachment of the first attachment site. A core particle as used herein may be the product of a synthetic process or the product of a biological process.

Coat protein(s): As used herein, the term “coat protein(s)” refers to the protein(s) of a bacteriophage or a RNA-phage capable of being incorporated within the capsid assembly of the bacteriophage or the RNA-phage. However, when referring to the specific gene product of the coat protein gene of RNA-phages the term “CP” is used. For example, the specific gene product of the coat protein gene of RNA-phage Qβ is referred to as “Qβ CP”, whereas the “coat proteins” of bacteriophage Qb comprise the “Qβ CP” as well as the accessory A1 protein. The capsid of Bacteriophage Qβ is composed mainly of the Qβ CP, with a minor content of the A1 protein. Likewise, the VLP Qβ coat protein contains mainly Qβ CP, with a minor content of A1 protein.

Conjugate: As used herein, the noun “conjugate” refers to the product of conjugation between one or more of (a) a core particle such as VLP, and one or more of (b) an organic molecule, hapten, antigen or antigenic determinant as described elsewhere herein, wherein the elements (a) and (b) are bound to each other.

Composition: As used herein, the term “composition” refers to a product of mixing or combining various elements or ingredients.

Disease, disorder, condition: As used herein, the terms “disease” or “disorder” refer to any adverse condition of an individual including tumors, cancer, allergies, addiction, autoimmunity, poisoning or impairment of optimal mental or bodily function. “Conditions” as used herein includes diseases and disorders but also refers to physiologic states. For example, fertility is a physiologic state but not a disease or disorder. Compositions of the invention suitable for preventing pregnancy by decreasing fertility would therefore be described as a treatment of a condition (fertility), but not a treatment of a disorder or disease. Other conditions are understood by those of ordinary skill in the art.

Effective Amount: As used herein, the term “effective amount” refers to an amount necessary or sufficient to realize a desired biologic effect. An effective amount of the composition would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with “sufficient amount.”

The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

Epitope: As used herein, the term "epitope" refers to basic element or smallest unit of recognition by an individual antibody or T-cell receptor, and thus the particular domain, region or molecular structure to which said antibody or T-cell receptor binds. An antigen may consist of numerous epitopes while a hapten, typically, may possess few epitopes.

Fusion: As used herein, the term "fusion" refers to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

Hapten: As used herein, the term "hapten" refers to a low-molecular weight organic compound that is not capable of eliciting an immune response by itself but will elicit an immune response once attached to a carrier molecule. Exemplary haptens used in conjugates, compositions and methods of the invention include drugs, hormones and toxins, but are not limited to these specific haptens.

Heterologous sequence: As used herein, the term "heterologous sequence" refers to a second sequence of nucleic acid or protein that is not normally found with said nucleic acid or protein and is, usually, artificially added to the sequence in order to confer particular properties. In one example, heterologous amino acids may be added to recombinant capsid proteins for the purposes of purification of the protein, or to serve as a first attachment site.

Isolated: As used herein, when the term "isolated" is used in reference to a molecule, the term means that the molecule has been removed from its native environment. For example, a polynucleotide or a polypeptide naturally present in a living animal is not "isolated," but the same polynucleotide or polypeptide separated from the coexisting materials of its natural state is "isolated." Further, recombinant DNA molecules contained in a vector are considered isolated for the purposes of the present invention. Isolated RNA molecules include in vivo or in vitro RNA replication products of DNA and RNA molecules. Isolated nucleic acid molecules further include synthetically produced molecules. Additionally, vector molecules contained in recombinant host cells are also isolated. Thus, not all "isolated" molecules need be "purified."

Immune response: As used herein, the term "immune response" refers to a humoral immune response and/or cellular immune response leading to the activation or proliferation of B- and/or T-lymphocytes and/or and antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant. Preferably, antigen presenting cell may be activated.

A substance which "enhances" an immune response refers to a substance in which an immune response is observed that is greater or intensified or deviated in any way with the addition of the substance when compared to the same immune response measured without the addition of the substance. For example, the lytic activity of cytotoxic T cells can be measured, e.g. using a $^{51}$Cr release assay, in samples obtained with and without the use of the substance during immunization. The amount of the substance at which the CTL lytic activity is enhanced as compared to the CTL lytic activity without the substance is said to be an amount sufficient to enhance the immune response of the animal to the antigen. In a preferred embodiment, the immune response in enhanced by a factor of at least about 2, more preferably by a factor of about 3 or more. The amount or type of cytokines secreted may also be altered. Alternatively, the amount of antibodies induced or their subclasses may be altered.

Immunization: As used herein, the terms "immunize" or "immunization" or related terms refer to conferring the ability to mount a substantial immune response (comprising antibodies and/or cellular immunity such as effector CTL) against a target antigen or epitope. These terms do not require that complete immunity be created, but rather that an immune response be produced which is substantially greater than baseline. For example, a mammal may be considered to be immunized against a target antigen if the cellular and/or humoral immune response to the target antigen occurs following the application of methods of the invention.

Immunotherapeutic: As used herein, the term "immunotherapeutic" refers to a composition for the treatment of diseases, disorders or conditions. More specifically, the term is used to refer to a method of treatment wherein a beneficial immune response is generated by vaccination or by transfer of immune molecules.

Immunologically effective amount: As used herein, the term "immunologically effective amount" refers to an amount of a composition sufficient to induce an immune response in an individual when introduced into that individual. In the context of active immunization, the term is synonymous with "immunogenically effective amount." The amount of a composition necessary to be immunologically effective varies according many factors including to the composition, the presence of other components in the composition (e.g. adjuvants), the antigen, the route of immunization, the individual, the prior immune or physiologic state etc.

Individual: As used herein, the term "individual" refers to multicellular organisms and includes both plants and animals. Preferred multicellular organisms are animals, more preferred are vertebrates, even more preferred are mammals, and most preferred are humans.

Low or undetectable: As used herein, the phrase "low or undetectable," when used in reference to gene expression level, refers to a level of expression which is either significantly lower than that seen when the gene is maximally induced (e.g., at least five fold lower) or is not readily detectable by the methods used in the following examples section.

Lectin: As used herein, proteins obtained particularly from the seeds of leguminous plants, but also from many other plant and animal sources, that have binding sites for specific mono- or oligosaccharides. Examples include concanavalin A and wheat-germ agglutinin, which are widely used as analytical and preparative agents in the study of glycoprotein.

Natural origin: As used herein, the term "natural origin" means that the whole or parts thereof are not synthetic and exist or are produced in nature.

Non-natural: As used herein, the term generally means not from nature, more specifically, the term means from the hand of man.

Non-natural origin: As used herein, the term "non-natural origin" generally means synthetic or not from nature; more specifically, the term means from the hand of man.

Non-natural molecular scaffold: As used herein, the phrase "non-natural molecular scaffold" refers to any product made by the hand of man that serves to provide a rigid and repetitive array of first attachment sites. Ideally but not necessarily, these first attachment sites are in a geometric order. The non-natural molecular scaffold may be organic or non-organic and may be synthesized chemically or through a biological process, in part or in whole. The non-natural molecular scaffold is comprised of: (a) a core particle, either of natural or non-natural origin; and (b) at least one first attachment site that is connected to a core particle by at least one covalent bond. In a particular embodiment, the non-natural molecular scaffold may be a virus, virus-like particle, a bacterial pilus, a virus capsid particle, a phage, a recombinant form thereof, or synthetic particle.

Nicotine hapten: The term "nicotine hapten" as used in the present invention refers to nicotine, either in its enantiomerically pure (S)- or (R)-form or a mixture thereof, which could be derivatized in such manner as to contain at least one second attachment site which, then, is capable of associating with the first attachment site of the carrier either directly, or via a cross-linker. Preferably, the nicotine hapten is derivatized in such manner as to contain only one second attachment site. This derivatization further increases the order and repetitiveness of the nicotine hapten-carrier conjugate and ensures a directed and controlled coupling of the nicotine hapten to the carrier.

Ordered and repetitive antigen or antigenic determinant array: As used herein, the term "ordered and repetitive antigen or antigenic determinant array" generally refers to a repeating pattern of antigen or antigenic determinant, characterized by a uniform spacial arrangement of the antigens or antigenic determinants with respect to the non-natural molecular scaffold. In one embodiment of the invention, the repeating pattern may be a geometric pattern. Typical and preferred examples of suitable ordered and repetitive antigen or antigenic determinant arrays are those which possess strictly repetitive paracrystalline orders of antigens or antigenic determinants, preferably with spacings of 0.5 to 30 nanometers, more preferably with spacings of 5 to 15 nanometers.

Passive immunization: as used herein, the term "passive immunization" refers to conferral of immunity by the administration, by any route, of exogenously produced immune molecules (e.g. antibodies) or cells (e.g. T-cells) into an animal. Passive immunization differs from "active" immunization, where immunity is obtained by introduction of an immunogen, vaccine, antigen or hapten-carrier conjugate into an individual to elicit an immune response.

Pili: As used herein, the term "pili" (singular being "pilus") refers to extracellular structures of bacterial cells composed of protein monomers (e.g., pilin monomers) which are organized into ordered and repetitive patterns. Further, pili are structures which are involved in processes such as the attachment of bacterial cells to host cell surface receptors, intercellular genetic exchanges, and cell-cell recognition. Examples of pili include Type-1 pili, P-pili, F1C pili, S-pili, and 987P-pili. Additional examples of pili are set out elsewhere herein.

Pilus-like structure: As used herein, the phrase "pilus-like structure" refers to structures having characteristics similar to that of pili and composed of protein monomers. One example of a "pilus-like structure" is a structure formed by a bacterial cell which expresses modified pilin proteins that do not form ordered and repetitive arrays that are essentially identical to those of natural pili.

Polypeptide: As used herein, the term "polypeptide" refers to a molecule composed of monomers (amino acids) linearly linked by amide bonds (also known as peptide bonds). It indicates a molecular chain of amino acids and does not refer to a specific length of the product. Thus, peptides, dipeptides, tripeptides, oligopeptides and proteins are included within the definition of polypeptide. This term is also intended to refer to post-expression modifications of the polypeptide, for example, glycosolations, acetylations, phosphorylations, and the like. A recombinant or derived polypeptide is not necessarily translated from a designated nucleic acid sequence. It may also be generated in any manner, including chemical synthesis.

Protein: As used herein, the term protein refers to a polypeptide generally of a size of above about 5 or more, 10 or more 20 or more, 25 or more, 50 or more, 75 or more, 100 or more, 200 or more, 500 or more, 1000 or more, 2000 or more amino acids. Proteins generally have a defined three dimensional structure although they do not necessarily need to, and are often referred to as folded, as opposed to peptides and polypeptides which often do not possess a defined three-dimensional structure, but rather can adopt a large number of different conformations, and are referred to as unfolded. Peptides may, however, adopt three dimensional structures. The defined three-dimensional structures of proteins is especially important for the association between the core particle and the antigen, mediated by the second attachment site, and in particular by way of chemical cross-linking between the first and second attachment site using a chemical cross-linker. The amino acid linker is also intimately related to the structural properties of proteins in some aspects of the invention.

Purified: As used herein, when the term "purified" is used in reference to a molecule, it means that the concentration of the molecule being purified has been increased relative to molecules associated with it in its natural environment, or environment in which it was produced, found or synthesized. Naturally associated molecules include proteins, nucleic acids, lipids and sugars but generally do not include water, buffers, and reagents added to maintain the integrity or facilitate the purification of the molecule being purified. For example, even if mRNA is diluted with an aqueous solvent during oligo dT column chromatography, mRNA molecules are purified by this chromatography if naturally associated nucleic acids and other biological molecules do not bind to the column and are separated from the subject mRNA molecules. According to this definition, a substance may be 5% or more, 10% or more, 20% or more, 30% or more, 40% or more, 50% or more, 60% or more, 70% or more, 80% or more, 90% or more, 95% or more, 98% or more, 99% or more, or 100% pure when considered relative to its contaminants.

Receptor: As used herein, the term "receptor" refers to proteins or glycoproteins or fragments thereof capable of interacting with another molecule, called the ligand. The ligand may belong to any class of biochemical or chemical compounds. The receptor need not necessarily be a membrane-bound protein. Soluble protein, like e.g., maltose binding protein or retinol binding protein are receptors as well.

Residue: As used herein, the term "residue" is meant to mean a specific amino acid in a polypeptide backbone or side chain.

Recombinant host cell: As used herein, the term "recombinant host cell" refers to a host cell into which one ore more nucleic acid molecules of the invention have been introduced.

Recombinant virus: As used herein, the phrase "recombinant virus" refers to a virus that is genetically modified by the hand of man. The phrase covers any virus known in the art.

More specifically, the phrase refers to a an alphavirus genetically modified by the hand of man, and most specifically, the phrase refers to a Sinbis virus genetically modified by the hand of man.

RNA-phage, RNA-bacteriophage: As used herein, the term "RNA-bacteriophage," or its abbreviated form "RNA-phage" refers to RNA viruses infecting bacteria, preferably to single-stranded positive-sense RNA viruses infecting bacteria.

Self antigen: As used herein, the tem "self antigen" refers to proteins encoded by the host's DNA and products generated by proteins or RNA encoded by the host's DNA are defined as self. In addition, proteins that result from a combination of two or several self-molecules or that represent a fraction of a self-molecule and proteins that have a high homology two self-molecules as defined above (>95%, preferably >97%, more preferably >99%) may also be considered self.

Vaccine: As used herein, the term "vaccine" refers to a formulation which contains the composition of the present invention and which is in a form that is capable of being administered to an animal. Typically, the vaccine comprises a conventional saline or buffered aqueous solution medium in which the composition of the present invention is suspended or dissolved. In this form, the composition of the present invention can be used conveniently to prevent, ameliorate, or otherwise treat a condition. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses. Optionally, the vaccine of the present invention additionally includes an adjuvant which can be present in either a minor or major proportion relative to the compound of the present invention.

Vector: As used herein, the term "vector" refers to an agent (e.g., a plasmid or virus) used to transmit genetic material to a host cell. A vector may be composed of either DNA or RNA.

Virus-like particle: As used herein, the term "virus-like particle" refers to a structure resembling a virus particle. Moreover, a virus-like particle in accordance with the invention is non replicative and noninfectious since it lacks all or part of the viral genome, in particular the replicative and infectious components of the viral genome. A virus-like particle in accordance with the invention may contain nucleic acid distinct from their genome.

Virus-like particle of a bacteriophage: As used herein, the term "virus-like particle of a bacteriophage" refers to a virus-like particle resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. A virus-like particle in accodance with the invention lacks all or part of the viral genome, in particular the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, or RNA-phage. The terms "viral capsid" or "capsid", as interchangeably used herein, refer to a macromolecular assembly composed of viral protein subunits. Typically and preferably, the viral protein subunits assemble into a viral capsid and capsid, respectively, having a structure with an inherent repetitive organization, wherein said structure is, typically, spherical or tubular. For example, the capsids of RNA-phages or HBcAg's have a spherical form of icosahedral symmetry. The term "capsid-like structure" as used herein, refers to a macromolecular assembly composed of viral protein subunits ressembling the capsid morphology in the above defined sense but deviating from the typical symmetrical assembly while maintaining a sufficient degree of order and repetitiveness.

Virus-like particle of a bacteriophage: As used herein, the term "virus-like particle of a bacteriophage" refers to a virus-like particle resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition should, however, also encompass virus-like particles of bacteriophages, in which the aforementioned gene or genes are still present but inactive, and, therefore, also leading to non-replicative and noninfectious virus-like particles of a bacteriophage.

VLP of RNA phage coat protein: The capsid structure formed from the self-assembly of 180 subunits of RNA phage coat protein and optionally containing host RNA is referred to as a "VLP of RNA phage coat protein". A specific example is the VLP of Qβ coat protein. In this particular case, the VLP of Qβ coat protein may either be assembled exclusively from Qβ CP subunits (generated by expression of a Qβ CP gene containing, for example, a TAA stop codon precluding any expression of the longer A1 protein through suppression, see Kozlovska, T. M., et al., *Intervirology* 39: 9-15 (1996)), or additionally contain A1 protein subunits in the capsid assembly.

Virus particle: The term "virus particle" as used herein refers to the morphological form of a virus. In some virus types it comprises a genome surrounded by a protein capsid; others have additional structures (e.g., envelopes, tails, etc.).

One, A, or An: When the terms "one," "a" or "an" are used in this disclosure, they mean "at least one" or "one or more" unless otherwise indicated.

As used herein when referring to any numerical value, the term "about" means a value of ±10% of the stated value (e.g., "about 50° C." encompasses a range of temperatures from 45° C. to 55° C., inclusive; similarly, "about 100 mM" encompasses a range of concentrations from 90 mM to 110 mM inclusive).

Overview

In one aspect, the invention provides conjugates of one or more haptens with a carrier in an ordered and repetitive hapten-carrier conjugate, and methods of making such conjugates. The invention also provides compositions comprising at least one such conjugate of the invention and at least one other component, suitably at least one excipient or carrier and particularly at least one pharmaceutically acceptable excipient or carrier. Haptens suitably used in the conjugates and compositions of the invention include but are not limited to hormones, toxins and drugs, especially drugs of addiction, such as nicotine. The conjugates and compositions of the invention are useful for inducing immune responses against haptens. Such an immune response can be utilized to generate antibodies, useful for therapeutic, prophylactic and diagnostic purposes. Immune response can be useful to prevent or treat addiction to drugs of abuse and the resultant diseases associated with drug addiction.

The conjugates of the present invention comprise highly ordered and repetitive arrays of haptens. Conjugate arrays according to this aspect of the invention comprise (a) a core particle, comprising a first attachment site and (b) a hapten comprising a second attachment site, wherein the elements (a) and (b) are linked through the first and second attachment sites to form said ordered and repetitive hapten arrays.

Core particles suitably used in the conjugates and compositions of the invention may be natural or non-natural. Natural core particles of the present invention include virus particles, virus-like particles, and pili. The proteins of these natural core particles may be natural or recombinant. The first attachment sites on the core particle may occur naturally or may be introduced via chemical or recombinant means. Haptens of the present invention are those suitable for inducing immune responses against a variety of molecules, including but not limited to toxins, hormones and drugs, particularly drugs of abuse and or addiction. The second attachment site on the hapten may naturally occur or be introduced. The interaction between first and second sites may be direct, or may involve at least one other molecule, e.g. a linker. Linkers include cross-linking molecules.

The conjugates and compositions of the invention are suprisingly effective in inducing immune responses, particularly antibodies, against haptens. Thus, they are useful in compositions suitable for immunization of animals for therapeutic or prophylaxis against diseases, disorders or conditions associated with various drugs, hormones or toxins. Antibodies produced by immunization with the conjugates and compositions of the invention are also useful for therapeutic and prophylactic purposes.

In other embodiments, the invention provides methods of treatment and prevention of a disease utilizing the conjugates and compositions of the invention. In another embodiment, the invention provides kits suitable for diagnosis and screening.

Compositions of Ordered and Repetitive Antigen or Antigenic Determinant Arrays and Methods to Make the Same The present invention provides conjugates, and compositions of conjugates, comprising an ordered and repetitive hapten array. Furthermore, the invention conveniently enables the practitioner to construct ordered and repetitive hapten arrays for various purposes, and preferably the induction of an immune response against organic molecules.

Conjugates of the invention essentially comprise, or alternatively consist of, two elements: (1) a non-natural molecular scaffold; and (2) a hapten with at least one second attachment site capable of association through at least one bond to said first attachment site.

The non-natural molecular scaffold comprises, or alternatively consists of: (a) a core particle selected from the group consisting of (1) a core particle of non-natural origin and (2) a core particle of natural origin; and (b) at least one first attachment site connected to said core particle by at least one covalent bond. Core particles used in the conjugates, compositions and methods of the invention include inorganic molecules, virus particles, virus-like particles, and bacterial pili. The haptens used in the conjugates, compositions and methods of the invention has at least one second attachment site which is selected from the group consisting of (a) an attachment site not naturally occurring with said hapten; and (b) an attachment site naturally occurring with said antigen or antigenic determinant.

The invention provides for an ordered and repetitive hapten array through an association of the second attachment site to the first attachment site by way of at least one bond. Thus, the hapten and the non-natural molecular scaffold are brought together through this association of the first and the second attachment site to form an ordered and repetitive antigen array.

The practioner may specifically design the hapten and the second attachment site such that the arrangement of all the haptens bound to the non-natural molecular scaffold or, in certain embodiments, the core particle will be uniform. For example, one may place a single second attachment site on the hapten, thereby ensuring through design that all haptens that are attached to the non-natural molecular scaffold are positioned in a uniform way. Thus, the invention provides a convenient means of placing any hapten onto a non-natural molecular scaffold in a defined order and in a manner which forms a repetitive pattern.

As will be clear to those of ordinary skill in the art, certain embodiments of the invention involve the use of recombinant nucleic acid technologies such as cloning, polymerase chain reaction, the purification of DNA and RNA, the expression of recombinant proteins in prokaryotic and eukaryotic cells, etc. Such methodologies are well known to those skilled in the art and may be conveniently found in published laboratory methods manuals (e.g., Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997)). Fundamental laboratory techniques for working with tissue culture cell lines (Celis, J., ed., CELL BIOLOGY, Academic Press, $2^{nd}$ edition, (1998)) and antibody-based technologies (Harlow, E. and Lane, D., "Antibodies: A Laboratory Manual," Cold Spring Harbor Laboratory, Cold Spring Harbor, N.Y. (1988); Deutscher, M. P., "Guide to Protein Purification," *Meth. Enzymol.* 128, Academic Press San Diego (1990); Scopes, R. K., "Protein Purification Principles and Practice," $3^{rd}$ ed., Springer-Verlag, New York (1994)) are also adequately described in the literature, all of which are incorporated herein by reference.

Furthermore, technologies for coupling organic molecules to amino acids and means for making derivatives of haptens containing appropriate second attachment sites such as are neccessary for the practice of the invention are well known to those of skill in the art. Such methodologies may be found in chemical text books and publications, examples of which are included below and are incorportated by reference; U.S. Pat. No. 5,876,727; WO 99/61054; Isomura, S. et al. *J. Org. Chem.* 66:4115-4121 (2001); Matsushita, H. et al. *Biochem. Biophys. Res. Comm.* 57:1006-1010. (1974); Langone, J. L. and Van Vunakis, H., *Methods Enzymol.* 84:628-640 (1982); Wong, *Chemistry of Protein Conjugation and Cross-Linking.* CRC Press, Inc., Boca Raton, Fla. (1991.)

Core Particles and Non-Natural Molecular Scaffolds

In one embodiment, the present invention provides methods for the formation of an ordered and repetitive array of haptens. By the invention, this occurs by the association of a core particle to which is attached one or more haptens via first and second attachment sites.

Thus, one element in certain conjugates and compositions of the invention is a non-natural molecular scaffold comprising, or alternatively consisting of, a core particle and a first attachment site. More specifically, the non-natural molecular scaffold comprises, or alternatively consists of, (a) a core particle of natural or non-natural origin and (b) at least one first attachment site connected to the core particle by at least one covalent bond.

Core particles. In one embodiment of the present invention, a core particle is a synthetic polymer, a lipid micelle or a metal. Such core particles are known in the art, providing a basis from which to build the non-natural molecular scaffold of the invention. By way of example, synthetic polymer or metal core particles are disclosed in U.S. Pat. No. 5,770,380, and U.S. Pat. No. 5,334,394, which are incorporated by reference herein in their entireties. Suitable metals include, but are not limited to, chromium, rubidium, iron, zinc, selenium, nickel, gold, silver, platinum. Suitable ceramic materials include, but are not limited to, silicon dioxide, titanium dioxide, aluminum oxide, ruthenium oxide and tin oxide. The core particles of this embodiment may be made from organic materials including, but not limited to, carbon and suitable polymers, including polystyrene, nylon and nitrocellulose. For nanocrystalline particles, particles made from tin oxide, titanium dioxide or carbon (diamond) are useful. Lipid micelles for use in the present invention are prepared by any means known in the art, for example, Baiselle and Millar (*Biophys. Chem.* 4:355-361 (1975)) or Corti et al. (*Chem. Phys. Lipids* 38:197-214 (1981)) or Lopez et al. (*FEBS Lett.* 426:314-318 (1998)) or Topchieva and Karezin (*J. Colloid Interface Sci.* 213:29-35 (1999)) or Morein et al., (*Nature* 308:457-460 (1984)), which are incorporated herein by reference in their entireties.

In one embodiment of the invention the core particle is produced through a biological process, which may be natural or non-natural. For example, viruses and bacterial pili or pilus-like structures are formed from proteins which are organized into ordered and repetitive structures. Therefore, the present invention comprises conjugates, compositions and methods comprising useful core particles which include, but are not limited to a virus, virus-like particle, a bacterial pilus, a phage, a viral capsid particle or fragments thereof. In certain such embodiments, the proteins may be recombinant.

In certain embodiments, the core particle of the non-natural molecular scaffold comprises a virus, a bacterial pilus, a structure formed from bacterial pilin, a bacteriophage, a virus-like particle, a viral capsid particle or a recombinant form thereof. Any virus known in the art having an ordered and repetitive coat and/or core protein structure may be selected for use as in the methods, conjugates and compositions of the invention as a non-natural molecular scaffold. Examples of suitable viruses include, but are not limited to, sindbis and other alphaviruses, rhabdoviruses (e.g. vesicular stomatitis virus), picomaviruses (e.g., human rhino virus, Aichi virus), togaviruses (e.g., rubella virus), orthomyxoviruses (e.g., Thogoto virus, Batken virus, fowl plague virus), polyomaviruses (e.g., polyomavirus BK, polyomavirus JC, avian polyomavirus BFDV), parvoviruses, rotaviruses, bacteriophage Qβ, bacteriophage R17, bacteriophage M11, bacteriophage MX1, bacteriophage NL95, bacteriophage fr, bacteriophage GA, bacteriophage SP, bacteriophage MS2, bacteriophage f2, bacteriophage PP7, bacteriophage AP205, Norwalk virus, foot and mouth disease virus, a retrovirus, Hepatitis B virus, Tobacco mosaic virus, Flock House Virus, and human Papilomavirus (for example, see Table 1 in Bachman, M. F. and Zinkernagel, R. M., *Immunol. Today* 17:553-558 (1996)). In more specific exemplary embodiments of the present invention the core particle may comprise, or alternatively consist of, recombinant proteins of Rotavirus, recombinant proteins of Norwalk virus, recombinant proteins of Alphavirus, recombinant proteins which form bacterial pili or pilus-like structures, recombinant proteins of Foot and Mouth Disease virus, recombinant proteins of Retrovirus, recombinant proteins of Hepatitis B virus (e.g., a HBcAg), recombinant proteins of Tobacco mosaic virus, recombinant proteins of Flock House Virus, and recombinant proteins of human Papilomavirus.

The core particle used in conjugates, compositions and methods of the invention may further comprise, or alternatively consist of, one or more fragments of such proteins, as well as variants of such proteins which retain the ability to associate with each other to form ordered and repetitive antigen or antigenic determinant arrays. For example, as explained in WO 02/056905 core particles may be formed from variant forms of the human HBcAg which differ markedly from the wild-type particle in amino acid sequence identity and similarity, and in sequence length. For example, amino acid sequence of the HBcAg of Hepatitis B viruses which infect snow geese and ducks differs sufficiently from that of HBcAg of viruses infected mammals that alignment of the proteins is difficult. However, both viruses retain the ability to form core structures suitable for the formation of ordered repetitive hapten arrays. Similarly, HBcAg may retain the ability to form multimeric particles, typical of a virus, after removal of N-terminal leader sequences, further deletions, substitutions, or additions to the sequence. Methods which can be used to determine whether proteins form such structures comprise gel filtration, agarose gel electrophoresis, sucrose gradient centrifugation and electron microscopy (e.g., Koschel, M. et al., *J. Virol* 73: 2153-2160 (1999)).

First Attachment Sites. Whether natural or non-natural, the core particle used in the conjugates, compositions and methods of the present invention will generally possess a component comprising a first attachment site that is attached to the natural or non-natural core particle by at least one covalent bond. The element comprising the first attachment site is bound to a core particle in a non-random fashion that provides a nucleation site for creating an ordered and repetitive antigen array. Ideally, but not necessarily, this element is associated with the core particle in a geometric order. The first attachment site may be a natural part of the core particle, such as a surface exposed amino acid residue suitable for coupling to the second attachment site. For example, lysine and cysteine may form non-peptide bonds via reactive groups on the amino acid. Alternatively, an element containing the first attachment site may be introduced into the core particle via chemical coupling or through the design of recombinant molecules. The first attachment site may be, or be found on, any element comprising bound to a core particle by at least one covalent bond.

Elements comprising, or alternatively consisting of, the first attachment site may be proteins, a polypeptide, a peptide, an amino acid (i.e., a residue of a protein, a polypeptide or peptide), a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. In a more specific embodiment, the first attachment site comprising an antigen, an antibody or antibody fragment, biotin, avidin, strepavidin, a receptor, a receptor ligand, a ligand, a ligand-binding protein, an interacting leucine zipper polypeptide, an amino group, a chemical group reactive to an amino group; a carboxyl group, chemical group reactive to a carboxyl group, a sulfhydryl group, a chemical group reactive to a sulfhydryl group, or a combination thereof.

In one embodiment, the invention utilizes genetic engineering of a virus to create a fusion between an ordered and repetitive viral envelope protein the element comprising the first attachment site which comprising a heterologous protein, peptide, antigenic determinant or a reactive amino acid residue of choice. Other genetic manipulations known to those in the art may be included in the construction of the non-natural molecular scaffold; for example, it may be desirable to restrict the replication ability of the recombinant virus through genetic mutation. The viral protein selected for fusion to the protein containing the first attachment site protein should have an organized and repetitive structure. Such an organized and repetitive structure include paracrystalline organizations with a spacing of 0.5-30, preferably 5-15 nm, on the surface of the virus. The creation of this type of fusion protein will result in multiple, ordered and repetitive first attachment sites on the surface of the virus. Thus, the ordered and repetitive organization of the first attachment sites resulting therefrom will reflect the normal organization of the native viral protein.

As will be understood by those of ordinary skill in the art, the first attachment site may be or be a part of any suitable protein, polypeptide, sugar, polynucleotide, peptide (amino acid), natural or synthetic polymer, a secondary metabolite or combination thereof that may serve to specifically attach the antigen or antigenic determinant of choice to the non-natural molecular scaffold. In one embodiment, the attachment site is a protein or peptide that may be selected from those known in the art. For example, the first attachment site may be a ligand, a receptor, a lectin, avidin, streptavidin, biotin, an epitope such as an HA or T7 tag, Myc, Max, immunoglobulin domains and any other amino acid sequence known in the art that would be useful as a first attachment site.

It will be further understood by those of ordinary skill in the art that with another embodiment of the invention, the first attachment site may be created secondarily to the creation of an element carrying the first attachment site (i.e., protein or polypeptide) utilized in constructing the in-frame fusion to the capsid protein. For example, a protein may be utilized for fusion to the envelope protein with an amino acid sequence known to be glycosylated in a specific fashion, and the sugar moiety added as a result may then serve at the first attachment site of the viral scaffold by way of binding to a lectin serving as the secondary attachment site of an antigen. Alternatively, a sequence may be biotinylated in vivo and the biotin moiety may serve as the first attachment site of the invention, or the sequence may be subjected to chemical modification of distinct amino acid residues in vitro, the modification serving as the first attachment site.

In one specific embodiment of the invention, the first attachment site is the JUN-FOS leucine zipper protein domain that is fused in frame to the Hepatitis B capsid (core) protein (HBcAg). However, it will be clear to those of ordinary skill in the art that other viral capsid proteins may be utilized in the fusion protein construct for locating the first attachment site in the non-natural molecular scaffold of the invention. For example, in other embodiments of the invention, the first attachment site is selected to be a lysine or cysteine residue that is fused in frame to the HBcAg. However, it will be clear to all individuals in the art that other viral capsid or virus-like particles may be utilized in the fusion protein construct for locating the first attachment in the non-natural molecular scaffold of the invention.

Viral particles. In one embodiment of the invention, the core particle is a recombinant alphavirus, and more specifically, a recombinant Sindbis virus. Several members of the alphavirus family, Sindbis (Xiong, C. et al., *Science* 243: 1188-1191 (1989); Schlesinger, S., *Trends Biotechnol.* 11:18-22 (1993)), Semliki Forest Virus (SFV) (Liljeström, P. & Garoff, H., *Bio/Technology* 9:1356-1361 (1991)) and others (Davis, N. L. et al., *Virology* 171:189-204 (1989)), have received considerable attention for use as virus-based expression vectors for a variety of different proteins (Lundstrom, K., *Curr. Opin. Biotechnol.* 8:578-582 (1997); Liljeström, P., *Curr. Opin. Biotechnol.* 5:495-500 (1994)) and as candidates for vaccine development. The use of alphaviruses for the expression of heterologous proteins and the development of vaccines has been disclosed (see U.S. Pat. Nos. 5,766,602; 5,792,462; 5,739,026; 5,789,245; and 5,814,482) the disclosures all of which are incorporated by reference in their entireties. The construction of the alphaviral scaffold of the invention may be done by means generally known in the art of recombinant DNA technology, as described by the aforementioned articles, which are incorporated herein by reference. A variety of different recombinant host cells can be utilized to produce a viral-based core particle for antigen or antigenic determinant attachment.

Packaged RNA sequences can also be used to infect host cells. These packaged RNA sequences can be introduced to host cells by adding them to the culture medium. For example, the preparation of non-infective alpahviral particles is described in a number of sources, including "Sindbis Expression System", Version C (Invitrogen Corporation, Carlsbad Calif.; Catalog No. K750-1).

When mammalian cells are used as recombinant host cells for the production of viral-based core particles, these cells will generally be grown in tissue culture. Methods for growing cells in culture are well known in the art (see, e.g., Celis, J., ed., CELL BIOLOGY, Academic Press, $2^{nd}$ edition, (1998); Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997); Freshney, R., CULTURE OF ANIMAL CELLS, Alan R. Liss, Inc. (1983)).

The invention thus includes viral-based core particles which comprise, or alternatively consist of, a virus, virus-like particle, a phage, a viral capsid particle or a recombinant form thereof. Skilled artisans have the knowledge to produce such core particles and attach first attachment sites thereto. The production of Hepatitis B virus-like particles, in particular those assembled or self-assembled from HBcAg, and measles viral capsid particles as core particles is disclosed in Examples 17 to 22 of WO 00/32227, which is explicitly incorporated herein by reference. In such embodiments, the JUN leucine zipper protein domain or FOS leucine zipper protein domain may be used as a first attachment site for the non-natural molecular scaffold of the invention. One of skill in the art would known methods for constructing Hepatitis B core particles carrying an in-frame fused peptide with a reactive lysine residue and antigens carrying a genetically fused cysteine residue, as first and second attachment site, respectively.

In other embodiments, the core particles used in compositions of the invention are composed of a Hepatitis B capsid (core) protein (HBcAg), a fragment of a HBcAg, or other protein or peptide which can form virus-like particles, which are ordered arrays, which have been modified to either eliminate or reduce the number of free cysteine residues. Zhou et al. (*J. Virol.* 66:5393-5398 (1992)) demonstrated that HBcAgs which have been modified to remove the naturally resident cysteine residues retain the ability to associate and form multimeric structures. Thus, core particles suitable for use in compositions of the invention include those comprising modified HBcAgs, or fragments thereof, in which one or more of the naturally resident cysteine residues have been either deleted or substituted with another amino acid residue (e.g., a serine residue). In a preferred embodiment, the HBcAg has the amino acid sequence as set forth in SEQ ID NO: 1, or a sequence that is at least about 80%, at least about 85%, at least about 90%, at least about 95%, more preferably at least about 99% or 100% identical to the sequence of SEQ ID NO: 1. In one embodiment of the invention, a modified HBcAg comprising the amino acid sequence shown in SEQ ID NO:1, or subportion thereof, is used to prepare non-natural molecular scaffolds. In particular, modified HBcAgs suitable for use in the practice of the invention include proteins in which one or more of the cysteine residues at positions corresponding to positions 48, 61, 107 and 185 of a protein having the amino acid sequence shown in SEQ ID NO:1 have been either deleted or substituted with other amino acid residues (e.g., a serine residue). As one skilled in the art would recognize, cysteine residues at similar locations in HBcAg variants having amino acids sequences which differ from that shown in SEQ ID NO:1 could also be deleted or substituted with other amino acid residues. The modified HBcAg variants can then be used to prepare vaccine compositions of the invention.

Under certain circumstances (e.g., when a heterobifunctional cross-linking reagent is used to attach antigens or antigenic determinants to the non-natural molecular scaffold), the presence of free cysteine residues in the HBcAg is believed to lead to covalent coupling of toxic components to core particles, as well as the cross-linking of monomers to form undefined species.

Further, in many instances, these toxic components may not be detectable with assays performed on compositions of the invention. This is so because covalent coupling of toxic components to the non-natural molecular scaffold would result in the formation of a population of diverse species in which toxic components are linked to different cysteine residues, or in some cases no cysteine residues, of the HBcAgs. In other words, each free cysteine residue of each HBcAg will not be covalently linked to toxic components. Further, in many instances, none of the cysteine residues of particular HBcAgs will be linked to toxic components. Thus, the presence of these toxic components may be difficult to detect because they would be present in a mixed population of molecules. The administration to an individual of HBcAg species containing toxic components, however, could lead to a potentially serious adverse reaction.

It is well known in the art that free cysteine residues can be involved in a number of chemical side reactions. These side reactions include disulfide exchanges, reaction with chemical substances or metabolites that are, for example, injected or formed in a combination therapy with other substances, or direct oxidation and reaction with nucleotides upon exposure to UV light. Toxic adducts could thus be generated, especially considering the fact that HBcAgs have a strong tendency to bind nucleic acids. Detection of such toxic products in antigen-capsid conjugates would be difficult using capsids prepared using HBcAgs containing free cysteines and heterobifunctional cross-linkers, since a distribution of products with a broad range of molecular weight would be generated. The toxic adducts would thus be distributed between a multiplicity of species, which individually may each be present at low concentration, but reach toxic levels when together.

In view of the above, one advantage to the use of HBcAgs in vaccine compositions which have been modified to remove naturally resident cysteine residues is that sites to which toxic species can bind when antigens or antigenic determinants are attached to the non-natural molecular scaffold would be reduced in number or eliminated altogether. Further, a high concentration of cross-linker can be used to produce highly decorated particles without the drawback of generating a plurality of undefined cross-linked species of HBcAg monomers (i.e., a diverse mixture of cross-linked monomeric HbcAgs).

A number of naturally occurring HBcAg variants suitable for use in the practice of the present invention have been identified. Yuan et al., (*J. Virol.* 73:10122-10128 (1999)), for example, describe variants in which the isoleucine residue at position corresponding to position 97 in SEQ ID NO:1 is replaced with either a leucine residue or a phenylalanine residue. The amino acid sequences of a number of HBcAg variants, as well as several Hepatitis B core antigen precursor variants, are disclosed in GenBank reports AAF121240, AF121239, X85297, X02496, X85305, X85303, AF151735, X85259, X85286, X85260, X85317, X85298, AF043593, M20706, X85295, X80925, X85284, X85275, X72702, X85291, X65258, X85302, M32138, X85293, X85315, U95551, X85256, X85316, X85296, AB033559, X59795, X8529, X85307, X65257, X85311, X85301, X85314, X85287, X85272, X85319, AB010289, X85285, AB010289, AF121242, M90520, P03153, AF110999, and M95589, the disclosures of each of which are incorporated herein by reference. These HBcAg variants differ in amino acid sequence at a number of positions, including amino acid residues which corresponds to the amino acid residues located at positions 12, 13, 21, 22, 24, 29, 32, 33, 35, 38, 40, 42, 44, 45, 49, 51, 57, 58, 59, 64, 66, 67, 69, 74, 77, 80, 81, 87, 92, 93, 97, 98, 100, 103, 105, 106, 109, 113, 116, 121, 126, 130, 133, 135, 141, 147, 149, 157, 176, 178, 182 and 183 in SEQ ID NO:1.

Further HBcAg variants suitable for use in the compositions of the invention, and which may be further modified according to the disclosure of this specification are described in WO 00/198333, WO 00/177158 and WO 00/214478, herein included by reference in their entirety.

HBcAgs suitable for use in the present invention may be derived from any organism so long as they are able to associate to form an ordered and repetitive antigen array. Generally processed HBcAgs (i.e., those which lack leader sequences) will be used in the vaccine compositions of the invention. The present invention includes vaccine compositions, as well as methods for using these compositions, which employ the above described variant HBcAgs for the preparation of non-natural molecular scaffolds. Further included within the scope of the invention are additional HBcAg variants which are capable of associating to form dimeric or multimeric structures. Thus, the invention further includes vaccine compositions comprising HBcAg polypeptides comprising, or alternatively consisting of, amino acid sequences which are at least about 80%, about 85%, about 90%, about 95%, about 97%, or about 99% identical to any of the amino acid sequences shown in the above sequences, including SEQ ID No: 1, and forms of these proteins which have been processed, where appropriate, to remove the N-terminal leader sequence.

Whether the amino acid sequence of a polypeptide has an amino acid sequence that is at least about 80%, about 85%, about 90%, about 95%, about 97%, or about 99% identical to one of the amino acid sequences shown above, or a subportion thereof, can be determined conventionally using known computer programs such the Bestfit program. When using Bestfit or any other sequence alignment program to determine whether a particular sequence is, for instance, about 95% identical to a reference amino acid sequence according to the present invention, the parameters are set such that the percentage of identity is calculated over the full length of the reference amino acid sequence and that gaps in homology of up to 5% of the total number of amino acid residues in the reference sequence are allowed. In such a manner, comparisons may be made between the amino acid sequence of HBcAg of SEQ ID NO:1 and other HBcAg. When comparing proteins that are relatively similar, reference to an amino acid residue of a HBcAg variant located at a position which corresponds to a particular position in SEQ ID NO:1, refers to the amino acid residue which is present at that position in the amino acid sequence shown in SEQ ID NO:1. The homology between these HBcAg variants is for the most part high enough among Hepatitis B viruses that infect mammals so that one skilled in the art would have little difficulty reviewing both the amino acid sequence shown in SEQ ID NO:1 and that of a particular HBcAg variant and identifying "corresponding" amino acid residues. For example, comparisons between the SEQ ID NO:1 and the amino acid sequence of the an HBcAg derived from a virus which infect woodchucks, it is readily apparent that a three amino acid residue insert is present in that sequence between amino acid residues 155 and 156 of SEQ ID NO:1.

However, where alignment is difficult, one skilled in the art would recognize the importance of particular amino acids or motifs in a sequence. For example, the amino acid sequence of HBcAg from human viruses differs from duck viruses such that alignment is difficult, yet one skilled in the art would recognize conserved cysteine residues could be either substituted with another amino acid residue or deleted prior to their inclusion in vaccine compositions of the invention.

In one embodiment, the cysteine residues at positions 48 and 107 of a protein having the amino acid sequence shown in SEQ ID NO:1 are deleted or substituted with another amino acid residue but the cysteine at position 61 is left in place. Further, the modified polypeptide is then used to prepare vaccine compositions of the invention.

The preparation of preferred Hepatitis B virus-like particles, which can be used for the present invention, is disclosed, for example, in WO 00/32227, and hereby in particular in Examples 17 to 19 and 21 to 24, as well as in WO 01/85208, and hereby in particular in Examples 17 to 19, 21 to 24, 31 and 41, and in WO 02/056905. For the latter application, it is in particular referred to Example 23, 24, 31 and 51. All three documents are explicitly incorporated herein by reference.

As set out below in Example 31 of WO 02/056905, the cysteine residues at positions 48 and 107, which are accessible to solvent, may be removed, for example, by site-directed mutagenesis. Further, the inventors have found that the Cys-48-Ser, Cys-107-Ser HBcAg double mutant constructed as described in WO 02/056905, (which is incorporated herein by reference in its entirety) can be expressed in *E. coli*.

As discussed above, the elimination of free cysteine residues reduces the number of sites where toxic components can bind to the HBcAg, and also eliminates sites where cross-linking of lysine and cysteine residues of the same or of neighboring HBcAg molecules can occur. The cysteine at position 61, which is involved in dimer formation and forms a disulfide bridge with the cysteine at position 61 of another HBcAg, will normally be left intact for stabilization of HBcAg dimers and multimers of the invention. Cross-linking experiments performed with (1) HBcAgs containing free cysteine residues and (2) HBcAgs whose free cysteine residues have been made unreactive with iodacetamide, indicate that free cysteine residues of the HBcAg are responsible for cross-linking between HBcAgs through reactions between heterobifunctional cross-linker derivatized lysine side chains, and free cysteine residues. It was also found that that cross-linking of HBcAg subunits leads to the formation of high molecular weight species of undefined size which can not be resolved by SDS-polyacrylamide gel electrophoresis.

When an antigen or antigenic determinant is linked to the non-natural molecular scaffold through a lysine residue, it may be advantageous to either substitute or delete one or both of the naturally resident lysine residues located at positions corresponding to positions 7 and 96 in SEQ ID NO:1, as well as other lysine residues present in HBcAg variants. The elimination of these lysine residues results in the removal of binding sites for antigens or antigenic determinants which could disrupt the ordered array and should improve the quality and uniformity of the final vaccine composition.

In many instances, when both of the naturally resident lysine residues at positions corresponding to positions 7 and 96 in SEQ ID NO:1 are eliminated, another lysine will be introduced into the HBcAg as an attachment site for an antigen or antigenic determinant. Methods for inserting such a lysine residue are set out, for example, in Example 23 of WO 02/056905, which is incorporated hereby by reference in its entirety. It will often be advantageous to introduce a lysine residue into the HBcAg when, for example, both of the naturally resident lysine residues at positions corresponding to positions 7 and 96 in SEQ ID NO:1 are altered and one seeks to attach the antigen or antigenic determinant to the non-natural molecular scaffold using a heterobifunctional cross-linking agent.

The C-terminus of the HBcAg has been shown to direct nuclear localization of this protein (Eckhardt et al., *J. Virol.* 65:575-582 (1991).) Further, this region of the protein is also believed to confer upon the HBcAg the ability to bind nucleic acids.

In some embodiments, vaccine compositions of the invention will contain HBcAgs which have nucleic acid binding activity (e.g., which contain a naturally resident HBcAg nucleic acid binding domain). HBcAgs containing one or more nucleic acid binding domains are useful for preparing vaccine compositions which exhibit enhanced T-cell stimulatory activity. Thus, the vaccine compositions of the invention include compositions which contain HBcAgs having nucleic acid binding activity. Further included are vaccine compositions, as well as the use of such compositions in vaccination protocols, where HBcAgs are bound to nucleic acids. These HBcAgs may bind to the nucleic acids prior to administration to an individual or may bind the nucleic acids after administration.

Further HBcAgs suitable for use in the practice of the present invention include N- and C-terminal truncation mutants, and muteins whose amino acid sequences comprises or alternatively consists of, amino acid sequences which are at least about 80%, about 85%, about 90%, about 95%, about 97%, or about 99% identical to the above described truncation mutants.

As discussed above, in certain embodiments of the invention, a lysine residue is introduced as a first attachment site into a polypeptide which forms the non-natural molecular scaffold. In preferred embodiments, vaccine compositions of the invention are prepared using a HBcAg comprising, or alternatively consisting of, amino acids 1-144 or amino acids 1-149 or amino acids 1-185 of SEQ ID NO:1 which is modified so that the amino acids corresponding to positions 79 and 80 are replaced with a peptide having the amino acid sequence of Gly-Gly-Lys-Gly-Gly (SEQ ID NO: 11) and the cysteine residues at positions 48 and 107 are either deleted or substituted with another amino acid residue, while the cysteine at position 61 is left in place.

The invention further includes vaccine compositions comprising fragments of a HBcAg comprising, or alternatively consisting of, an amino acid sequence other than that shown in SEQ ID NO:1 from which a cysteine residue not present at corresponding location in SEQ ID NO:1 has been deleted.

Vaccine compositions of the invention may comprise mixtures of different HBcAgs. Thus, these vaccine compositions may be composed of HBcAgs which differ in amino acid sequence. For example, vaccine compositions could be prepared comprising a "wild-type" HBcAg and a modified HBcAg in which one or more amino acid residues have been altered (e.g., deleted, inserted or substituted). The invention further includes vaccine compositions where the non-natural molecular scaffold is prepared using a HBcAg fused to another protein. As discussed above, one example of such a fusion protein is a HBcAg/FOS fusion. Other examples of HBcAg fusion proteins suitable for use in vaccine compositions of the invention include fusion proteins where an amino acid sequence has been added which aids in the formation and/or stabilization of HBcAg dimers and multimers. This additional amino acid sequence may be fused to the or C-terminus of the HBcAg. One example, of such a fusion protein is a fusion of a HBcAg with the GCN4 helix region of *Saccharomyces cerevisiae*, which forms homodimers via non-covalent interactions which can be used to prepare and stabilize HBcAg dimers and multimers.

In one embodiment, the invention provides vaccine compositions prepared using HBcAg fusions proteins comprising a HBcAg, or fragment thereof, with a GCN4 polypeptide (PAALKRARNEAARRSRARKLQ-RMKQLEDKVEELL-SKNYHLENEVARLKK (SEQ ID NO: 12)) fused to the C-terminus. This GCN4 polypeptide may also be fused to the N-terminus of the HbcAg.

HBcAg/src homology 3 (SH3) domain fusion proteins could also be used to prepare vaccine compositions of the invention. SH3 domains are relatively small domains found in a number of proteins which confer the ability to interact with specific proline-rich sequences in protein binding partners (see McPherson, *Cell Signal* 11:229-238 (1999). HBcAg/SH3 fusion proteins could be used in several ways. First, the SH3 domain could form a first attachment site which interacts with a second attachment site of the antigen or antigenic determinant. Similarly, a proline rich amino acid sequence could be added to the HBcAg and used as a first attachment site for an SH3 domain second attachment site of an antigen or antigenic determinant. Second, the SH3 domain could associate with proline rich regions introduced into HBcAgs. Thus, SH3 domains and proline rich SH3 interaction sites could be inserted into either the same or different HBcAgs and used to form and stabilized dimers and multimers of the invention.

As evidenced by the aforementioned example, one of skill in the art would know how to form a molecular scaffold comprising core particles and a first attachment site from HBcAg and HBcAg-derived muteins. By application of art-known techniques and routine experimentation, it would be understood by one of ordinary skill how other viruses could be similarly used to construct a molecular scaffold.

As presented elsewhere herein, viral capsids may be used for (1) the presentation or haptens and (2) the preparation of vaccine compositions of the invention. Particularly, useful in the practice of the invention are viral capsid proteins, also referred to herein as "coat proteins," which upon expression form capsids or capsid-like structures. Thus, these capsid proteins can form core particles and non-natural molecular scaffolds. Generally, these capsids or capsid-like structures form ordered and repetitive arrays which can be used for the presentation of haptens determinants and the preparation of vaccine compositions of the invention.

One or more (e.g., one, two, three, four, five, etc.) haptens may be attached by any number of means to one or more (e.g., one, two, three, four, five, etc.) proteins which form viral capsids or capsid-like structures (e.g., bacteriophage coat proteins), as well as other proteins. For example, haptens may be attached to core particles using first and second attachment sites. Further, one or more (e.g., one, two, three, four, five, etc.) heterobifunctional crosslinkers can be used to attach haptens determinants to one or more proteins which form viral capsids or capsid-like structures.

Viral capsid proteins, or fragments thereof may be used, for example, to prepare core particles and vaccine compositions of the invention. Bacteriophage Qβ coat proteins, for example, can be expressed recombinantly in *E. coli*. Further, upon such expression these proteins spontaneously form capsids, which are virus-like particles. Additionally, these capsids form ordered and repetitive antigen arrays which can be used for hapten presentation and the preparation of vaccine compositions. As described below in Example 1, bacteriophage Qβ coat proteins can be used to prepare vaccine compositions which elicit immunological responses to haptens.

In a preferred embodiment, the virus-like particle comprises, consists essentially of, or alternatively consists of recombinant proteins, or fragments thereof, of a RNA-phage. Preferably, the RNA-phage is selected from the group consisting of a) bacteriophage Qβ; b) bacteriophage R17; c) bacteriophage fr; d) bacteriophage GA; e) bacteriophage SP; f) bacteriophage MS2; g) bacteriophage M11; h) bacteriophage MX1; i) bacteriophage NL95; k) bacteriophage f2; l) bacteriophage PP7, and m) bacteriophage AP205.

In another preferred embodiment of the present invention, the virus-like particle comprises, or alternatively consists essentially of, or alternatively consists of recombinant proteins, or fragments thereof, of the RNA-bacteriophage Qβ or of the RNA-bacteriophage fr or of the RNA-bacteriophage AP205.

In a further preferred embodiment of the present invention, the recombinant proteins comprise, or alternatively consist essentially of, or alternatively consist of coat proteins of RNA phages.

Specific examples of bacteriophage coat proteins which can be used to prepare compositions of the invention include the coat proteins of RNA bacteriophages such as bacteriophage Qβ (SEQ ID NO:3, PIR Database, Accession No. VCBPQβ referring to Qβ CP; and SEQ ID NO: 4, Accession No. AAA16663 referring to Qβ A1 protein), bacteriophage R17 (SEQ ID NO: 24; PIR Accession No. VCBPR7), bacteriophage fr (SEQ ID NO: 25; PIR Accession No. VCBPFR), bacteriophage GA (SEQ ID NO: 26; GenBank Accession No. NP-040754), bacteriophage SP (SEQ ID NO: 27; GenBank Accession No. CAA30374 referring to SP CP and SEQ ID NO: 28, Accession No. NP 695026 referring to SP A1 protein), bacteriophage MS2 (SEQ ID NO: 29; PIR Accession No. VCBPM2), bacteriophage M11 (SEQ ID NO: 30; GenBank Accession No. AAC06250), bacteriophage MX1 (SEQ ID NO: 31; GenBank Accession No. AAC14699), bacteriophage NL95 (SEQ ID NO: 32; GenBank Accession No. AAC14704), bacteriophage f2 (SEQ ID NO: 33; GenBank Accession No. P03611), bacteriophage PP7 (SEQ ID NO: 13), bacteriophage AP205 (SEQ ID NO:14). As one skilled in the art would recognize, any protein which forms capsids or capsid-like structures can be used for the preparation of vaccine compositions of the invention. Furthermore, the A1 protein of bacteriophage Qβ (Genbank accession No. AAA16663 (SEQ ID NO: 4)) or C-terminal truncated forms missing as much as about 100, about 150 or about 180 amino acids from its C-terminus may be incorporated in a capsid assembly of Qβ coat proteins. The A1 protein may also be fused an element containing a first attachment site, for attachment of haptens containing a second attachment site. Generally, the percentage of A1 protein relative to Qβ CP in the capsid assembly will be limited, in order to insure capsid formation.

Qβ coat protein has also been found to self-assemble into capsids when expressed in *E. coli* (Kozlovska T M. et al., *GENE* 137: 133-137 (1993)). The obtained capsids or virus-like particles showed an icosahedral phage-like capsid structure with a diameter of 25 nm and T=3 quasi symmetry. Further, the crystal structure of phage Qβ has been solved. The capsid contains 180 copies of the coat protein, which are linked in covalent pentamers and hexamers by disulfide bridges (Golmohammadi, R. et al., *Structure* 4: 543-5554 (1996)). Other RNA phage coat proteins have also been shown to self-assemble upon expression in a bacterial host (Kastelein, R A. et al., *Gene* 23: 245-254 (1983), Kozlovskaya, T M. et al., *Dokl. Akad. Nauk SSSR* 287: 452-455 (1986), Adhin, M R. et al., *Virology* 170: 238-242 (1989), Ni, C Z., et al., *Protein Sci.* 5: 2485-2493 (1996), Priano, C. et al., J. Mol. Biol. 249: 283-297 (1995)). The Qβ phage capsid contains, in addition to the coat protein, the so called read-through protein A1 and the maturation protein A2. A1 is generated by suppression at the UGA stop codon and has a length of 329 aa. The capsid of phage Qβ recombinant coat protein used in the invention is devoid of the A2 lysis protein, and contains RNA from the host. The coat protein of RNA phages is an RNA binding protein, and interacts with the stem loop of the ribosomal binding site of the replicase gene acting as a translational repressor during the life cycle of the virus. The sequence and structural elements of the interaction are known (Witherell, G W. & Uhlenbeck, O C. *Biochemistry* 28: 71-76 (1989); Lim F. et al., *J. Biol. Chem.* 271: 31839-31845 (1996)). The stem loop and RNA in general are known to be involved in the virus assembly (Golmohammadi, R. et al., *Structure* 4: 543-5554 (1996).)

Upon expression in *E. coli*, the N-terminal methionine of Qβ coat protein is usually removed, as we observed by N-terminal Edman sequencing as described in Stoll, E. et al. J. Biol. Chem. 252:990-993 (1977). VLP composed from Qβ coat proteins where the N-terminal methionine has not been removed, or VLPs comprising a mixture of Qβ coat proteins where the N-terminal methionine is either cleaved or present are also within the scope of the present invention.

Further preferred virus-like particles of RNA-phages, in particular of Qβ, in accordance of this invention are disclosed in WO 02/056905, the disclosure of which is herewith incorporated by reference in its entirety.

Further RNA phage coat proteins have also been shown to self-assemble upon expression in a bacterial host (Kastelein, R A. et al., *Gene* 23: 245-254 (1983), Kozlovskaya, T M. et al., *Dokl. Akad. Nauk SSSR* 287: 452-455 (1986), Adhin, M R. et al., *Virology* 170: 238-242 (1989), Ni, C Z., et al., *Protein Sci.* 5: 2485-2493 (1996), Priano, C. et al., J. Mol. Biol. 249: 283-297 (1995)). The Qβ phage capsid contains, in addition to the coat protein, the so called read-through protein A1 and the maturation protein A2. A1 is generated by suppression at the UGA stop codon and has a length of 329 aa. The capsid of phage Qβ recombinant coat protein used in the invention is devoid of the A2 lysis protein, and contains RNA from the host. The coat protein of RNA phages is an RNA binding protein, and interacts with the stem loop of the ribosomal binding site of the replicase gene acting as a translational repressor during the life cycle of the virus. The sequence and structural elements of the interaction are known (Witherell, G W. & Uhlenbeck, O C. *Biochemistry* 28: 71-76 (1989); Lim F. et al., *J. Biol. Chem.* 271: 31839-31845 (1996)). The stem loop and RNA in general are known to be involved in the virus assembly (Golmohammadi, R. et al., *Structure* 4: 543-5554 (1996)).

In a further preferred embodiment of the present invention, the virus-like particle comprises, or alternatively consists essentially of or alternatively consists of recombinant proteins, or fragments thereof of a RNA-phage, wherein the recombinant proteins comprise, consist essentially of or alternatively consist of mutant coat proteins of RNA phages. In another preferred embodiment, the mutant coat proteins have been modified by removal of at least one lysine residue, more preferably of at least two lysine residues, by way of substitution, or by addition of at least one lysine residue by way of substitution. Alternatively, the mutant coat proteins have been modified by deletion of at least one lysine residue, more preferably of at least two lysine residues, or by addition of at least one lysine residue, more preferably of at least two lysine residues, by way of insertion.

In another preferred embodiment, the virus-like particle comprises, consists essentially of, or alternatively consists of recombinant proteins, or fragments thereof, of the RNA-bacteriophage Qβ, wherein the recombinant proteins comprise, consist essentially of, or alternatively consist of coat proteins having an amino acid sequence of SEQ ID NO:3, or a mixture of coat proteins having amino acid sequences of SEQ ID NO:3 and of SEQ ID NO: 4 or mutants of SEQ ID NO: 4 and wherein the N-terminal methionine is preferably cleaved.

In a further preferred embodiment of the present invention, the virus-like particle comprises, consists essentially of or alternatively consists of recombinant proteins of Qβ, or fragments thereof, wherein the recombinant proteins comprise, consist essentially of or alternatively consist of mutant Qβ coat proteins. In another preferred embodiment, these mutant coat proteins have been modified by removal of at least one lysine residue by way of substitution, or by addition of at least one lysine residue by way of substitution. Alternatively, these mutant coat proteins have been modified by deletion of at least one lysine residue, or by addition of at least one lysine residue by way of insertion.

Four lysine residues are exposed on the surface of the capsid of Qβ coat protein. Qβ mutants, for which exposed lysine residues are replaced by arginines can also be used for the present invention. The following Qβ coat protein mutants and mutant Qβ VLP's can, thus, be used in the practice of the invention: "Qβ-240" (Lys13-Arg; SEQ ID NO:6), "Qβ-243" (Asn 10-Lys; SEQ ID NO:7), "Qβ-250" (Lys 2-Arg, Lys13-Arg; SEQ ID NO:8), "Qβ-251" (SEQ ID NO:9) and "Qβ-259" (Lys 2-Arg, Lys16-Arg; SEQ ID NO:10). Thus, in further preferred embodiment of the present invention, the virus-like particle comprises, consists essentially of or alternatively consists of recombinant proteins of mutant Qβ coat proteins, which comprise proteins having an amino acid sequence selected from the group of a) the amino acid sequence of SEQ ID NO:6; b) the amino acid sequence of SEQ ID NO:7; c) the amino acid sequence of SEQ ID NO:8; d) the amino acid sequence of SEQ ID NO:9; and e) the amino acid sequence of SEQ ID NO:10. The construction, expression and purification of the above indicated Qβ coat proteins, mutant Qβ coat protein VLP's and capsids, respectively, are described in WO 02/056905. In particular is hereby referred to Example 18 of above mentioned application.

In a further preferred embodiment of the present invention, the virus-like particle comprises, consists essentially of or alternatively consists of recombinant proteins of Qβ, or fragments thereof, wherein the recombinant proteins comprise, consist essentially of or alternatively consist of a mixture of either one of the foregoing Qβ mutants and the corresponding A1 protein.

In a further preferred embodiment of the present invention, the virus-like particle comprises, or alternatively essentially consists of, or alternatively consists of recombinant proteins, or fragments thereof, of RNA-phage AP205.

The AP205 genome consists of a maturation protein, a coat protein, a replicase and two open reading frames not present in related phages; a lysis gene and an open reading frame playing a role in the translation of the maturation gene (Klovins, J., et al., *J. Gen. Virol.* 83: 1523-33 (2002)). AP205 coat protein can be expressed from plasmid pAP283-58 (SEQ ID NO: 15), which is a derivative of pQb10 (Kozlovska, T. M. et al., *Gene* 137:133-37 (1993)), and which contains an AP205 ribosomal binding site. Alternatively, AP205 coat protein may be cloned into pQb185, downstream of the ribosomal binding site present in the vector. Both approaches lead to expression of the protein and formation of capsids as described in Example 10. Vectors pQb10 and pQb185 are vectors derived from pGEM vector, and expression of the cloned genes in these vectors is controlled by the trp promoter (Kozlovska, T. M. et al., *Gene* 137:133-37 (1993)). Plasmid pAP283-58 (SEQ ID NO:15) comprises a putative AP205 ribosomal binding site in the following sequence, which is downstream of the XbaI site, and immediately upstream of the ATG start codon of the AP205 coat protein: tctagaATTTTCTGCGCACCCATCCCGGGTG-GCGCCCAAAGTGAGGAAAATCACatg (SEQ ID NO: 16). The vector pQb185 comprises a Shine Delagarno sequence downstream from the XbaI site and upstream of the start codon (tctagaTTAACCCAACGCGT AGGAGTCAGGCCatg (SEQ ID NO: 17), Shine Delagarno sequence underlined).

In a further preferred embodiment of the present invention, the virus-like particle comprises, or alternatively essentially consists of, or alternatively consists of recombinant coat proteins, or fragments thereof, of the RNA-phage AP205.

This preferred embodiment of the present invention, thus, comprises AP205 coat proteins that form capsids. Such proteins are recombinantly expressed, or prepared from natural sources. AP205 coat proteins produced in bacteria spontaneously form capsids, as evidenced by Electron Microscopy (EM) and immunodiffusion. The structural properties of the capsid formed by the AP205 coat protein (SEQ ID NO: 14) and those formed by the coat protein of the AP205 RNA phage are nearly indistinguishable when seen in EM. AP205 VLPs are highly immunogenic, and can be linked with antigens and/or antigenic determinants to generate vaccine constructs displaying the antigens and/or antigenic determinants oriented in a repetitive manner. High titers are elicited against the so displayed antigens showing that bound antigens and/or antigenic determinants are accessible for interacting with antibody molecules and are immunogenic.

In a further preferred embodiment of the present invention, the virus-like particle comprises, or alternatively essentially consists of, or alternatively consists of recombinant mutant coat proteins, or fragments thereof, of the RNA-phage AP205.

Assembly-competent mutant forms of AP205 VLPs, including AP205 coat protein with the subsitution of proline at amino acid 5 to threonine (SEQ ID NO: 18), may also be used in the practice of the invention and leads to a further preferred embodiment of the invention. These VLPs, AP205 VLPs derived from natural sources, or AP205 viral particles, may be bound to antigens to produce ordered repetitive arrays of the antigens in accordance with the present invention.

AP205 P5-T mutant coat protein can be expressed from plasmid pAP281-32 (SEQ ID No. 19), which is derived directly from pQb185, and which contains the mutant AP205 coat protein gene instead of the Qβ coat protein gene. Vectors for expression of the AP205 coat protein are transfected into *E. coli* for expression of the AP205 coat protein.

Methods for expression of the coat protein and the mutant coat protein, respectively, leading to self-assembly into VLPs are described in Examples 9 and 10. Suitable *E. coli* strains include, but are not limited to, *E. coli* K802, JM 109, RR1. Suitable vectors and strains and combinations thereof can be identified by testing expression of the coat protein and mutant coat protein, respectively, by SDS-PAGE and capsid formation and assembly by optionally first purifying the capsids by gel filtration and subsequently testing them in an immunodiffusion assay (Ouchterlony test) or Electron Microscopy (Kozlovska, T. M. et al., *Gene* 137:133-37 (1993)).

AP205 coat proteins expressed from the vectors pAP283-58 and pAP281-32 may be devoid of the initial Methionine amino-acid, due to processing in the cytoplasm of *E. coli*. Cleaved, uncleaved forms of AP205 VLP, or mixtures thereof are further preferred embodiments of the invention.

In a further preferred embodiment of the present invention, the virus-like particle comprises, or alternatively essentially consists of, or alternatively consists of a mixture of recombinant coat proteins, or fragments thereof, of the RNA-phage AP205 and of recombinant mutant coat proteins, or fragments thereof, of the RNA-phage AP205.

In a further preferred embodiment of the present invention, the virus-like particle comprises, or alternatively essentially consists of, or alternatively consists of fragments of recombinant coat proteins or recombinant mutant coat proteins of the RNA-phage AP205.

Recombinant AP205 coat protein fragments capable of assembling into a VLP and a capsid, respectively are also useful in the practice of the invention. These fragments may be generated by deletion, either internally or at the termini of the coat protein and mutant coat protein, respectively. Insertions in the coat protein and mutant coat protein sequence or fusions of antigen sequences to the coat protein and mutant coat protein sequence, and compatible with assembly into a VLP, are further embodiments of the invention and lead to chimeric AP205 coat proteins, and particles, respectively. The outcome of insertions, deletions and fusions to the coat protein sequence and whether it is compatible with assembly into a VLP can be determined by electron microscopy.

The particles formed by the AP205 coat protein, coat protein fragments and chimeric coat proteins described above, can be isolated in pure form by a combination of fractionation steps by precipitation and of purification steps by gel filtration using e.g. Sepharose CL-4B, Sepharose CL-2B, Sepharose CL-6B columns and combinations thereof. Other methods of isolating virus-like particles are known in the art, and may be used to isolate the virus-like particles (VLPs) of bacteriophage AP205. For example, the use of ultracentrifugation to isolate VLPs of the yeast retrotransposon Ty is described in U.S. Pat. No. 4,918,166, which is incorporated by reference herein in its entirety.

According to the present invention, one or more haptens may be attached to one subunit of the capsid of RNA phages coat proteins. The ability to couple several haptens per subunit of the capsid of the coat protein of RNA phages and in particular of Qβ capsid allows for the generation of a dense hapten array. Other viral capsids may be used for covalent attachment of haptens by way of chemical cross-linking, such for example a HBcAg modified with a lysine residue in its major immunodominant region (MIR; WO 00/32227). The distance between the spikes (corresponding to the MIR) of HBcAg is 50 Angströms (Wynne, S A. et al., *Mol. Cell* 3: 771-780 (1999)), and therefore an hapten array with distances shorter than 50 A cannot be generated Capsids of Qβ coat protein display a defined number of lysine residues on their surface, with a defined topology with three lysine residues pointing towards the interior of the capsid and interacting with the RNA, and four other lysine residues exposed to the exterior of the capsid. These defined properties favor the attachment of haptens to the exterior of the particle, and not to the interior where the lysine residues interact with RNA. Capsids of other RNA phage coat proteins also have a defined number of lysine residues on their surface and a defined topology of these lysine residues. Another advantage of the capsids derived from RNA phages is their high expression yield in bacteria, that allows the production of large quantities of material at affordable cost.

Another feature of the capsid of Qβ coat protein is its stability. Qβ subunits are bound via disulfide bridges to each other, covalently linking the subunits. Qβ capsid protein also shows unusual resistance to organic solvents and denaturing agents. Surprisingly, we have observed that DMSO and acetonitrile concentrations as high as about 30%, and Guanidinium concentrations as high as about 1 M could be used without affecting the stability or the ability to form hapten arrays of the capsid. Thus, theses organic solvents may be used to couple hydrophobic molecules, such as hormones, drugs and toxins. The high stability of the capsid of Qβ coat protein is an important feature pertaining to its use for immunization and vaccination of mammals and humans in particular. The resistance of the capsid to organic solvent allows the coupling of haptens not soluble in aqueous buffers.

Insertion of a cysteine residue into the N-terminal β-hairpin of the coat protein of the RNA phage MS-2 has been described in the U.S. Pat. No. 5,698,424, the reference of which is incorporated herein in its entirety. We note however, that the presence of an exposed free cysteine residue in the capsid may lead to oligomerization of capsids by way of disulfide bridge formation. Other attachments contemplated in the above U.S. patent involve the formation of disulfide bridges between the antigen and the Qβ particle. Such attachments are labile to sulfhydryl-moiety containing molecules.

The reaction between an initial disulfide bridge formed with a cysteine-residue on Qβ, and the antigen containing a free sulfhydryl residue releases sulfhydryl containing species other than the hapten. These newly formes sulfhydryl containing species can react again with other disulfide bridges present on the particle, thus establishing an equilibrium. Upon reaction with the disulfide bridge formed on the particle, the hapten may either form a disulfide bridge with the cysteine-residue from the particle, or with the cysteine-residue of the leaving group molecule which was forming the initial disulfide bridge on the particle. Moreover, the other method of attachment described, using a hetero-bifunctional cross-linker reacting with a cysteine on the Qβ particle on one side, and with a lysine residue on the antigen on the other side, may lead to a random orientation of the antigens on the particle.

We further note that, in contrast to the capsid of the Qβ and Fr coat proteins, recombinant MS-2 described in U.S. Pat. No. 5,698,424 is essentially free of nucleic acids, while RNA is packaged inside the two capsids mentioned above.

We describe new and inventive compositions allowing the formation of robust hapten arrays with variable hapten density. We show that very high epitope density can be achieved by attaching haptens to VLPs. Futher, the density and spacing of haptens can be modified by alterations in the number and type of residues with suitable first attachment sites. For example WO 02/056905 discloses a Qβ mutant coat protein with additional lysine residues, suitable for obtaining higher density arrays than observed with wild type Qβ coat protein. Further, the aforesaid application also discloses compositions suitable for simultaneous display of several hapten with appropriate spacing, and compositions wherein the addition of accessory molecules, enhancing solubility or modifiying the capsid in a suitable and desired way. Other Qβ coat protein mutants, forming capsids, which are virus-like particles, are disclosed in WO 02/056905 and are suitable for generating compositions of the invention. In particular, in occurrences where solubility of the hapten, and of the Qβ-hapten antigen array imposes a limit on the number of hapten residues that can be attached on the Qβ virus-like particle, mutants where lysine residues have been substituted for arginines, which do not have the same reactivity as lysine residues, can be used. When preparing these compositions, a high concentration of hapten, or hapten modified to comprise a second attachment site, can be used to achieve complete reaction at the lysine residues on the mutant Qβ virus-like particles, without generating potentially insoluble particles with a higher number of attached haptens, as would be the case when using the wt Qβ virus-like particle.

The crystal structure of several RNA bacteriophages has been determined (Golmohammadi, R. et al., *Structure* 4:543-554 (1996)). Using such information, one skilled in the art could readily identify surface exposed residues and modify bacteriophage coat proteins such that one or more reactive amino acid residues can be inserted. Thus, one skilled in the art could readily generate and identify modified forms of bacteriophage coat proteins which can be used in the practice of the invention. Thus, variants of proteins which form capsids or capsid-like structures (e.g., coat proteins of bacteriophage Qβ, bacteriophage R17, bacteriophage fr, bacteriophage GA, bacteriophage SP, and bacteriophage MS2) can also be used to prepare vaccine compositions of the invention.

Although the sequence of the variants proteins discussed above will differ from their wild-type counterparts, these variant proteins will generally retain the ability to form capsids or capsid-like structures. Thus, the invention further includes vaccine compositions which contain variants of proteins which form capsids or capsid-like structures, as well as methods for preparing such vaccine compositions, individual protein subunits used to prepare such vaccine compositions. Thus, included within the scope of the invention are variant forms of wild-type proteins which form ordered and repetitive hapten arrays (e.g., variants of proteins which form capsids or capsid-like structures) and retain the ability to associate and form capsids or capsid-like structures. Normally, C- an N-terminal trunction variants retain the ability to form virus like particles. As a result, variant forms including deletion, addition, or subsitution, chimeric forms, and naturally occuring variants are suitable components of the invention.

Bacterial Pili and pilin proteins. In another embodiment, the core particle of the invention comprises, preferably consists of, a bacterial pilus or pilus-like particle. The pilus particle comprises proteins, mutant proteins or fragments of pilin proteins produced by organisms including *Escherichia coli; Haemophilus influenzae; Neisseria meningitidis; Neisseria gonorrhoeae; Caulobacter crescentus; Pseudomonas stutzeri; Pseudomonas aeruginosa; Salmonella* spp; and *Vibrio cholera*. In a preferred embodiment, the pilin proteins or fragments thereof are selected from the group consisting of: a) Type 1 pilin proteins; and b) P-pilin proteins. In another embodiment, the pilin proteins are recombinant proteins, or the pilus or pilus-like particle comprises a mixture of recombinant and non-recombinant proteins. In yet an other embodiment, the pilus or pilus-like particle comprises type I pilin proteins or fragments thereof. In a further embodiment, the pilin proteins are mutant proteins, preferably proteins which have been modified by removal of at least one lysine residue by way of substitution, by addition of at least one lysine residue by way of substitution, by deletion of at least one lysine residue, or by addition of at least one lysine residue by way of insertion. In a preferred embodiment, the type I pilin proteins have an amino acid sequence as set forth in SEQ ID No: 2. In yet a further aspect, the invention provides a composition comprising the conjugate of the invention wherein the core particle comprises, preferably consists of, a bacterial pilus or pilus-like particle, and a pharmaceutically acceptable carrier.

In other embodiments, a bacterial pilin, a subportion of a bacterial pilin, or a fusion protein which contains either a bacterial pilin or subportion thereof is used to prepare vaccine compositions of the invention. Examples of pilin proteins include pilins produced by *Escherichia coli, Haemophilus influenzae, Neisseria meningitidis, Neisseria gonorrhoeae, Caulobacter crescentus, Pseudomonas stutzeri,* and *Pseudomonas aeruginosa*. The amino acid sequences of pilin proteins suitable for use with the present invention include those set out in GenBank reports AJ000636, AJ132364, AF229646, AF051814, AF051815, and X00981, the entire disclosures of which are incorporated herein by reference.

Bacterial pilin proteins are generally processed to remove N-terminal leader sequences prior to export of the proteins into the bacterial periplasm. Further, as one skilled in the art would recognize, bacterial pilin proteins used to prepare vaccine compositions of the invention will generally not have the naturally present leader sequence.

One specific example of a pilin protein suitable for use in the present invention is the P-pilin of *E. coli* (GenBank report AF237482). An example of a Type-1 *E. coli* pilin suitable for use with the invention is a pilin having he amino acid sequence set out in GenBank report P04128 (SEQ ID NO:2), which is encoded by nucleic acid having the nucleotide sequence set out in GenBank report M27603. The entire disclosures of these GenBank reports are incorporated herein by reference. Again, the mature form of the above referenced protein would generally be used to prepare vaccine compositions of the invention.

Bacterial pilins or pilin subportions suitable for use in the practice of the present invention will generally be able to associate to form non-natural molecular scaffolds. Methods for preparing pili and pilus-like structures in vitro are known in the art. Bullitt et al., *Proc. Natl. Acad. Sci. USA* 93:12890-12895 (1996), for example, describe the in vitro reconstitution of *E. coli* P-pili subunits. Further, Eshdat et al (*J. Bacteriol.* 148:308-314 (1981)) describe methods suitable for dissociating Type-1 pili of *E. coli* and the reconstitution of pili. In brief, these methods are as follows: pili are dissociated by incubation at 37° C. in saturated guanidine hydrochloride. Pilin proteins are then purified by chromatography, after which pilin dimers are formed by dialysis against 5 mM tris(hydroxymethyl)aminomethane hydrochloride (pH 8.0). Eshdat et al. also found that pilin dimers reassemble to form pili upon dialysis against the 5 mM tris(hydroxymethyl)aminomethane (pH 8.0) containing 5 mM $MgCl_2$.

Further, using, for example, conventional genetic engineering and protein modification methods, pilin proteins may be modified to contain a first attachment site to which a hapten is linked through a second attachment site. Alternatively, haptens can be directly linked through a second attachment site to amino acid residues which are naturally resident in these proteins. These modified pilin proteins may then be used in immunizing compositions of the invention.

Bacterial pilin proteins used to prepare compositions of the invention may be modified in a manner similar to that described herein for HBcAg. For example, cysteine and lysine residues may be either deleted or substituted with other amino acid residues and first attachment sites may be added to these proteins. Further, pilin proteins may either be expressed in modified form or may be chemically modified after expression. Similarly, intact pili may be harvested from bacteria and then modified chemically.

In another embodiment, pili or pilus-like structures are harvested from bacteria (e.g., *E. coli*) and used to form vaccine compositions of the invention. One example of pili suitable for preparing vaccine compositions is the Type-1 pilus of *E. coli*, which is formed from pilin monomers having the amino acid sequence set out in SEQ ID NO:2.

A number of methods for harvesting bacterial pili are known in the art. Bullitt and Makowski (*Biophys. J.* 74:623-632 (1998)), for example, describe a pilus purification method for harvesting P-pili from *E. coli*. According to this method, pili are sheared from hyperpiliated *E. coli* containing a P-pilus plasmid and purified by cycles of solubilization and $MgCl_2$ (1.0 M) precipitation. WO 02/056905 discloses harvesting and purification of Type I pili from bacteria that naturally produce pili, or into which a vector has been introduced encoding the fim operon responsible for pilus production.

Once harvested, pili or pilus-like structures may be modified in a variety of ways. For example, a first attachment site can be added to the pili to which haptens may be attached through a second attachment site. In other words, bacterial pili or pilus-like structures can be harvested and modified to form non-natural molecular scaffolds.

Pili or pilus-like structures may also be modified by the attachment of haptens in the absence of a non-natural first attachment site. For example, antigens or antigenic determinants could be linked to naturally occurring cysteine resides or lysine residues. In such instances, the high order and repetitiveness of a naturally occurring amino acid residue would guide the coupling of the antigens or antigenic determinants to the pili or pilus-like structures. For example, the pili or pilus-like structures could be linked to the second attachment sites of the haptens using a heterobifunctional cross-linking agent.

When structures which are naturally synthesized by organisms (e.g., pili) are used to prepare vaccine compositions of the invention, it will often be advantageous to genetically engineer these organisms so that they produce structures having desirable characteristics. For example, when Type-1 pili of *E. coli* are used, the *E. coli* from which these pili are harvested may be modified so as to produce structures with specific characteristics. Examples of possible modifications of pilin proteins include the insertion of one or more lysine residues, the deletion or substitution of one or more of the naturally resident lysine residues, and the deletion or substitution of one or more naturally resident cysteine residues (e.g., the cysteine residues at positions 44 and 84 in SEQ ID NO:2).

Further, additional modifications can be made to pilin genes which result in the expression products containing a first attachment site other than a lysine residue (e.g., a FOS or JUN domain). Of course, suitable first attachment sites will generally be limited to those which do not prevent pilin proteins from forming pili or pilus-like structures suitable for use in vaccine compositions of the invention. The ability of recombinant pilin proteins to form pili may be determined by a number of methods including electron microscopy.

Pilin genes which naturally reside in bacterial cells can be modified in vivo (e.g., by homologous recombination) or pilin genes with particular characteristics can be inserted into these cells. For examples, pilin genes could be introduced into bacterial cells as a component of either a replicable cloning vector or a vector which inserts into the bacterial chromosome. The inserted pilin genes may also be linked to expression regulatory control sequences (e.g., a lac operator).

In most instances, the pili or pilus-like structures used in vaccine compositions of the invention will be composed of single type of a pilin subunit. However, the compositions of the invention also include vaccines comprising pili or pilus-like structures formed from heterogenous pilin subunits. Pili or pilus-like structures composed of identical subunits will generally be used because they are expected to form structures which present highly ordered and repetitive antigen arrays.

Second attachment site. The preparation of molecular scaffolds with ordered and repetitive arrays is provided by the present including compositions of capsids of RNA phage coat proteins with a high epitope density. The nature of the hapten, and nature and location of the second attachment site on the hapten are important factors that may influence the means available to construct conjugates of the invention, and the effectiveness of those conjugates in inducing an immune response, as is understood by those of ordinary skill in the art.

A prerequisite for designing a second attachment site is the choice of the position at which it should be fused, inserted or generally engineered and attached. A skilled artisan would know how to find guidance in selecting the position of the second attachment site, and many factors may be considered relevant to this decision. The chemical and/or crystal structure of the hapten may provide information on the availability of domains or moieties on the molecule suitable for coupling. A reactive moiety or domain's accessibility to solvent may be a limiting factor in the kinetics of chemical coupling to a first attachment site. Groups suitable for coupling must be available, such as sulfhydryl residues. In general, in the case where immunization with a hapten is aimed at inhibiting the interaction of said hapten, which may also be a self-antigen, with its natural ligands, such as a receptor, the second attachment site will be added such that it allows generation of antibodies against the site of interaction with the natural ligands. Thus, the location of the second attachment site will selected such, that steric hindrance from the second attachment site or any linker or amino acid linker containing it, is avoided. In further embodiments, an antibody response directed at a site distinct from the interaction site of the hapten, which can also be a self-antigen with its natural ligand is desired. In such embodiments, the second attachment site may be selected such that it prevents generation of antibodies against the interaction site of said hapten with its natural ligands. Other factors of consideration include the nature of the hapten, its biochemical properties, such as pI, charge distribution, further modification. In general, flexible linkers are favored.

Other criteria in selecting the position of the second attachment site include the oligomerization state of the hapten, the site of oligomerization, the presence of a cofactor, the chemical reactivity of the hapten, and the availability of experimental evidence disclosing sites in the hapten structure and sequence where modification of the hapten is compatible with the function of the hapten, or with the generation of antibodies recognizing said hapten and preferably, blocking hapten function.

One method of attachment of haptens comprising a polypeptide linker to VLPs, and in particular to capsids of RNA phage coat proteins is the linking of a lysine residue on the surface of the capsid of RNA phage coat proteins with a sulfhydryl group residue on the polypeptide linker, such as is found in cysteine residues. Similarly, free sulfhydryl groups on haptens may also be effective attachment sites. Where an oxidized sulfhydryl groups must be in a reduced state in order to function as a second attachment site, reduction of may be achieved with e.g. DTT, TCEP or β-mercaptoethanol.

In one preferred embodiment of the invention, the hapten is synthesized in such a manner that it comprises a second attachment site which can react with the lysine residue on the surface of the capsid of RNA phage coat proteins.

According to the present invention, the epitope density on the capsid of RNA phage coat proteins can be modulated by the choice of cross-linker and other reaction conditions. For example, the cross-linkers Sulfo-GMBS and SMPH allow reaching high epitope density. Derivatization is positively influenced by high concentration of reactants, and manipulation of the reaction conditions can be used to control the number of antigens coupled to RNA phages capsid proteins, and in particular to Qβ capsid protein. In addition, the number of first attachment sites on the core particle is another factor affecting the density of the hapten array. In one embodiment of the present invention, we provide a Qβ mutant coat protein with additional lysine residues, suitable for obtaining higher density arrays.

Cross linking. Methods for linking the hapten to the core particle are well within the working knowledge of the practitioner of ordinary skill in the art, and numerous references exist to aid such a practitioner (e.g., Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997); Celis, J., ed., CELL BIOLGY, Academic Press, $2^{nd}$ edition, (1998); Harlow, E. and Lane, D., "Antibodies: A Laboratory Manual," Cold Spring Harbor Laboratory, Cold Spring Harbor, N.Y. (1988), all of which are incorporated herein by reference in their entirities.

Differing methods of achieving an association between the core particle and hapten are described herein and are further described in WO 02/056905. Methods include the JUN and FOS leucine zipper protein domains are utilized for the first and second attachment sites of the invention, respectively.

Preferred embodiments of the invention comprise the coupling of the non-natural molecular scaffold to the hapten by chemical cross-linking. There is a wide range of compounds which have been developed to facilitate cross-linking of proteins/peptides or conjugation of proteins to derivatized molecules, e.g., haptens. These include, but are not limited to, carboxylic acid derived active esters (activated compounds), mixed anhydrides, acyl halides, acyl azides, alkyl halides, N-maleimides, imino esters, isocyanates and isothiocyanates, which are known to those skilled in the art. These are capable of forming a covalent bond with a reactive group of a protein molecule. Depending upon the activating group, the reactive group is the amino group of a lysine residue on a protein molecule or a thiol group in a carrier protein or a modified carrier protein molecule which, when reacted, result in amide, amine, thioether, amidine urea or thiourea bond formation. One skilled in the art may identify further suitable activating groups, for example, in general reference texts such as Chemistry of Protein Conjugation and Cross-Linking (Wong (1991) CRC Press, Inc., Boca Raton, Fla.). Most reagents react preferentially with lysine side chain groups.

In some embodiments, the antigen is attached to the core particle by way of chemical cross-linking, using a heterobifunctional cross-linker. Several hetero-bifunctional cross-linkers are known in the art. In one embodiment, the heterobifunctional cross-linker contains a functional group which can react with the side-chain amino group of lysine residues of the core particle, and a functional group which can react with a cysteine residue or sulfhydryl group present on the hapten, made available for reaction by reduction, or engineered or attached on the hapten and optionally also made available for reaction by reduction. The first step of the procedure, called the derivatization, is the reaction of the core particle with the cross-linker. The product of this reaction is an activated core particle, also called activated carrier. In the second step, unreacted cross-linker is removed using usual methods such as gel filtration or dialysis. In the third step, the antigen is reacted with the activated core particle, and this step is called the coupling step. Unreacted antigen may be optionally removed in a fourth step.

In an alternative embodiment, the hapten is derivatized with an active moiety suitable for cross linking to the first attachment site, generating an activated hapten. Such derivatization may occur on an isolated hapten or via a chemical synthesis. The activated hapten is then reacted with the core particle such that coupling occurs.

Several hetero-bifunctional cross-linkers are known in the art. These include the cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available, for example from the Pierce Chemical Company (Rockford, Ill., USA), and having one functional group reactive towards amino groups and one functional group reactive towards SH residues. The above mentioned cross-linkers all lead to formation of a thioether linkage. Another class of cross-linkers suitable in the practice of the invention is characterized by the introduction of a disulfide linkage between the hapten and the core particle upon coupling. Cross-linkers belonging to this class include for example SPDP and Sulfo-LC-SPDP (Pierce). The extent of derivatization of the core particle with cross-linker can be influenced by varying experimental conditions such as the concentration of each of the reaction partners, the excess of one reagent over the other, the pH, the temperature and the ionic strength, as is well known from reaction theory in the field of organic chemistry. The degree of coupling, i.e. the amount of hapten per carrier can be adjusted by varying the experimental conditions described above to match the requirements of the vaccine. Solubility of the hapten may impose a limitation on the amount of antigen that can be coupled on each subunit, and in those cases where the obtained vaccine is insoluble, reducing the amount of antigens per subunit is beneficial.

In one specific embodiment the chemical agent is the heterobifunctional cross-linking agent ε-maleimidocaproic acid N-hydroxysuccinimide ester (Tanimori et al., *J. Pharm. Dyn.* 4:812 (1981); Fujiwara et al., *J. Immunol. Meth.* 45:195 (1981)), which contains (1) a succinimide group reactive with amino groups and (2) a maleimide group reactive with SH groups. A heterologous protein or polypeptide of the first attachment site may be engineered to contain one or more lysine residues that will serve as a reactive moiety for the succinimide portion of the heterobifunctional cross-linking agent. Once chemically coupled to the lysine residues of the heterologous protein, the maleimide group of the heterobifunctional cross-linking agent will be available to react with the SH group of a cysteine residue on the antigen or antigenic determinant. Antigen or antigenic determinant preparation in this instance may require the engineering of a sulfhydryl residue as the second attachment site so that it may be reacted to the free maleimide function on the cross-linking agent bound to the non-natural molecular scaffold first attachment sites. Thus, in such an instance, the heterobifunctional cross-linking agent binds to a first attachment site of the non-natural molecular scaffold and connects the scaffold to a second binding site of the antigen or antigenic determinant.

Other methods of coupling the hapten to the core particle include methods wherein the hapten is cross-linked to the core particle using carbodiimide compounds. These include the carbodiimide EDC (1-(3-dimethylaminopropyl)-3-ethylcarbodiimide hydrochloride), which can optionally also be used with N-hydroxy-succinimide NHS in the reaction. In one method, EDC is mixed with a hapten containing a free carboxylic acid, then added to the protein carrier. In other methods, the hapten is attached to the core particle using a homo-bifunctional cross-linker such as glutaraldehyde, DSG, $BM[PEO]_4$, $BS^3$, (Pierce Chemical Company, Rockford, Ill., USA) or other known homo-bifunctional cross-linkers with functional groups reactive towards amine groups or carboxyl groups of the core particle.

Additional cross-linking methods and cross-linkers, suitable for attaching a hapten to a core particle and a virus-like particle, respectively, as well as guidance on performing the coupling reactions and on the use of chemical cross-linkers and chemical cross-linking procedures can be found in Hermanson, G. T. in *Bioconjugate Techniques*, Academic Press Inc., San Diego, Calif., USA.

Further methods of binding the core particle to a hapten include methods where the core particle is biotinylated, and the hapten linked to streptavidin, or methods wherein both the hapten and the core particle are biotinylated. In this case, the hapten may be first bound to streptavidin or avidin by adjusting the ratio of antigen to streptavidin such that free binding sites are still available for binding of the core particle, which is added in the next step. Alternatively, all components may be mixed in a "one pot" reaction. Other ligand-receptor pairs, where a soluble form of the receptor and of the ligand is available, and are capable of being cross-linked to the core particle or the hapten, may be used as binding agents for binding the hapten to the core particle.

Haptens. In one aspect, the invention provides ordered, repetitive hapten arrays suitable for immunization against haptens. Preferred haptens are hormones, drugs and toxic compounds. More preferred are drugs, especially addictive drugs. Immune responses against said drugs, hormones and toxic compounds may be used to protect an individual at risk of exposure to said compounds, as therapy in an individual so exposed, or so as to prevent or treat addictions.

Representative hormones include, but are not limited to, progesterone, testosterone, estrogen, melanin stimulating hormone, cortisone, follicle stimulating hormone, adrenalin, and noradrenalin. Immune responses against said hormones may be used in therapies against melanoma; cancers of the reproductive organs, such as breast, ovarian, uterine, testicular, and cervical cancers; and in conditions where alteration of hormone levels is desired such as for contraception.

Representative toxic compounds include, but are not limited to, the natural products of toxic plants, animals, and microorganisms; these include but are not limited to aflatoxin, ciguautera toxin, and tetrodotoxin. Representative toxic compounds produced artificially, or as a result of metabolism include antibiotics (e.g vancomycin and the like), anticancer compounds (eg vinblastine and the like) and chemical warfare agents (eg. botulinus toxin, sarin, tabun, soman, VX and the like). An aspect of the invention includes the production of antibodies against toxic metabolites of commonly used pharmaceutical agents, such that an individual may continue to receive the beneficial effects of a pharmaceutical agents without side effects associated with toxic metabolites.

The selection of antigens or antigenic determinants for compositions and methods of treatment for drug addiction, in particular recreational drug addiction, would be known to those skilled in the medical arts treating such disorders. Representative examples of such antigens or antigenic determinants include, for example, opioids and morphine derivatives such as codeine, fentanyl, heroin, morphium and opium; relaxants such as diazepam; stimulants such as amphetamine, cocaine, MDMA (methylenedioxymethamphetamine), methamphetamine, methylphenidate and nicotine; hallucinogens such as PCP, LSD, mescaline and psilocybin; cannabinoids such as hashish and marijuana; as well as the desipramine/imipramine class of drugs and the nortriptyline/amitriptyline class of drugs. Therapy for nicotine addiction may also target nicotine metabolites including nornicotine and cotinine, both of which have longer half lives than nicotine, have pharmacologic and neuropharmacologic affects similar to nicotine and may be addictive.

In the above embodiments, it is not necessary that the immunizing hapten comprising the entire molecule of hormone, drug, or toxin. Suitable immune responses against the drug, hormone or toxin of interest may be generated by the use of fragments of the drug, hormone or toxin, or related chemical structures.

The invention embodies different sites of linkage and means of linkage of the hapten to the carrier, and have been illustrated both earlier in the invention, and by reference to the examples. Preferred sites and means of linkage may be determined on the basis of prior experience, theory and by routine experimentation.

Nicotine and nicotine metabolites. Immune responses suitable for nicotine may be generated by haptens coupled to the core particle either via the pyridine or pyrrolidine ring. In one embodiment, 6-(carboxymethylureido)-(±)-nicotine (CMU-Nic) conjugate is synthesized from 6-amino-(±)-nicotine, which is reacted with ethyl isocyanoacetate to form 6-(carboxyethylureido)-(±)-nicotine, and hydrolysis by lithium hydroxide to form CMUNic as described (Hieda et al *Int J Pharmacol* 22:809-819 (2000)), the reference to which is incorporated herein in its entirety. The hapten is conjugated to the core particle via the terminal carboxyl group, which may be activated using e.g. 1-ethyl-3-(3-dimethylaminopropyl) carbodiimide HCl. In another embodiment, 6-amino-(±)-nicotine is coupled to carrier proteins as described by WO 99/61054, incorporated herein by reference in its entirety.

In another embodiment of the present invention, trans-3'-aminomethylnicotine conjugate is prepared by trans-3'-hydroxymethylnicotine alcohol via the tosylate as described by Cushman and Castignoli (*J Org Chem* 37:1268-1271 (1972)) the reference to which is incorporated herein in its entirety. The hapten is conjugated to the core particle through a succinic acid linker using 1-ethyl-3-(3-dimethylaminopropyl) carbodiimide HCl (EDAC) to activate the linker's carboxylic acid group.

In a related embodiment, 3'-linkages to nicotine haptens are performed by first generating trans-3'-hydroxymethylnicotine which is reacted with succinic anhydride to yield the succinylated hydroxymethylnicotine (O-succinyl-3'-hydroxymethyl-nicotine). This product is then mixed with EDAC and the core particle for carbodiimide-activated coupling, as described by Langone and Van Vunakis (*Methods Enzymol.* 84:628-640 (1982)) the reference to which is incorporated herein in its entirety. In another embodiment, trans-4'-carboxycotinine is similarly activated with EDAC for coupling to a protein carrier.

In one embodiment, a nicotine hapten is coupled via the 1-position Nitrogen by conversion to the aminoethylpyridinium derivative, S-1-(b-aminoethyl)nicotinium chloride dihydrochloride, which is then coupled to a core particle in the presence of 1-cyclohexyl-3-(2-morpholinoethyl)-carbodiimide metho-p-toluenesulfonate as described Noguchi et al. (*Biochem Biophys Res Comm.* 83:83-86 (1978)) the reference to which is incorporated herein in its entirety. In a related embodiment, Cotinine is conjugated to core particles using the same general approach, via formation of S-1-(b-aminoethyl)cotinium chloride hydrochloride.

In one embodiment, a nicotine hapten is coupled via the 1'-position as described by Isomura et al. (*J. Org Chem* 66:4115-4121 (2001), the reference to which is incorporated herein in its entirety, via formation of N-[1-oxo-6-[(2S)-2-(3-pyridyl)-1-pyrrolidinyl]hexyl]-β-alanine. This activated hapten is then coupled to a protein carrier. In three other embodiments, conjugates are formed between the first attachment site on a protein core particle and the cotinine hapten 4-oxo-4-[[6-[(5S)-2-oxo-5-(3-pyridinyl)-1-pyrrolidinyl]]hexyl] amino]-butanoic acid, or the nornicotine haptens (2S)-2-(3-pyridinyl)-1-pyrrolidinebutanoic acid phenylmethyl ester or (2R)-2-(3-pyridinyl)-1-pyrrolidinebutanoic acid phenylmethyl ester.

In one embodiment, cotinine 4'-carboxylic acid is covalently bound to carriers at lysine as described by Bjerke et al. (J. Immunol. Methods, 96, 239-246 (1987)) the reference to which is incorporated herein in its entirety.

Nicotine haptens may be conjugated to carrier protein via a linker at the 6-position of nicotine. Along these lines, the following haptens are used in embodiments of the present invention N-succinyl-6-amino-(.+−.)-nicotine; 6-(.sigma.-aminocapramido)-(.+−.)-nicotine and 6-(.sigma.-aminocapramido)-(.+−.)-nicotine, as described (Castro et al. Eur. J. Biochem., 104, 331-340 (1980); Castro et al. in Biochem. Biophys. Res. Commun. 67, 583-589 (1975); Castro et al. Res. Commun Chem. Path. Pharm. 51, 393-404 (1986)), which is incorporated by reference herein in its entirety.

In other embodiments of the invention, nicotine haptens are conjugated via the 3',4', or 5' position via succinylation of aminomethylnicotine, activation with EDC and subsequent mixture with the carrier, as described by U.S. Pat. No. 6,232, 082, the reference to which is incorporated herein in its entirety. In other embodiments, aminomethyl nicotine is conjugated via polyglutamic acid-ADH to the core particle. In other embodiments, conjugates are formed from acetyl nicotine and aldehydo nicotine derivatized at the 3',4', or 5' positions.

In other embodiments, hapten carrier conjugates comprise 5- and 6-linkages of nicotine, including 5-(1-methyl-2-pyrrolidinyl)-2- or 3-pyridinyl-conjugates and 5-(N-methyl-2-pyrrolidinyl)-2- or 3-pyridinyl-conjugates. The construction of the haptens for these conjugates is described in WO 99/61054, the reference to which is incorporated herein in its entirety. In other embodiments, 5- and 6-amino nicotine are utilized as starting materials that are further derivatized at the amino group to add, typically, carbon chains that terminate in a suitably reactive group including amines and carboxylic acids. These haptens are then suitable for conjugation to core particles of the present invention. In other embodiments, 5- or 6-bromonicotine is used as a suitable starting material for reaction with alkynes leading to the addition of unsaturated carbon groups with a chain which terminate with moeities suitable for coupling, including amines and carboxylic acids, that allow conjugation to the core particle.

Other embodiments of the present invention comprise conjugates comprising nicotine haptens conjugated at the 1, 2, 4, 5, 6, or 1' positions of the nicotine, as described by Swain et al. (WO 98/14216), herein incorporated by reference in its entirety.

Other embodiments of the present invention comprise conjugates comprising nicotine haptens as described by Janda et al. (WO 02/058635).

Further embodiments comprise conformationally constrained nicotine haptens as described in Meijler et al. (J. Am. Chem. Soc, 2003, 125, 7164-7165).

Cocaine and related drugs. The present invention provides conjugates, compositions and methods comprising cocaine conjugated to a core particle. In one group of embodiments, the diazonium salts of benzoyl cocaine and benzoyl ecognine are coupled to carrier proteins. In other embodiements the para-imino ester derivatives of cocaine and norcocaine are conjugated to core particles. Haptens suitable for these embodiments are described in U.S. Pat. Nos. 3,88,866, 4,123,431 and 4,197,237 the references to which are incorporated herein in their entireties. Conjugates of cocaine using the para-position of the phenyl ring of various cocaine derivatives show increased stability to hydrolysis by the introduction of an amide bond.

Other embodiments of the present invention comprise cocaine haptens described by U.S. Pat. No. 5,876,727, the reference to which is incorporated herein in its entirety.

In one embodiment, precursors of the conjugates of the instant invention are synthesized by acylating ecgonine methyl ester with bromoacetyl bromide in DMF in the presence of two equivalents of diisopropylethylamine. The product is then coupled to the thiol group of a thiolated carrier protein to obtain a conjugate.

In another embodiment, precursors of the conjugates of the instant invention are synthesized by succinylating ecgonine methyl ester with succinic anhydride in DMF in the presence of one equivalent of triethylamine. The product is then coupled to the amino group of a lysine residue of a carrier protein to obtain a conjugate. In one embodiment, precursors of the conjugates of the instant invention are synthesized by reacting norcocaine with succinic anhydride in methylene chloride in the presence of two equivalents of triethylamine. In other emobidments precursors of the conjugates of the instant invention are synthesized by reacting a solution of norcocaine monoactivated succinic acid and triethylamine to form succinylated norcocaine. In either case, the resulting succinyl norocaine consists of a mixture of at least two isomers, namely the exo and endo forms of the succinyl group. In these embodiments succinyl norocaine is then be coupled to the .epsilon.-amino group of a lysine residue of a carrier protein using EDC to obtain a conjugate. In an alternative embodiment, the coupling reaction is carried out using a pre-activated succinylated norcocaine derivative. That is, the intermediate can be isolated and characterized. The pre-activated succinylated norcocaine derivative is synthesized by reacting 4-hydroxy-3-nitrobenzene sulfonic acid sodium salt with succinylated norcocaine in the presence of dicyclohexylcarbodiimide (DCC) and DMF. The product is conjugated to the amino group of a lysine residue of a carrier protein to obtain a conjugate.

In one alternative embodiment, compounds of the present invention are synthesized by reacting succinylated norcocaine with N-hydroxysuccimide in the presence of ethyl chloroformate, N-methylmorpholine (NMM) and DMF. The product is then coupled to the amino group of a lysine residue of a carrier protein to obtain a conjugate.

In one embodiment, compounds of the instant invention are synthesized by reacting thionyl chloride with succinylated norcocaine. The product is then conjugated to a carrier protein to obtain a conjugate. In another embodiment, compounds of the instant invention are synthesized by reacting succinylated norcocaine with HATU in DMF and diisopropylethylamine as outlined by Carpino ((1993) J. Am. Chem. Soc. 115:4397-4398) the reference to which is incorporated herein in its entirety. The product is added to an aqueous solution containing the carrier protein to obtain a conjugate.

In another embodiment, compounds of the invention are synthesized by reacting succinylated norcocaine with PyBroP in DMF and diisopropylethylamine. The product is added to an aqueous solution containing the carrier protein to obtain a conjugate. In a related embodiment the carrier protein is succinylated with succinic anhydride in borate buffer. The product is then coupled to norcocaine in the presence of EDC to obtain a conjugate.

In another embodiment, reduction of the free acid of coacaine in benzoyl ecgonine to its corresponding primary alcohol, is achieved using borane-dimethylsulfide complex. The alcohol is reacted with succinic anhydride in DMF, the product of which is then conjugated to the free amino acid group of a carrier protein in the presence of EDC to obtain a conjugate.

In another embodiment, compounds of the instant invention are synthesized by conjugating benzoyl ecgonine to the amino group of a lysine residue of a carrier protein in the presence of EDC to obtain a conjugate.

In one embodiment, the precursor of the conjugates is synthesized by acylating racemic nornicotine with succinic anhydride in methylene chloride in the presence of two equivalents of diisopropylethylamine. The product of this reaction is then coupled to the lysine residue of a carrier protein using HATU to obtain the conjugate. In another embodiment, selectively alkylating the pyridine nitrogen in (S)-(-)-nicotine in anhydrous methanol, with ethyl 3-bromobutyrate, 5-bromovaleric acid, 6-bromohexanoic acid or 8-bromooctanoic acid yield products suitable for conjugation to a carrier protein using HATU.

Compositions, Vaccines, and the Administration Thereof, and Methods of Treatment As discussed herein, the invention provides compositions which may be used for preventing and/or treating diseases or conditions. The invention further provides vaccination methods for preventing and/or treating diseases or conditions in individuals. In a preferred embodiment, compositions stimulate an immune response leading to the production of immune molecules, including antibodies, that bind to organic molecules. The invention further provides vaccination methods for preventing and/or treating diseases or conditions in individuals.

The nature or type of immune response is not a limiting factor of this disclosure. The desired outcome of a therapeutic or prophylactic immune response may vary according to the disease, according to principles well known in the art. For example, a vaccine against an inhaled drug (eg nicotine, cocaine) may be designed to induce high titres of serum IgG and also of secreted sIgA antibodies in the respiratory epithelium, thus binding nicotine both in the respiratory tract and within the bloodstream. By comparison, titres of sIgA antibodies are presumably less relevant when targeting an injected drug of abuse (eg heroin). However, a vaccination methodology against an injected drug of abuse that results in high serum titres as well as sIgA will nontheless be effective, so long as serum titres are sufficient.

The invention comprises vaccines sufficient to cure or prevent a disease or condition or addiction. The invention further comprises vaccines that reduce the number, severity or duration of symptoms; and vaccine compositions effective in reducing the number of individuals in a population with symptoms. The invention comprises compositions with effects upon the immune system that may aid in the treatment of a disease, as one facet in an overall therapeutic intervention against a disease. Given the notably complex nature of addiction, the invention comprises compositions that aid in therapy against drug addiction but are accompanied by psychiatric, behavioural, social and legal interventions.

Furthermore, it may be desired to stimulate different types of immune response depending on the disease, and according to principles known in the art. It is well known, for example, that some immune responses are more appropriate for a particular antigen than other immune responses. Some immune responses are, indeed, inappropriate and can cause pathology, such as pathologic inflammation.

The nature of the immune response can be affected by the nature of the antigen, route of introduction into the body, dose, dosage regimen, repetitive nature of the antigen, host background, and signalling factors of the immune system. Such knowledge is well known in the art. As such, an immune response may be tailored by the application of both art known theory and routine experimentation.

Furthermore, the invention embodies the use of differing core particles during the course of vaccination against a drug or drugs. Individuals who develop strong immune responses against core particles such as e.g. pili, may be immunized with compositions comprising the same hapten but differing in core particle.

While not wishing to be bound by theory or any particular mechanistic explanation for operation of the present invention, the conjugates of the present invention provide particular novel and surprising advantages as components of pharmaceutical compositions to generate an immune response, and particularly as vaccines. Other carriers known in the art including BSA, keyhole limpet hemocyanin, tetanus toxoid, bacterial outermembrane proteins, cholera toxin, and *Pseudomonas aeruginosa* Exotoxin A may be inappropriate for use in an individual, and in particular a human. The aforementioned carriers may induce allergic reactions, or stimulate pathologic immune responses (for example, cholera toxin, KLH, BSA). The aforementioned carriers may require the presence of adjuvants such as complete Freunds adjuvant, now considered inappropriate for use in humans. A number of the carriers may be components of current vaccines (for example, tetanus toxiod, cholera toxin, Exotoxin A). As such, an individual may possess a high level of pre-existing immunity to these carriers, such that immunization with an antigen-carrier conjugate will induce a relatively greater immune response to the carrier than to the novel antigen. For these reasons, individually or as a whole, the conjugates and compositions of the present invention represent a useful improvement over the above-described carrier proteins. The preseent invention demonstrates the use of Nicotine-Qβ VLP conjugate composition to stimulate an immune response against nicotine without the use of complete Freund's adjuvant and without evidence of pathologic immune responses.

In the use of the embodiments of the invention, haptens conjugated to core particles can be taken up by antigen presenting cells and thereby stimulate T-cell help to induce immune response. T helper cell responses can be divided into type 1 ($T_H1$) and type 2 ($T_H2$) T helper cell responses (Romagnani, *Immunol. Today* 18:263-266 (1997)). $T_H1$ cells secrete interferon-gamma and other cytokines which trigger B cells to produce IgG1-3 antibodies. In contrast, a critical cytokine produced by $T_H2$ cells is IL-4, which drived B cells to produce IgG4 and IgE. In many experimental systems, the development of $T_H1$ and $T_H2$ responses is mutually exclusive since $T_H1$ cells suppress the induction of $T_H2$ cells and vice versa. Thus, antigens that trigger a strong $T_H1$ response simultaneously suppress the development of $T_H2$ responses and hence the production of IgE antibodies. Interestingly, virtually all viruses induce a $T_H1$ response in the host and fail to trigger the production of IgE antibodies (Coutelier et al., *J. Exp. Med.* 165:64-69 (1987)). Antibodies of the IgE isotype are important components in allergic reactions. Mast cells bind IgE antibodies on their surface and release histamines and other mediators of allergic response upon binding of specific antigen to the IgE molecules bound on the mast cell surface. The isotype pattern typical of $T_H1$ responses is not restricted to live viruses but has also been observed for inactivated or recombinant viral particles (Lo-Man et al., *Eur. J. Immunol.* 28:1401-1407 (1998)). Thus, by using the processes of the invention (e.g., AlphaVaccine Technology), viral particles can be decorated with various hapten and used for immunization. Due to the resulting "viral structure" of the hapten, a $T_H1$ response will be elicited, "protective" IgG1-3 antibodies will be produced, and the production of IgE antibodies which cause allergic reactions will be prevented. Thus, the invention embodies compositions capable of inducing preferred immune responses, notably $T_H1$ type responses. Futher, the invention embodies the use of compositions of the invention to counter allergic reactions induced by alternative vaccines against haptens of interest.

A further advantageous feature of the present invention is that haptens may be presented on the in regular, repetitive arrays that are able to induce efficient immune responses both with and without T-cell help. This feature of the invention is particularly advantageous.

Unlike isolated proteins, viruses induce prompt and efficient immune responses in the absence of any adjuvants both with and without T-cell help (Bachmann & Zinkernagel, Ann. Rev. Immunol: 15:235-270 (1997)). Although viruses often consist of few proteins, they are able to trigger much stronger immune responses than their isolated components. For B-cell responses, it is known that one crucial factor for the immunogenicity of viruses is the repetitiveness and order of surface epitopes. Many viruses exhibit a quasi-crystalline surface that displays a regular array of epitopes which efficiently crosslinks epitope-specific immunoglobulins on B cells (Bachmann & Zinkernagel, Immunol. Today 17:553-558 (1996)). This crosslinking of surface immunoglobulins on B cells is a strong activation signal that directly induces cell-cycle progression and the production of IgM antibodies. Further, such triggered B cells are able to activate T helper cells, which in turn induce a switch from IgM to IgG antibody production in B cells and the generation of long-lived B cell memory—the goal of any vaccination (Bachmann & Zinkernagel, Ann. Rev. Immunol. 15:235-270 (1997)). The present invention provides one way to improve the efficiency of vaccination by increasing the degree of repetitiveness of the hapten to be used for immunization, through binding of the hapten to the core particles. As previously noted, the invention provides for compositions comprising core particle modified to alter the number and or arrangement of the first attachment sites.

As will be understood by one of ordinary skill in the art, when conjugates of the present invention are administered to an individual, they may be in a composition which contains salts, buffers, adjuvants and other substances, excipients or carriers which are desirable for improving the efficacy of the composition. Examples of materials suitable, or acceptable, for use in preparing pharmaceutical compositions are provided in numerous sources including REMINGTON'S PHARMACEUTICAL SCIENCES (Osol, A, ed., Mack Publishing Co., (1990)).

Compositions of the invention are said to be "pharmacologically acceptable" if their administration can be tolerated by a recipient individual. Further, the compositions of the invention will be administered in a "therapeutically effective amount" (i.e., an amount that produces a desired physiological effect).

The compositions of the present invention may be administered by various methods known in the art, but will normally be administered by injection, infusion, inhalation, oral administration, or other suitable physical methods. The compositions may alternatively be administered intramuscularly, intravenously, transmucosally, transdermally or subcutaneously. Components of compositions for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

In one specific embodiment, a human with nicotine addiction is immunized with 5 to 500 μg, preferably 25 to 200 μg, more preferably 50 to 100 μg, most preferably 100 μg of Nic-Qβ conjugate, with boosts at 3 weeks and again at 6 weeks, more preferably with boosts at 4 weeks and again at 8 weeks. Routes of immunizations can comprise intramuscular, subcutaneous, intradermal, transdermal, or intravenous injections. Two weeks after immunization, the immune response is monitored with kits as described elsewhere herein. The resulting immune response is specific for nicotine and comprises high serum IgG, and is sufficient to inhibit nicotine uptake into the brain. The resulting immune response is long lasting and thus the individual does not experience pleasurable effects from nicotine, and ceases nicotine use. Those skilled in the art will know from the measured immune response whether additional immunizations will be needed to maintain nicotine specific IgG levels. In an alternative embodiment of the present invention the nicotine-hapten carrier conjugates of the invention are administered by intranasal vaccination. This type of administration leads to high antibody titers encompassing IgA as indicated in the examples.

In a further embodiment of the invention, a pharmaceutical composition is provided for treating nicotine addiction, palliating nicotine withdrawal symptoms, facilitating smoking cessation or preventing relapse comprising a therapeutically effective combination of the vaccine composition of the invention and an additional agent. In one embodiment, the additional agent is selected from the group consisting of: anti-depressant; nicotine receptor modulator; cannabinoid receptor antagonist; opioid receptor antagonist; monoamine oxidase inhibitor; anxiolytic or any combination of these agents. Preferably, the additional agent is an anti-depressant selected from the group consisting of bupropion, doxepin, desipramine, clomipramine, imipramine, nortriptyline, amitriptyline, protriptyline, trimipramine, fluoxetine, fluvoxamine, paroxetine, sertraline, phenelzine, tranylcypromine, amoxapine, maprotiline, trazodone, venlafaxine, mirtazapine, their pharmaceutically active salts and their optical isomers. In a very preferred embodiment, the anti-depressant is either bupropion or a pharmaceutically acceptable salt thereof, or nortriptyline or a pharmaceutically acceptable salt thereof.

In another embodiment, the additional agent is a nicotine receptor modulator selected from the group consisting of mecamylamine, SSR591813, amantadine, pempidine, dihydro-beta-erythroidine, hexamethonium, erysodine, chlorisondamine, trimethaphan camsylate, tubocurarine chloride, d-tubocurarine, varenicline, their pharmaceutically acceptable salts and their optical isomers. In a very preferred embodiment, the nicotine receptor modulator is mecamylamine or a pharmaceutically acceptable salt thereof. In another preferred embodiment, the nicotine receptor modulator is varenicline or a pharmaceutically acceptable salt thereof.

In one embodiment, the present invention comprises a method of treating tobacco addiction or nicotine addiction, palliating nicotine withdrawal symptoms, preventing relapse or facilitating smoking cessation comprising the step of administering to a patient the vaccine composition of the invention and an additional agent. In a preferred embodiment, the vaccine composition is administered intranasally, orally, subcutaneously, transdermally, intramuscularly or intravenously, and wherein said additional agent is administered orally or via a transdermal patch. In a more preferred embodiment, the vaccine composition of the invention comprises O-succinyl-3'-hydroxymethyl-nicotine conjugated to Qβ virus like particle.

Anti-depressants, nicotine receptor agonists and antagonists, cannabinoid and opioid receptor antagonists, monoamine oxidase inhibitors and anxiolytics are able to relieve certain symptoms during smoking cessation such as withdrawal, craving, depression, irritability, anergia, amotivation, appetite changes, nausea and hypersomnia. They mainly act directly on receptors in the brain. Furthermore, weight increase upon smoking cessation is a major concern for a number of people. Vaccination inhibits the uptake of the nicotine into the brain and thus inhibits its rewarding effects. It does not inhibit withdrawal symptoms but inhibits the reinforcement of nicotine addiction upon a slip. Therefore, a combination of vaccination and the use of anti-depressants, nicotine receptor antagonists, cannabinoid receptor antagonists, monoamine oxidase inhibitors and anxiolytics and furhter drugs inhibiting weight gain is beneficial for aid in smoking cessation and relapse prevention.

Anti-depressants are used to treat symptoms of nicotine withdrawal and aid smoking cessation. One such anti-depressant is bupropion and a sustained-release formulation of bupropion HCl under the tradename Zyban is marketed as an aid for smoking cessation. The mechanism of action of bupropion is presumed to involve inhibition of neural re-uptake of dopamine and/or norepinephrine. As dopamine has been associated with the rewarding effects of addictive substances, such as nicotine, inhibition of the norepinephrine uptake was contemplated to induce a decrease of withdrawal symptoms. Methods to produce bupropion and pharmaceutically acceptable salts thereof are disclosed in U.S. Pat. Nos. 3,819,706 and 3,885,046. Methods to produce optically pure (+)-bupropion and pure (−)-bupropion have been disclosed (Castaldi G, et al., J. Org. Chem., 1987, 52:3018, Musso et al., 1993, Chirality 5: 495-500).

A preferred embodiment of the invention envisages the combined treatment of subjects for aid in smoking cessation or relapse prevention by vaccination using nicotine-VLP conjugates, preferentially nicotine-Qb conjugates, and administering bupropion, preferably bupropion hydrochloride. The amount of bupropion to be administered is formulated so as to provide a initial dose of about 150 mg per day for 6 days which is then followed by a dose of 300 mg per day.

Nortriptyline is used to treat depressions and has also been shown to be active in aiding smoking cessation (da Costa et al., 2002, Chest, 122, 403-408). Methods to produce nortryptyline are known to those skilled in the art. A preferred embodiment of the invention envisages the combined treatment of subjects for aid in smoking cessation or relapse prevention by vaccination using nicotine-VLP conjugates, preferentially nicotine-Qb conjugates, and administering nortriptyline. Nortriptyline is administered in a dose of 10-150 mg, most preferably 75 mg per day.

Additional anti-depressants contemplated for combination with vaccination include: doxepin, fluoxetine, desipramine, clomipramine, imipramine, amitriptyline, trimipramine, fluvoxamine, proxetine, sertraline, phenelzine, tranylcypromine, amoxapine, maprotiline, trazodone, venlafaxine, mirtrazapine, their pharmaceutically active salts or their optical isomers.

Nicotine receptor agonists and antagonists attenuate the reward received by tobacco usage by blocking the receptors.

Varenicline tartrate is a further selective nicotinic receptor modulator. Varenicline tartrate (7,8,9,10-tetrahydro-6,10-methano-6H-pyrazino [2,3-h][3]benzazepine (2R,3R)-2,3-dihydroxybutanedionate) reduces severity of nicotine withdrawal symptoms. Its synthesis has been described in WO 01/62736. A preferred embodiment of the invention envisages the combined treatment of subjects for aid in smoking cessation or relapse prevention by vaccination using nicotine-VLP conjugates, preferentially nicotine-Qb conjugates, and administering varenicline, preferably varenicline tartrate. The dose of varenicline tartrate administered is 1 mg twice daily.

(5aS,8S,10aR)-5a,6,9,10-tetrahydro,7H,11H-8,10a-methanopyrido[2',3':5,6]pyrano-[2,3-d]azepine (SSR591813) is a compound that binds with high affinity alpha4beta2 nicotinic acetylcholine receptor (nAChR) subtypes. The synthesis of derivatives is described in U.S. Pat. No. 6,538,003. A preferred embodiment of the invention envisages the combined treatment of subjects for aid in smoking cessation or relapse prevention by vaccination using nicotine-VLP conjugates, preferentially nicotine-Qb conjugates, and administering SSR591813. The dose of SSR591813 is formulated to provide a dose between 1 mg and 500 mg daily.

In a preferred embodiment of the invention the nicotine receptor antagonist mecamylamine hydrochloride or an pharmaceutically acceptable salt thereof is given to subjects for aid in smoking cessation or relapse prevention in combination with vaccination using nicotine-VLP conjugates, preferentially nicotine-Qb conjugates. Mecamylamine hydrochloride has been shown to block many of the physiological, behavioral and reinforcing effects of nicotine. Mecamylamine hydrochloride is formulated to provide a dose of about 1 mg to about 25 mg per day.

Further specific nicotine antagonists include amantadine, pempidine, dihydro-beta-erthyroidine, hexamethonium, erysodine, chlorisondamine, trimethaphan camsylate, tubocurarine chloride, d-tubocurarine, their pharmaceutically acceptable salts or their optical isomers.

Central cannabinoid receptor antagonists are also used to help quitting smoking. Such a cannabinoid antagonist is N-piperidino-5-(4-chloro-phenyl)-1-(2,4-dichlorophenyl)-4-methylpyrazole-3-carboxamide, referred to below as rimonabant. Its synthesis and pharmaceutical compositions containing the same are disclosed in patent applications EP-576'357, EP-656'354, WO 96/02248 and WO 03/040105. The efficacy of rimonabant has been described by Cohen et al. (Behav Pharmacol. 2002, 13, 451-63).

A preferred embodiment of the invention envisages the combined treatment of subjects for aid in smoking cessation or relapse prevention by vaccination using nicotine-VLP conjugates, preferentially nicotine-Qb conjugates, and administering rimonabant. The amount of rimonabant to be administered is formulated so as to provide a dose of 5 to 40 mg per day, preferably 20 mg/day.

In a further embodiment opoid antagonists such as naltrexone can be used in combination with vaccination against nicotine. The use of naltrexone and related compounds in smoking cessation are described in U.S. Pat. No. 6,004,970. Typical doses vary between 12.5 mg and 150 mg.

Anxiolytics have also been administered to treat nicotine withdrawal. Anxiolytics counter the mild anxiety symptoms that occur during smoking cessation treatment, or the treatment of alcoholism and other substance abuse. The anxiolytic isovaleramide has been recommended for the use in smoking cessation (Baladrin et al., WO 94/28888). Further anxiolytics comprise buspirone, hydroxyzine and meprobamate. Buspirone is administered in a dosage range of about 5 mg to 60 mg per day.

Monoamine oxidase inhibitors have been described for treatment of drug withdrawal symptoms (WO 92/21333 and WO 01/12176. Reversible selective inhibitors of monoamine oxidase A, reversible selective inhibitors of monoamine oxidase B or reversible mixed inhibitors of monoamine oxidase A and B can have activity in reducing withdrawal symptoms. Among reversible monoamine oxidase A inhibitors befloxatone, moclobemide, brofaromine, phenoxathine, esuprone, befol, RS 8359 (Sankyo), T794 (Tanabe), KP 9 (Krenitsky USA), E 2011 (Eisei), toloxatone, pirlindole, amiflavine, sercloremine and bazinaprine may be cited. These compounds are known and their preparations are described in the art. Among reversible selective inhibitors of monoamine oxidase B, lazabemide, milacemide, caroxazone, IFO, deprenyl, AGN-1135, MDL72145 and J-508 may be cited. The use of befloxatone or 3-[4-(4,4,4-trifluoro-3R-hydroxybutoxy) phenyl]5(R)-methoxymethyl-2-oxazolidinone for treatment of obesity has been described in WO 01/12176. The use of the deprenyl isomer selegeline has been described in WO92/21333.

A further compound useful in smoking cessation is clonidine (Gourlay et al., Cochrane Library 2003, 2. A preferred embodiment of the invention envisages the combined treatment of subjects for aid in smoking cessation or relapse prevention by vaccination using nicotine-VLP conjugates, preferentially nicotine-Qb conjugates, and administering clonidine, perferably clonidine hydrochloride.

A further compound useful in smoking cessation is sibutramine. Sibutramine has received FDA approval to help people lose weight and it inhibits serotonin and norepinephrine reuptake. Preferably, sibutramine is given in the hydrochloride monohydrate form. Dose administered is 1 to 20 mg daily, preferably 10 or 15 mg daily. A preferred embodiment of the invention envisages the combined treatment of subjects for aid in smoking cessation or relapse prevention by vaccination using nicotine-VLP conjugates, preferentially nicotine-Qb conjugates, and administering sibutramine, preferably sibutramine hydrochloride.

All drug mentioned above may be given orally as a tablet or gel capsule or as a transdermal patches. Formulations of tablets, gel capsules and transdermal patches are described in the art.

Smoking cessation has also been treated with a combination of antidepressants and anxiolytics (Glazer, U.S. Pat. No.

4,788,189 or a combination of nicotine receptor antagonists and an antidepressant or anti-anxiety drug (Cary, WO 99/17803).

Further embodiments of the invention include immune molecules produced by immunization with compositions of the invention. Immune molecules include antibodies and T-cell receptors. Such immune molecules may be useful in a vaccinated individual for binding to target haptens. Immune molecules may also be useful when transferred to another individual not immunized against compositions of the invention, thereby to "passively" transfer immunity. In one embodiment, the immune molecule is an antibody. A monoclonal antibody suitable for binding a toxin, hormone or drug may be transferred into an individual to achieve therapy or prophylaxis. Antibodies against nicotine and other addictive drugs may provide tempory alleviation of addictive behaviour. In other embodiments, antibodies may be administered to an individual at risk of poisoning, or who has been acutely exposed to a toxic agent.

In another embodiment, antibodies are transferred to an individual with immune difficiencies such as observed with cyclosporin or other immunosuppressive drugs, or with acquired immunodeficiency disorders e.g. HIV infection. HIV infection frequently co-occurs with addiction to drugs of abuse, particularly injectable drugs, and addiction may be an underlying cause leading to behaviors that increase the risk of individual acquiring HIV infection (e.g. sharing needles, prostitution). Thus, treatment of addictive behaviour is beneficial to preventing the transmission of HIV into uninfected individuals of the population.

In embodiments utilizing passive immunization, a pool of human donors is immunized with conjugates of the invention using optimal immunization regimens, as determined empirically. At various times, donors are bled by venipuncture and the titers of anti-cocaine antibody are assayed by ELISA. Hyperimmune plasma from multiple donors is pooled and the IgG fraction is isolated by cold alcohol fractionation. The antibody preparation is buffered, stabilized, preserved and standardized as needed for hyperimmune antibody preparations for human use. The level of anti-hapten antibody is standardized by ELISA or other antibody-based assay.

An appropriate dose of purified antibody is administered to patients intramuscularly, subcutaneously or intravenously. In one embodiment, the antibodies are administered with conjugate vaccine, at a different anatomical site in order to elicit active immunity. The appropriate dose is determined by assaying serum levels of recipients in a trail patient population by ELISA or other antibody-based assay at 24 hours or other appropriate time point after injection of the hyperimmune antibody preparation and/or assaying the effectiveness of different doses in inhibiting the effects of the hapten.

The passively transferred immune globulin inhibits the hormone, toxin or drug effects in the patients. The use of human donors, polyclonal antibody, and the large number of donors in the donor pool limits the chance of immune response by the patients to the transferred antibody.

Other embodiments of the invention include processes for the production of the compositions of the invention and methods of medical treatment using said compositions. Diverse approaches for the treatment of addiction are suitable as co-therapies in preventing relapse, including psychiatric, social and legal remedies. Pharmacologic agents useful in co-treatment of addiction include desipramine, buprenorphine, naloxone, haloperidol, chlorproazine, bromocriptine, ibogaine, mazindol, antidepressants and others that will be apparent to the ordinarily skilled artisan.

Kits

The invention also embodies the use of antibodies produced by immunization with compositions of the invention in kits for the detection of haptens in immunoassays (eg ELISA). In a related embodiment, repetitive ordered hapten arrays can be useful for the detection of antibodies against haptens in binding assays.

In some specific embodiments, the compositions of the present invention may be assembled into kits for use in detection in assays or industrial settings, in diagnosis or detection of diseases, conditions or disorders. Such kits according to the present invention may comprise at least one container containing one or more of the above-described conjugates or compositions, including hapten-core particle conjugates and immune molecules directed against such conjugates. Alternative kits of the invention may comprise one or more antibodies of the invention produced by the methods of the invention or by immunization methods familiar to the ordinarily skilled artisan using the conjugates and compositions of the present invention. The kits of the invention may optionally further comprise at least one additional container which may contain, for example, one or more antigens, one or more haptens, one or more core particles, one or more conjugates/compositions of the invention, one or more pharmaceutically acceptable carriers or excipients, one or more buffers, one or more proteins, one or more nucleic acid molecules, and the like The present invention provides kits that can be used in the above methods. In one embodiment, a kit comprises an antibody, produced by a method of the invention, preferably a purified antibody, in one or more containers. In a specific embodiment, the kits of the present invention contain a substantially isolated hapten which is specifically immunoreactive with an antibody included in the kit. Preferably, the kits of the present invention further comprise a control antibody which does not react with the hapten of interest. In another specific embodiment, the kits of the present invention contain a means for detecting the binding of an antibody to a hapten of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against Nicotine. Such a kit includes antibodies of IgA, IgE, IgG and IgG subclasses directed against nicotine and obtained by the immunization of a human with nicotine-Qβ VLP conjugates of the present invention. Such a kit includes a control antibody that does not react with nicotine, and substantially isolated nicotine, cotinine and nornicotine haptens, and purified core particle free of hapten. Further, such a kit includes means for detecting the binding of said antibody to nicotine hapten (e.g., the antibody may be conjugated to a fluorescent compound such as fluorescein or rhodamine which can be detected by flow cytometry, or HRP for use in an ELISA). In one specific embodiments, the kit may include a nicotine attached to a solid support. The invention embodies the use of such a kit, where the titre of different immunoglobulin classes and subclasses are determined in an ELISA. The anti nicotine IgA, IgE and IgG antibodies provided in the kit serve as controls to assess the relative titre of antibodies in the patient serum. After binding of the antibody of the serum and the kit with nicotine hapten, and removing unbound serum components by washing, the antibodies are reacted with antibodies specific for immunoglobulin subtypes that are conjugated to reporter molecules. After a further washing step, to remove unbound labeled antibody, and the amount of reporter associated with the solid phase is determined in the presence of a suitable fluorometric, luminescent or colorimetric substrate (Sigma, St. Louis, Mo.).

Thus, by the use of the above kits, the invention provides a method for monitoring the progress of immunization against nicotine. An immunized person will be monitored during the course of immunization for IgG and IgA antibodies against nicotine, and for the lack IgE antibodies against nicotine that would indicate the development of an allergic reaction If the immune response is primarily against the core particle rather than the hapten, an alternative nicotine conjugate will be utilized, with a different core partile and, in one embodiment, a different hapten.

In one embodiment a kit includes a solid support to which an Nicotine-core particle conjugate is attached. In this embodiment, binding of antibody in the serum of an individual to the antigen presented on the core particle can be detected by binding of a reporter-labeled antibody.

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay systems or kits for carrying out a diagnostic method. The kit generally includes bound recombinant antigen and a reporter-labeled antibody for detecting bound anti-antigen antibody. Other suitable kits of the present invention are understood to those of ordinary skill in the art.

It will be understood by one of ordinary skill in the relevant arts that other suitable modifications and adaptations to the methods and applications described herein are readily apparent and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Coupling Procedure for Nicotine-Qβ Conjugate

A nicotine derivate suitable for coupling to VLPs was synthesized according Langone et al. (1982, supra). Trans-4'-carboxycotinine is available from commercial sources. The methylester of trans-4'-carboxycotinine is produced by reacting trans-4'-carboxycotinine with methanolic sulfuric acid. The solution is neutralized with sodium bicarbonate, extracted with chloroform, concentrated on a rotary evaporator and recrystallized from ether-acetone. Reduction of the methyl ester with lithium aluminium hydride in ether then produces trans-3'-hydroxymethylnicotine. The O'-succinyl-hydroxymethylnicotine is then produced by the addition of succinic anhydride in benzene. The solution is concentrated on a rotary evaporator. Activation of the carboxyl group is subsequently achieved by addition of EDC (1-Ethyl-3-(3-dimethylaminopropyl)-carbodiimide) and N-hydroxysuccinimide (NHS) resulting in the N-hydroxysuccinimide ester of O'-succinyl-hydroxymethylnicotine (in the following abbreviated as "Suc-Nic").

Qβ CP VLPs (SEQ ID NO: 3) were dialysed against Hepes-buffered saline HBS (50 mM Hepes, 150 mM NaCl, pH 8.0). The nicotine derivative Suc-Nic was dissolved in HBS at a concentration of 121 mM. It was added to a Qβ CP VLP solution (0.14 mM) at 1×, 5×, 50×, 100× and 500× molar excess and incubated at room temperature for 2 h on a shaker. The reaction solution was then dialysed against HBS, pH 8.0 (cut off 10000 Da), flash-frozen in liquid nitrogen and stored at −80° C. The nicotine derivative suc-nic reacts with lysines on the surface of Qβ under formation of an amid bond. The resulting covalent conjugate is termed herein "Nic-Qβ".

SDS-PAGE analysis showed with increasing molar excess of Suc-Nic a shift of the Qβ monomer band to higher molecular weights (FIG. 1A). The presence of nicotine in the coupling product was confirmed by a westernblot using an anti-nicotine antiserum. While uncoupled Qβ control and Qβ coupled to nicotine at a 1× and 5× excess did not show an anti-nicotine reactive band, the bands at 50×, 100× and 500× clearly demonstrated covalent coupling of nicotine to Qβ (FIG. 1B). This was confirmed by an ELISA with nicotine-BSA coated on the wells and detection with an anti-nicotine antiserum. A higher absorbance was reached when Qβ coupled with 500 fold excess nicotine was used compared to a vacccine produced with an 50 fold excess.

Example 2

Immunization of Mice with Nic-Qβ and Measurement of Anti-nicotine Antibody Titers A. Immunization of Mice 10 week-old female Balb/c mice were vaccinated twice with 30 μg of the nicotine-Qβ (Nic-Qβ) resulting from the coupling using 500× excess of Suc-Nic. The vaccine was diluted in sterile PBS and given intranasally or injected subcutaneously with or without the addition of Alum (Imject, Pierce). 14 days after the first immunization the mice were boosted (Table I). On day 29 the nicotine-specific antibody titers in serum were determined by ELISA.

TABLE I

Immunization scheme of mice:
B. ELISA.

| No. of animals | vaccine | Day 0 Amount (μg) | Day 14 Amount (μg) | Day 29 Bled |
|---|---|---|---|---|
| 3 | Nic-Qβ s.c. | 30 | 30 | Bled |
| 3 | Nic-Qβ s.c. & Alum | 30 | 30 | Bled |
| 3 | Nic-Qβ intranasal | 30 | 30 | Bled |

Sera were analyzed in a nicotine-specific ELISA: Microtiter plates (Maxisorp, Nunc) were coated overnight with 5 μg/ml nicotine coupled to BSA (NAB03) in coating buffer (pH 9.6). After washing and blocking with 2% BSA in PBS, sera were added at different dilutions in 2% BSA/1% FCS/PBS. After 2 hours incubation at room temperature the plates were washed (0.05% Tween 20/PBS) and HRPO-labeled antibodies specific for mouse antibody subclasses were added. After 1 hour incubation the plates were washed and the color substrate OPD in citric acid buffer was added. After 5 minutes the color reaction was stopped with 5% $H_2SO_4$.

Optical densities at 450 nm were read in an ELISA Reader (Benchmark, Becton Dickinson). For the detection of IgE, sera were pre-incubated in Eppendorf tubes with Protein G beads (Pierce) for 30 min on a shaker before adding to the ELISA plate.

Figure 3A:
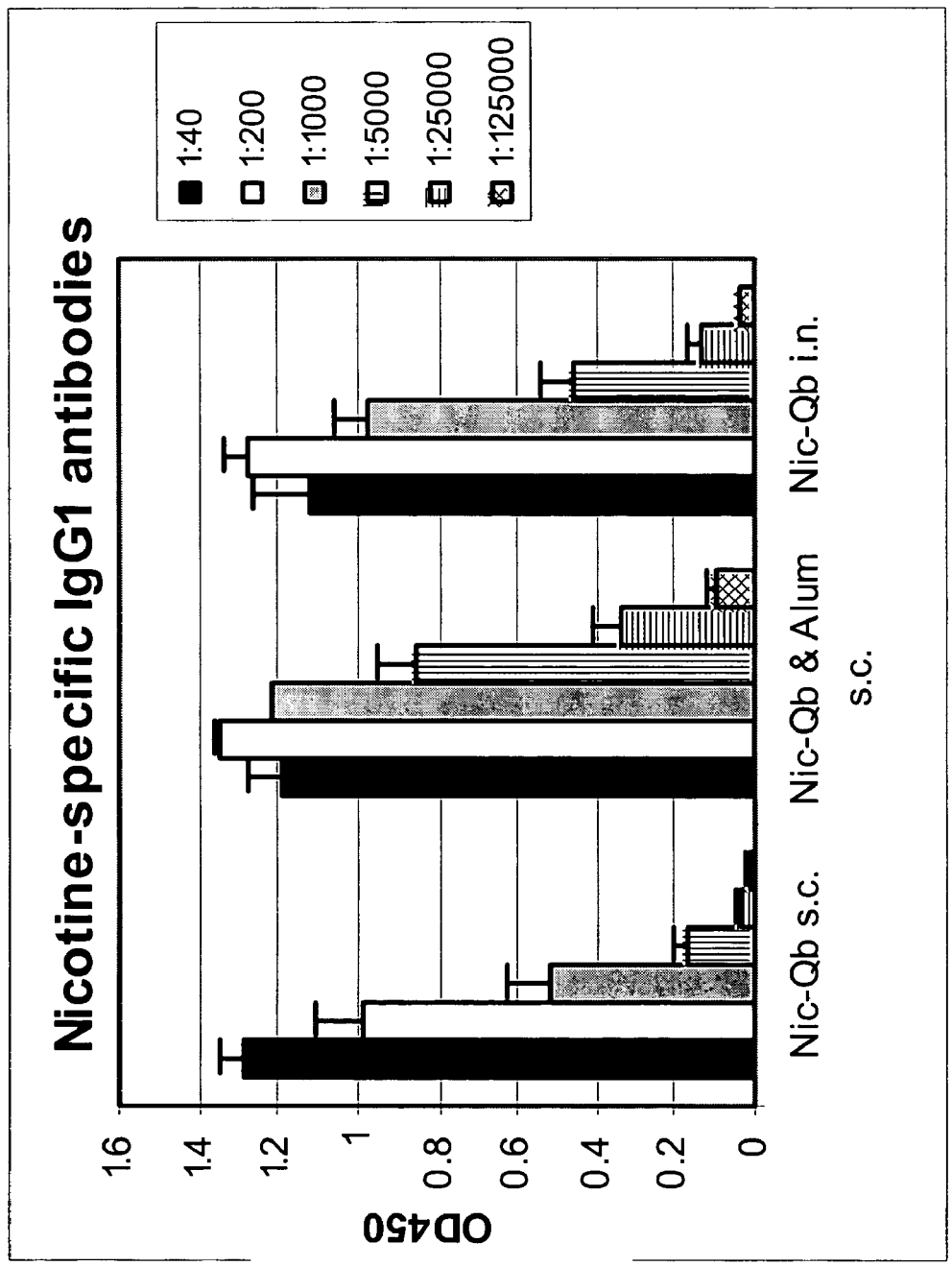
FIGS. 3A, 3B, 3C and 3D depict Nicotine-specific IgG subtypes. Sera from vaccinated mice were tested for reactivity against nicotine coupled to BSA by ELISA and detected with secondary antibodies specific for IgG subtypes IgG1 (A), IgG2a (B), IgG2b (C) and IgG3 (D). Optical densities at 450 nm obtained for each serum dilution are shown. Average of three mice in each group are shown.
Figure 3B:
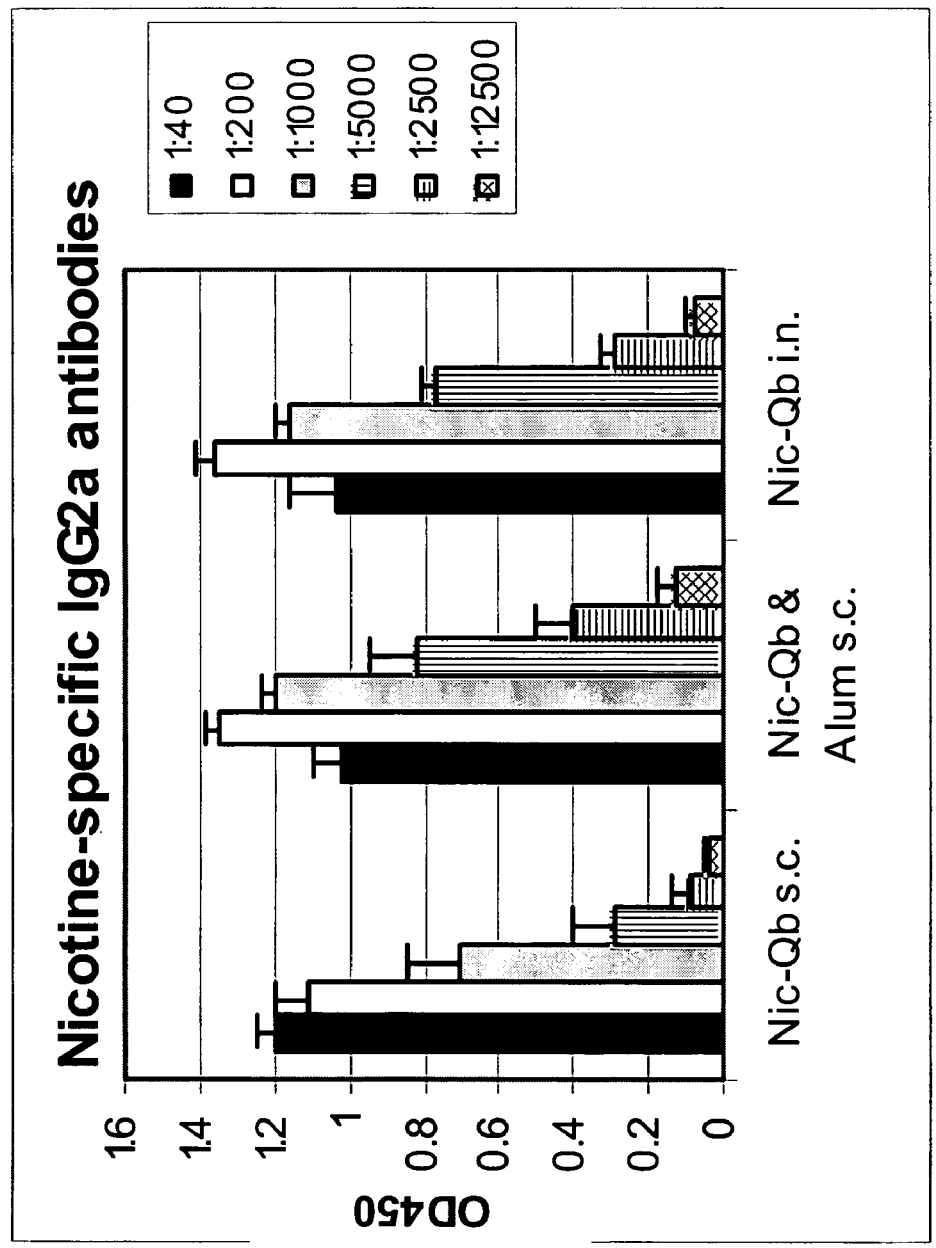
Figure 3C:
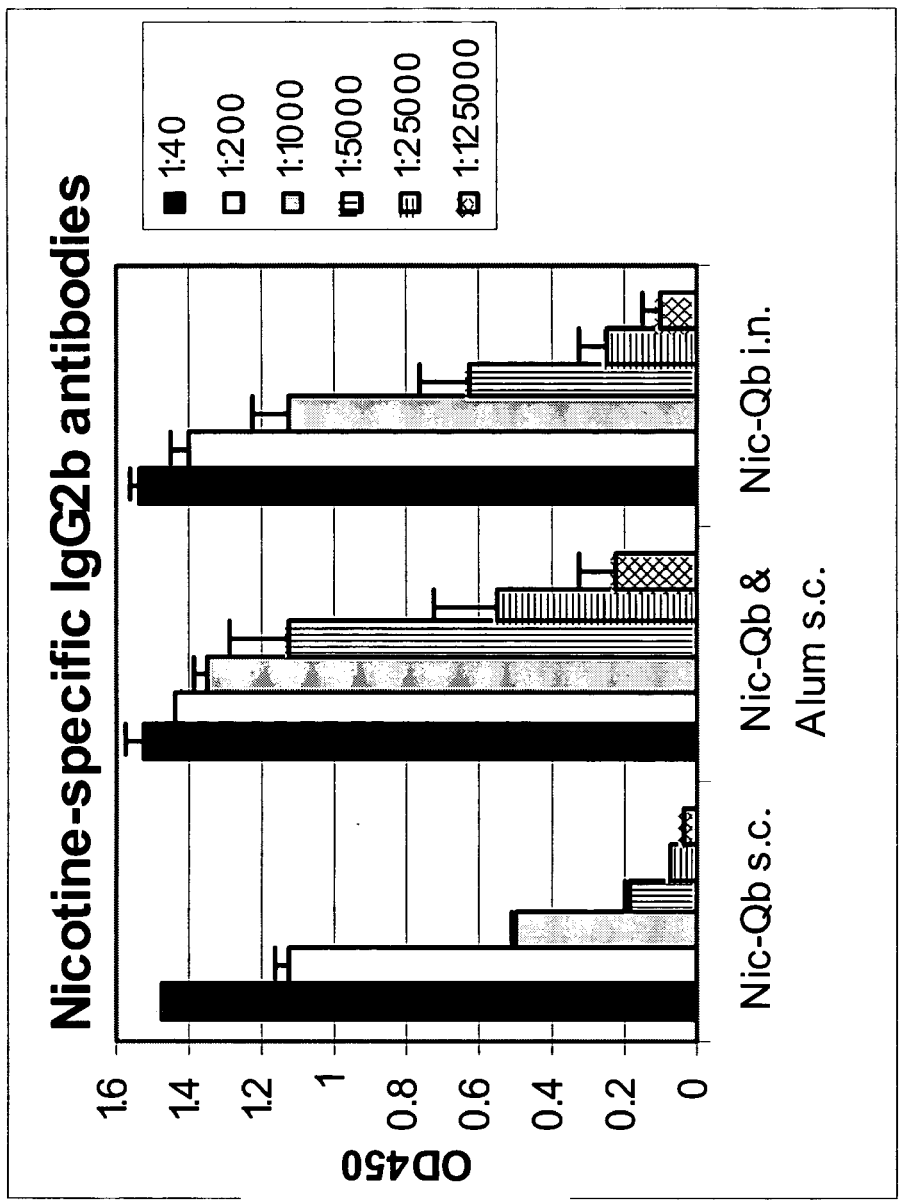
Figure 3D:
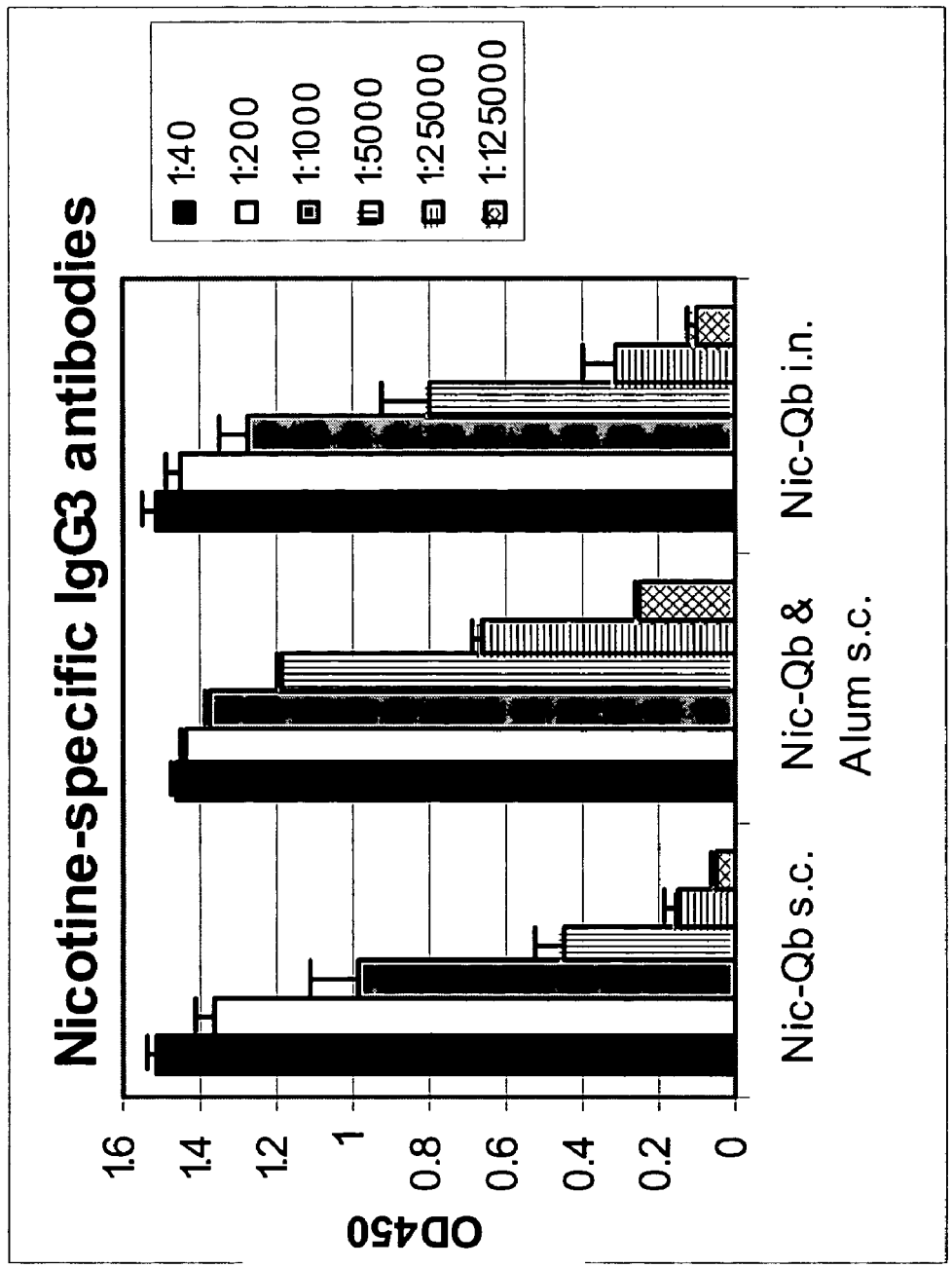

The Nic-Qβ vaccine induced nicotine-specific IgG antibodies (FIG. 3A). The ELISA titers were calculated for the total IgG response (FIG. 3B, Table II). The ELISA titer was defined as the dilution of the serum which gives a half-maximal optical density signal (OD 50%)) in the ELISA. For the subcutaneous route with Alum, the average IgG titers obtained with Nic-Qβ were 13228. For the intranasal route, nicotine-Qβ titers were 38052.

Figure 4:
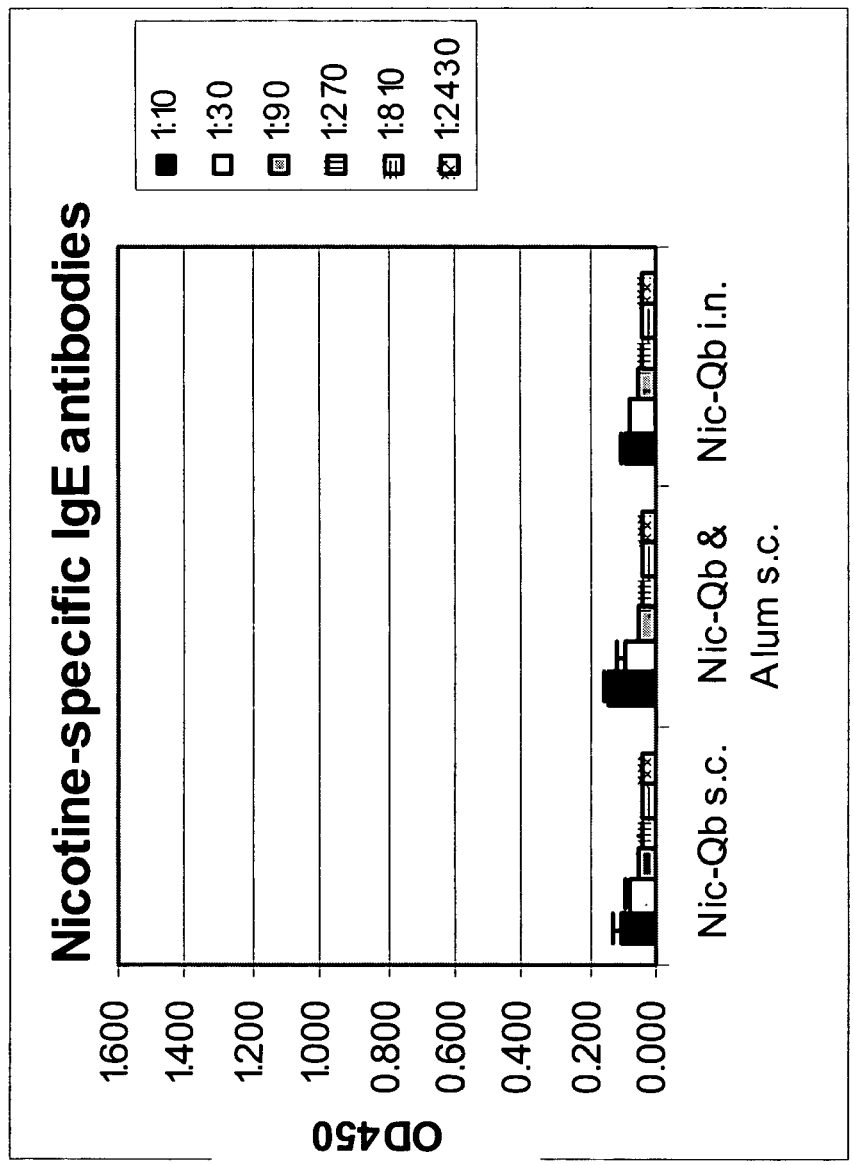
FIG. 4 depicts Nicotine-specific IgE antibodies. Sera from vaccinated mice were tested for reactivity against nicotine coupled to BSA by ELISA and detected with secondary antibodies specific for the IgE subtype. Optical densities at 450 nm obtained for each serum dilution are shown. Average of three mice in each group are shown.
Figure 5:
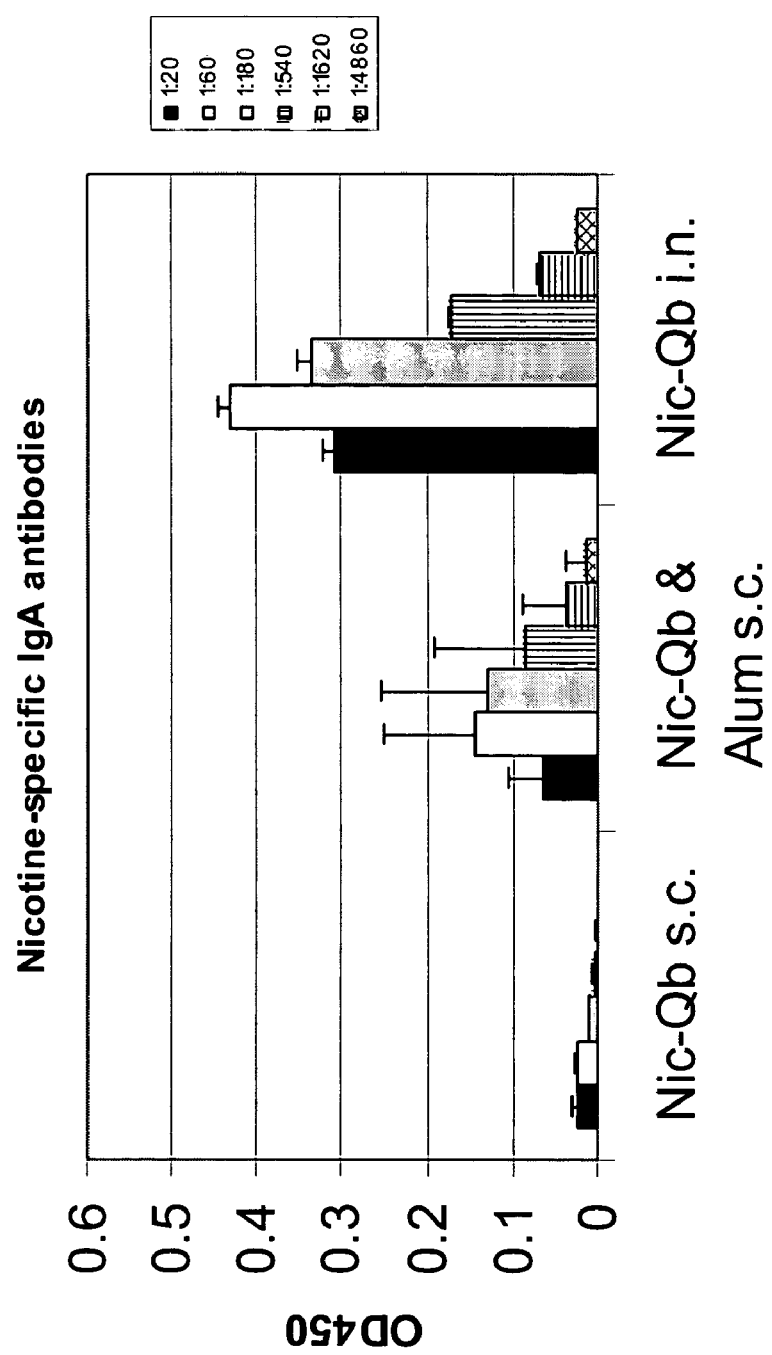
FIG. 5 depicts Nicotine-specific IgA antibodies. Sera from vaccinated mice were tested for reactivity against nicotine coupled to BSA by ELISA and detected with secondary antibodies specific for the IgA subtype. Optical densities at 450 nm obtained for each serum dilution are shown. Average of three mice in each group are shown.
Figure 6A:
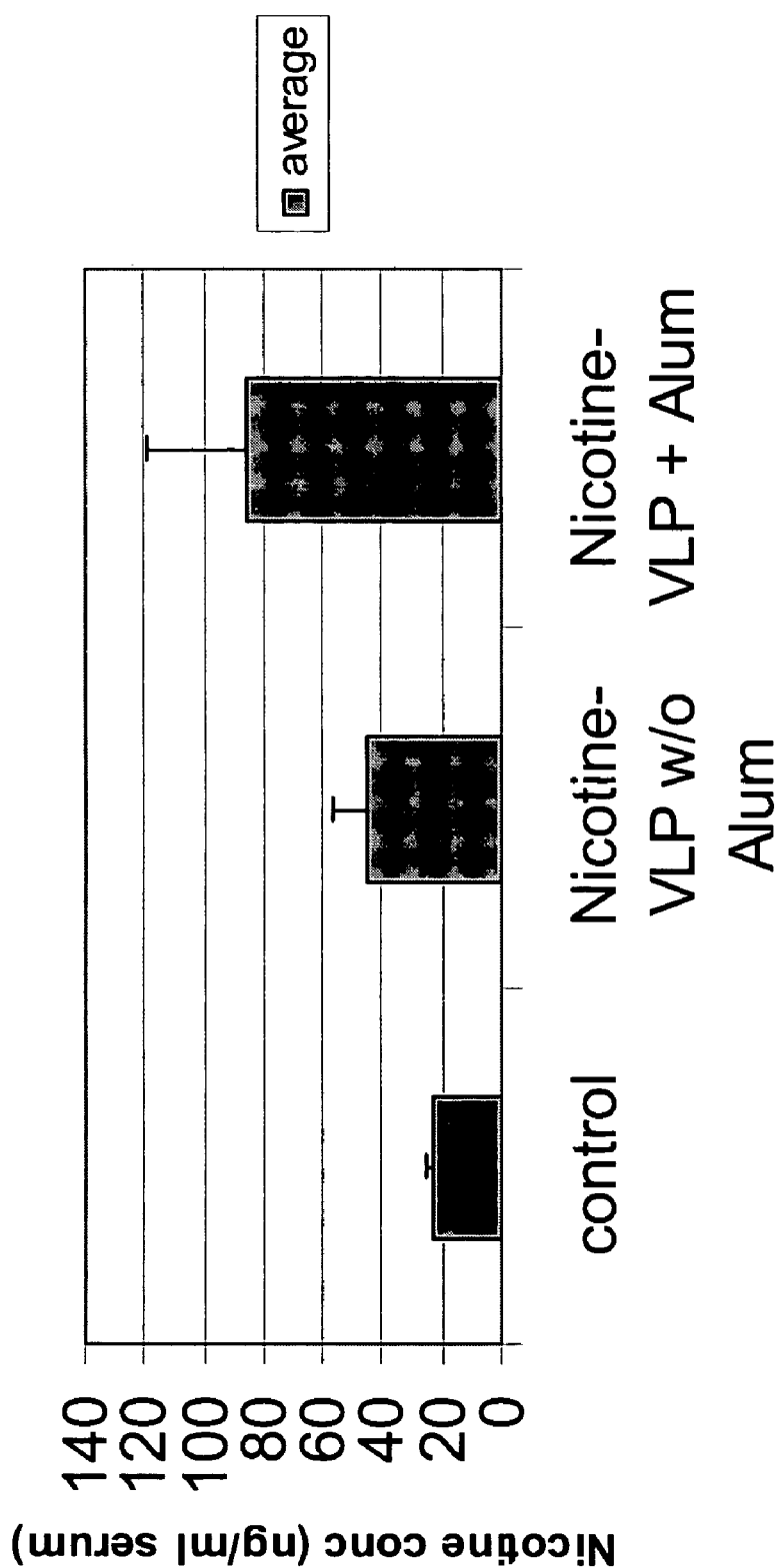
FIGS. 6A and B depict the efficacy of the Nicotine-VLP vaccination. Mice were immunized with Nicotine-VLP and concentrations of nicotine in serum and brain were measured after injection of 3H-nicotine. Averages of four or five mice per group are shown.
Figure 6B:
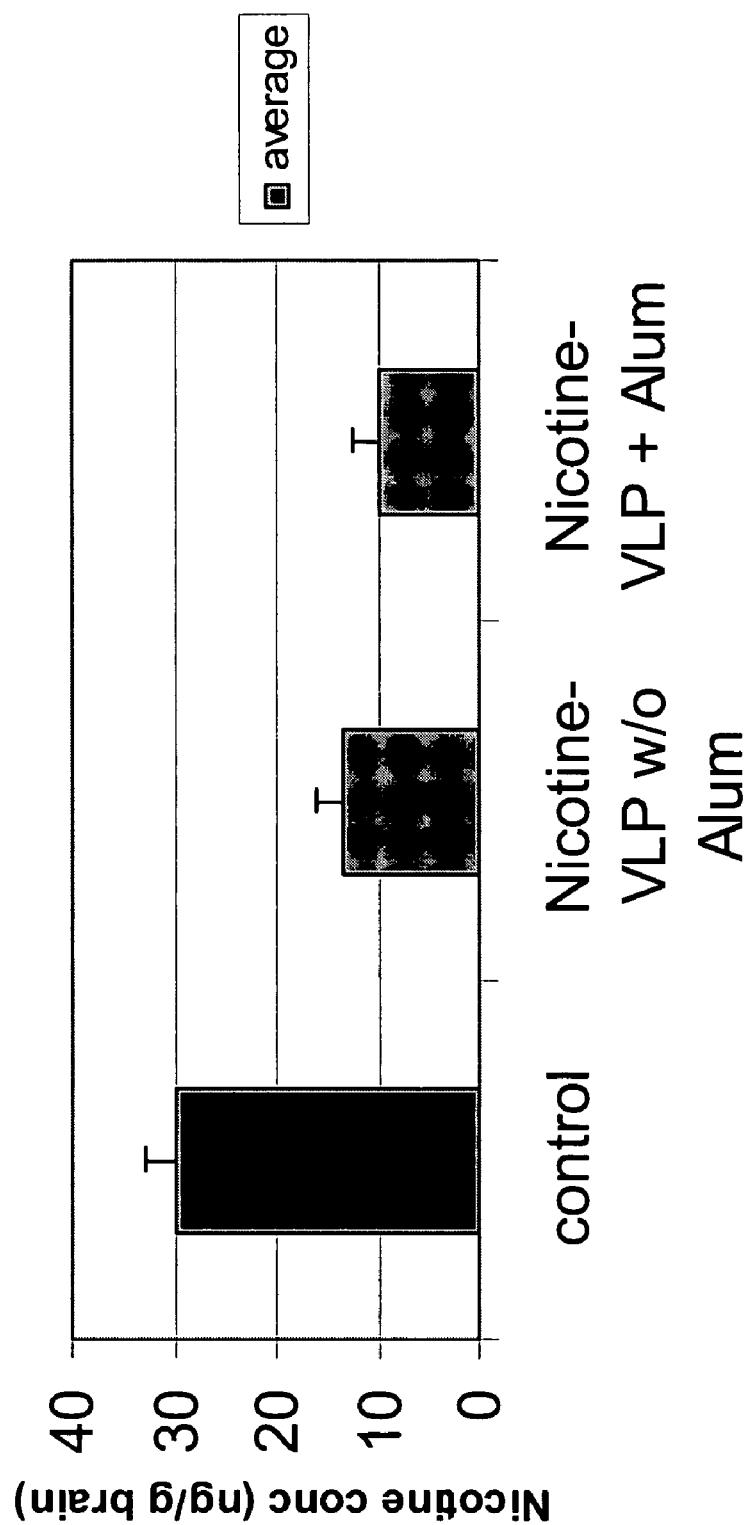

IgG subtypes and IgE were also measured by ELISA and titers determined (FIG. 3, FIG. 4, Table II). No significant IgE response above background (preimmune serum) could be detected for any of the conditions tested. The ratio of IgG2a to IgG1 antibody titers is indicative for a Th1 mediated immune response. A ratio of 2.1 was measured for the mice immunized subcutanously with Nic-Qβ in the absence of Alum, and was even enhanced to 2.6 when applied intranasally. As expected Alum drove the immune response towards a more Th2 type response and resulted in a ratio of 0.4. Notably, the Nic-Qβ vaccines also induced high IgG2b and IgG3 titers. A significant amount of anti-nicotine IgA antibodies could be found in serum (FIG. 5) which are indicative for the presence of IgA in mucosal surfaces.

The high nicotine titres upon intranasal immunization are especially noteworthy.

TABLE II

Nicotine-specific antibody titers in vaccinated mice
Titers were calculated as the dilution of serum that gives half-maximal optical density in the ELISA. Average titers of 3 mice each are given.

| Vaccine | IgG titer | IgG1 titer | IgG2a titer | IgG2b titer | IgG3 titer |
|---|---|---|---|---|---|
| Nic-Qβ s.c. | 13228 | 672 | 1386 | 515 | 2030 |
| Nic-Qβ alum s.c. | 93762 | 9642 | 10016 | 14977 | 19701 |
| Nic-Qβ intranasal | 38052 | 2845 | 7493 | 3617 | 6107 |

Example 3

Evaluation of Nicotine Distribution in Plasma and Brain in Rats

Groups of rats are immunized with the nicotine-VLP vaccine, boosted at day 21. One group receives a second boost at day 35. Seven to 10 days after the last boost rats are anestethized and catheters are placed in the femoral artery and vein for sampling and the jugular vein of the other leg for nicotine adminstration. Nicotine 0.03 mg/kg containing 3 microCi 3H-(−)-nicotine is infused in 1 ml/kg 0.9% saline via the jugular vein over 10 s. The radiolabel is added to permit estimation of nicotine concentrations from very small volumes of blood. This the possible because metabolism of nicotine to cotinine over the first 90 s after nicotine administration in rats negligible. Blood (0.3 ml) was removed from both the femoral artery and vein catheers every 15 s up to 90 s, centrifuged immediately and serum separated for assay. Rats are killed at 3 min by decapitation, the brain is removed quickly, rinsed with water and stored at −20° C. until assayed. For measurement of 3H-nicotine concentration in serum, 100 ul serum is mixed with liquid scintillation fluid. Brain samples were digested in 5 vol NaOH prior to extraction and analysed after addition of scintillation fluid.

Nicotine-specific antibodies induced by the vaccination are capable of binding 3H-nicotine in serum and inhibit or lower its diffusion into the brain. Accordingly, a decreased concentration of brain nicotine and an increased concentration of plasma nicotine are measured.

Example 4

Chemical Coupling of Nicotine Hapten to HbcAg-Lys

O-succinyl-hydroxymethylnicotine is prepared as described in Example 1, and incubated with EDC and NHS to yield the activated N-hydroxysuccinamide ester (Suc-Nic). Purified HbcAg-Lys VLP is prepared as described in copending U.S. patent application Ser. No. 10/050,902. Suc-Nic solution in HBS is added at 1×, 5×, 50×, 100× and 500× molar excess to a 95% pure solution of HBcAg-Lys particles (2 mg/ml) and incubated for 2 h. at room temperature. After completion of the reaction, the mixture is dialyzed overnight against HBS, pH 8.0, flash frozen in liquid nitrogen and stored at −80° C. Reaction is monitored by SDS-PAGE analysis and western blot with antinicotine antiserum. Nicotine decorated particles are injected into rodents to induce immune responses against nicotine.

Example 5

Chemical Coupling of Nicotine Hapten to Type-1 Pili of *Escherichia coli*

Type I pili are prepared from *E. coli* strain W3110 transformed with the vector pFIMAICDFGK, and purified by ultracentrifugation, as described in commonly owned, copending U.S. patent application Ser. No. 10/050,902, filed Jan. 18, 2002, the disclosure of which is incorporated herein by reference in its entirety. Activated hapten Suc-Nic in HBS are added at 1×, 5×, 50×, 100× and 500× molar excess to a 95% pure solution of type I pili particles (2 mg/ml) and incubated for 2 h. at room temperature. After completion of the reaction, the mixture is dialyzed against HBS, pH 8.0, flash frozen in liquid nitrogen and stored at −80° C. Reaction is monitored by SDS-PAGE analysis and western blot with antinicotine antiserum. Nicotine decorated particles are injected into rodents to induce immune responses against nicotine.

Example 6

Synthesis of Multi-hapten Vaccine Suitable for Treatment of Nicotine Addiction

A vaccine against nicotine addiction designed to target multiple epitopes of nicotine and also the pharmaceutically active metabolites cotinine and nornicotine is prepared. Individual 120 mM solutions in HBS of 6-(carboxymethylureido)-(±)-nicotine (CMUNic), trans-3'-aminomethylnicotine succinate, O-succinyl-3'-hydroxymethyl-nicotine, Trans-4'-carboxycotinine, N-[1-oxo-6-[(2S)-2-(3-pyridyl)-1-pyrrolidinyl]hexyl]-β-alanine, 4-oxo-4-[[6-[(5S)-2-oxo-5-(3-pyridinyl)-1-pyrrolidinyl]]hexyl]amino]-butanoic acid, (2S)-2-(3-pyridinyl)-1-pyrrolidinebutanoic acid phenylmethyl ester, (2R)-2-(3-pyridinyl)-1-pyrrolidinebutanoic acid phenylmethyl ester, Cotinine 4'-carboxylic acid, N-succinyl-6-amino-(.+−.)-nicotine; 6-(.sigma.-aminocapramido)-(.+−.)-nicotine- and 6-(.sigma.-aminocapramido)-(.+−.)-nicotine- conjugates; succinylated 3',4', and 5' aminomethylnicotine, 5 and 6 aminonicotine and 3',4', and 5' acetyl derivatives of acetyl nicotine. The solutions are mixed with EDC and NHS to form activated forms which are added, in separate reactions, at 10-100 molar excess to Qβ VLP as described elsewhere.

Individual solutions of S-1-(b-aminoethyl)nicotinium chloride dihydrochloride and S-1-(b-aminoethyl)cotinium chloride hydrochloride solutions are coupled to Qβ VLP with 1-cyclohexyl-3-(2-morpholinoethyl)-carbodiimide metho-p-toluenesulfonate.

From this selection of conjugates, eight of the nicotine hapten Qβ VLP conjugates, a cotinine Qβ VLP conjugate and a nornicotine conjugate Qβ VLP are then admixed to form a vaccine composition, which is used to vaccinate individuals. After 2 doses, individuals are then boosted 3 times with parallel haptens coupled to HBc-Lys VLP conjugates.

Example 7

Synthesis of Cocaine VLP-Hapten Conjugate

A solution of norcocaine hydrochloride (1 g, 3.07 mmol), triethylamine (0.86 ml, 6.14 mmol) in methylene chloride (20 ml) is treated with succinic anhydride (614 mg, 6.14 mmol) and the mixture heated at 45.degree. C. overnight, as described in U.S. Pat. No. 5,876,727. The solvents are removed under reduced pressure and the residue purified using silica gel flash chromatography (2:1 chloroform:methanol as the eluent). This gives succinylated norcocaine (1.0 g, 84%) as a thick syrup (3.beta.-(Benzoyloxy)-8-succinoyl-8-azabicyclo[3.2.1]octane-2.beta.-carboxylic acid methyl ester). To a solution of the acid (14 mg, 0.036 mmol) in distilled water (1 ml) at 0.degree. C., EDC (10.4 mg, 0.055 mmol) was added. After 5 minutes a solution of Qβ VLP in PBS (1 ml) is added dropwise and the mixture is allowed to warm to ambient temperature overnight. The conjugate is purified by dialysis against PBS and the degree of conjugation analyzed by mass spectral analysis. The resultant conjugate is used to immunize individuals.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

Example 8

Evaluation of Nicotine Distribution in Plasma and Brain of Mice

Groups of 4 to 5 mice were immunized with 60 ug of the nicotine-VLP vaccine produced as described in EXAMPLE 1 and were boosted at day 35 and day 63 with the same amount of vaccine. Fourteen days after the last boost mice were injected i.v. at the base of the tail with a solution containing 750 ng (−)-nicotine hydrogen tartrate with 5 microCi 3H-(−)-nicotine. The amount of nicotine corresponds to 0.03 mg/kg which is equivalent to the nicotine uptake of 2 cigarettes by a smoker. The radiolabel was added to permit estimation of nicotine concentrations from very small volumes of blood. After five minutes mice were sacrificed by $CO_2$. Blood was removed by punctation of the heart and serum was prepared. Brains was immediately dissected, cleaned from adhering blood and their weights measured. For measurement of 3H-nicotine concentration in serum, 50 ul serum is mixed with liquid scintillation fluid. Brain samples were completely dissolved in 2 ml Tissue Solubilizer (Serva) and analysed after addition of scintillation fluid. From the radioactivities nicotine concentrations in serum and brain were calculated (FIG. 7).

Nicotine-specific antibodies induced by the vaccination were capable of binding 3H-nicotine in serum and inhibit or lower its diffusion into the brain. Accordingly, a decreased concentration of brain nicotine and an increased concentration of plasma nicotine were measured. The Nicotine-VLP vaccine was able to inhibit the nicotine uptake in brain by 56% in the absence of Alum and by 68% in the presence of Alum (FIG. 7).

Further immunization schedules, such as immunization at day 0 and and boosting at day 14 also yielded in antibodies levels that were able to significantly reduce nicotine uptake into brain. In general, high anti-nicotine antibody titers correlated with a higher efficacy of the vaccination.

Example 9

Cloning of the AP205 Coat Protein Gene

The cDNA of AP205 coat protein (CP) (SEQ ID NO: 90) was assembled from two cDNA fragments generated from phage AP205 RNA by using a reverse transcription-PCR technique and cloning in the commercial plasmid pCR 4-TOPO for sequencing. Reverse transcription techniques are well known to those of ordinary skill in the relevant art. The first fragment, contained in plasmid p205-246, contained 269 nucleotides upstream of the CP sequence and 74 nucleotides coding for the first 24 N-terminal amino acids of the CP. The second fragment, contained in plasmid p205-262, contained 364 nucleotides coding for amino acids 12-131 of CP and an additional 162 nucleotides downstream of the CP sequence. Both p205-246 and p205-262 were a generous gift from J. Klovins.

The plasmid 283.-58 was designed by two-step PCR, in order to fuse both CP fragments from plasmids p205-246 and p205-262 in one full-length CP sequence.

An upstream primer p1.44 containing the NcoI site for cloning into plasmid pQb185, or p1.45 containing the XbaI site for cloning into plasmid pQb10, and a downstream primer p1.46 containing the HindIII restriction site were used (recognition sequence of the restriction enzyme underlined):

```
p1.44  5'-NNCC ATG GCA AAT AAG CCA    (SEQ ID NO: 5)
       ATG CAA CCG-3p' p1.45  5'-NNTCTAGAATTTTCTGCGCAC      (SEQ ID NO: 20)
       CCATCCCGG-3' p1.46  5'-NNAAGC TTA AGC AGT AGT ATC  (SEQ ID NO: 21)
       AGA CGA TAC G-3'
```

Two additional primers, p1.47, annealing at the 5' end of the fragment contained in p205-262, and p1.48, annealing at the 3' end of the fragment contained in plasmid p205-246 were used to amplify the fragments in the first PCR. Primers p1.47 and p1.48 are complementary to each other.

```
p1.47: 5'-GAGTGATCCAACTCGTTTATCAAC  (SEQ ID NO: 22)
       TACATTTTCAGCAAGTCTG-3' p1.48: 5'-CAGACTTGCTGAAAATGTAGTTGA  (SEQ ID NO: 23)
       TAAACGAGTTGGATCACTC-3'
```

In the first two PCR reactions, two fragments were generated. The first fragment was generated with primers p1.45 and p1.48 and template p205-246. The second fragment was generated with primers p1.47 and p1.46, and template p205-262. Both fragments were used as templates for the second PCR reaction, a splice-overlap extension, with the primer combination p1.45 and p1.46 or p1.44 and p1.46. The product of the two second-step PCR reactions were digested with XbaI or NcoI respectively, and HindIII, and cloned with the same restriction sites into pQb10 or pQb185 respectively, two pGEM-derived expression vectors under the control of *E. coli* tryptophan operon promoter.

Two plasmids were obtained, pAP283-58 (SEQ ID NO: 15), containing the gene coding for wt AP205 CP (SEQ ID NO: 14) in pQb10, and pAP281-32 (SEQ ID NO: 19) with mutation Pro5→Thr (SEQ ID NO: 18), in pQb185. The coat protein sequences were verified by DNA sequencing. PAP283-58 contains 49 nucleotides upstream of the ATG codon of the CP, downstream of the XbaI site, and contains the putative original ribosomal binding site of the coat protein mRNA.

Example 10

Expression and Purification of Recombinant AP205 VLP

A. Expression of Recombinant AP205 VLP

*E.coli* JM109 was transformed with plasmid pAP283-58. 5 ml of LB liquid medium with 20 µg/ml ampicillin were inoculated with a single colony, and incubated at 37° C. for 16-24 h without shaking.

The prepared inoculum was diluted 1:100 in 100-300 ml of LB medium, containing 20 µg/ml ampicillin and incubated at 37° C. overnight without shaking. The resulting second inoculum was diluted 1:50 in 2TY medium, containing 0.2% glucose and phosphate for buffering, and incubated at 37° C. overnight on a shaker. Cells were harvested by centrifugation and frozen at −80° C.

B. Purification of Recombinant AP205 VLP

Solutions and buffers:

1. Lysis buffer
   50 mM Tris-HCl pH 8.0 with 5 mM EDTA, 0.1% tritonX100 and PMSF at 5 micrograms per ml.

2. SAS
   Saturated ammonium sulphate in water

3. Buffer NET.
   20 mM Tris-HCl, pH 7.8 with 5 mM EDTA and 150 mM NaCl.

4. PEG
   40% (w/v) polyethylenglycol 6000 in NET

Lysis:

Frozen cells were resuspended in lysis buffer at 2 ml/g cells. The mixture was sonicated with 22 kH five times for 15 seconds, with intervals of 1 min to cool the solution on ice. The lysate was then centrifuged for 20 minutes at 12 000 rpm, using a F34-6-38 rotor (Ependorf). The centrifugation steps described below were all performed using the same rotor, except otherwise stated. The supernatant was stored at 4° C., while cell debris were washed twice with lysis buffer. After centrifugation, the supernatants of the lysate and wash fractions were pooled.

Ammonium-sulphate precipitation can be further used to purify AP205 VLP. In a first step, a concentration of ammonium-sulphate at which AP205 VLP does not precipitate is chosen. The resulting pellet is discarded. In the next step, an ammonium sulphate concentration at which AP205 VLP quantitatively precipitates is selected, and AP205 VLP is isolated from the pellet of this precipitation step by centrifugation (14 000 rpm, for 20 min). The obtained pellet is solubilised in NET buffer.

Chromatography:

The capsid protein from the pooled supernatants was loaded on a Sepharose 4B column (2.8×70 cm), and eluted with NET buffer, at 4 ml/hour/fraction. Fractions 28-40 were collected, and precipitated with ammonium sulphate at 60% saturation. The fractions were analyzed by SDS-PAGE and Western Blot with an antiserum specific for AP205 prior to precipitation. The pellet isolated by centrifugation was resolubilized in NET buffer, and loaded on a Sepharose 2B column (2.3×65 cm), eluted at 3 ml/h/fraction. Fractions were analysed by SDS-PAGE, and fractions 44-50 were collected, pooled and precipitated with ammonium sulphate at 60% saturation. The pellet isolated by centrifugation was resolubilized in NET buffer, and purified on a Sepharose 6B column (2.5×47 cm), eluted at 3 ml/hour/fraction. The fractions were analysed by SDS-PAGE. Fractions 23-27 were collected, the salt concentration adjusted to 0.5 M, and precipitated with PEG 6000, added from a 40% stock in water and to a final concentration of 13.3%. The pellet isolated by centrifugation was resolubilized in NET buffer, and loaded on the same Sepharose 2B column as above, eluted in the same manner. Fractions 43-53 were collected, and precipitated with ammonium sulphate at a saturation of 60%. The pellet isolated by centrifugation was resolubilized in water, and the obtained protein solution was extensively dialyzed against water. About 10 mg of purified protein per gram of cells could be isolated. Examination of the virus-like particles in Electron microscopy showed that they were identical to the phage particles.

What is claimed is:

1. A method for treating nicotine addiction in animal, said method comprising administering to an animal a composition comprising an immunologically effective amount of a nicotine hapten-carrier conjugate, said conjugate comprising:
   (a) a virus-like particle of an RNA phage carrier with at least one first attachment site, and
   (b) at least one nicotine hapten with at least one second attachment site;
      wherein said second attachment site is associated through at least one covalent bond to said first attachment site so as to form an ordered and repetitive nicotine hapten-carrier conjugate;
   wherein an immune response to said nicotine hapten is obtained in said animal.

2. The method of claim 1, where said composition is administered to said animal intranasally, orally, subcutaneously, transdermally, intramuscularly or intravenously.

3. The method of claim 1, wherein the animal is a human.

4. The method of claim 1, wherein said RNA phage is selected from the group consisting of:
   (a) bacteriophage Qβ;
   (b) bacteriophage R17;
   (c) bacteriophage fr;
   (d) bacteriophage GA;
   (e) bacteriophage SP;
   (f) bacteriophage MS2;
   (g) bacteriophage M11;
   (h) bacteriophage MX1;
   (i) bacteriophage NL95;
   (j) bacteriophage f2;
   (k) bacteriophage AP205; and
   (l) bacteriophage PP7.

5. The method of claim 1, wherein said virus-like particle of an RNA phage comprises recombinant proteins of RNA phage Qβ.

6. The method of claim 1, wherein said virus-like particle of an RNA phage comprises recombinant proteins, or fragments thereof, of an RNA phage.

7. The method of claim 1, wherein said virus-like particle of an RNA phage comprises one or more proteins having an amino acid sequence selected from the group consisting of:
   (a) SEQ ID NO:3;
   (b) a mixture of SEQ ID NO:3 and SEQ ID NO:4;
   (c) SEQ ID NO:24;
   (d) SEQ ID NO:25;
   (e) SEQ ID NO:26;
   (f) SEQ ID NO:27;
   (g) a mixture of SEQ ID NO:27 and SEQ ID NO:28;
   (h) SEQ ID NO:29;

(i) SEQ ID NO:30;
(j) SEQ ID NO:31;
(k) SEQ ID NO:32;
(l) SEQ ID NO:33;
(m) SEQ ID NO:13; and
(n) SEQ ID NO:14.

8. The method of claim 1, wherein said virus-like particle of an RNA phage comprises SEQ ID NO:3.

9. The method of claim 1, wherein said virus-like particle of an RNA phage comprises a mixture of SEQ ID NO:3 and SEQ ID NO:4.

10. The method of claim 1, wherein said virus-like particle of an RNA phage consists essentially of SEQ ID NO:3.

11. The method of claim 1, wherein said virus-like particle of an RNA phage consists essentially of a mixture of SEQ ID NO:3 and SEQ ID NO:4.

12. The method of claim 1, wherein said virus-like particle of an RNA phage comprises one or more coat proteins of said RNA phage modified by deletion or substitution to remove at least one naturally occurring lysine residue, or that have been modified by insertion or substitution to add at least one lysine residue.

13. The method of claim 12, wherein said RNA phage is Qβ.

14. The method of claim 13, wherein said virus-like particle comprises one or more proteins having an amino acid sequence selected from the group consisting of:
(a) SEQ ID NO:6;
(b) SEQ ID NO:7;
(c) SEQ ID NO:8;
(d) SEQ ID NO:9; and
(e) SEQ ID NO: 10.

15. The method of claim 1, wherein said first attachment site comprises:
(a) an amino group;
(b) a carboxyl group;
(c) a sulfhydryl group;
(d) a hydroxy group;
(e) a guanidinyl group; or
(f) a histidinyl group.

16. The method of claim 1, wherein said first attachment site comprises an amino group.

17. The method of claim 1, wherein said first attachment site is selected from the group consisting of a lysine residue, an arginine residue, a cysteine residue, an aspartate residue, a glutamate residue, a serine residue, a threonine residue, a histidine residue and a tyrosine residue.

18. The method of claim 1, wherein said first attachment site is a lysine residue.

19. The method of claim 1, wherein said conjugate is formed from starting materials selected from the group consisting of
(a) 6-(carboxymethylureido)-(±)-nicotine (CMUNic);
(b) trans-3'-aminomethylnicotine succinate;
(c) O-succinyl-3'-hydroxymethyl-nicotine;
(d) Trans-4'-carboxycotinine;
(e) N-[1-oxo-6-[(2S)-2-(3-pyridyl)-1-pyrrolidinyl]hexyl]-β-alanine;
(f) N-succinyl-6-amino-(±)-nicotine;
(g) 6-(sigma-aminocapramido)-(±)-nicotine;
(h) 3'-aminomethylnicotine;
(i) 4'-aminomethylnicotine;
(j) 5'-aminomethylnicotine;
(k) 5-aminonicotine;
(l) 6-aminonicotine; and
(m) S-1-(b-aminoethyl)nicotinium chloride.

20. The method of claim 1, wherein said conjugate is formed from the starting material O-succinyl-3'-hydroxymethyl-nicotine.

21. The method of claim 1, wherein said nicotine hapten comprises the starting material O-succinyl-3'-hydroxymethyl-nicotine.

22. The method of claim 1, wherein said conjugate comprises O-succinyl-3'-hydroxymethyl-nicotine conjugated to a Qβ virus-like particle.

23. The method of claim 1, wherein said hapten is formed from the staffing material O-succinyl-3'-hydroxymethyl-nicotine.

24. The method of claim 1, wherein the second attachment site contains an active group selected from the group consisting of (a) Amine; (b) Amide; (c) Carboxyl; (d) Sulfhydryl; (e) Hydroxyl; (f) Aldehyde; (g) Diazonium; (h) Acylhalogen; (i) Hydrazine; (j) Vinyl; (k) Maleimide; (l) Succinimide; and (m) Hydrazide.

25. The method of claim 24, wherein said second attachment site is formed by reaction of the O-succinyl moiety of said O-succinyl-3'-hydroxymethylnicotine with said first attachment site.

26. The method of claim 1, wherein said second attachment site contains an amide.

27. The method of claim 1, wherein said second attachment site is formed by reaction of the O-succinyl moiety of the O-succinyl-3'-hydroxymethylnicotine and wherein said first attachment site is a lysine residue.

28. The method of claim 1, wherein said first attachment site is a lysine residue, and wherein said nicotine hapten comprises the starting material O-succinyl-3'-hydroxymethyl-nicotine and wherein said second attachment site is formed by reaction of the O-succinyl moiety of the O-succinyl-3'-hydroxymethylnicotine.

29. The method of claim 28, wherein said virus-like particle of an RNA phage comprises SEQ ID NO:3.

30. The method of claim 28, wherein said virus-like particle of an RNA phage consists essentially of SEQ ID NO:3.

31. The method of claim 3, where said composition is administered to said human subcutaneously.

32. The method of claim 3, where said composition is administered to said human intramuscularly.

33. The method of claim 1, where said immunologically effective amount of said nicotine hapten-carrier conjugate is 100 μg.

34. The method of claim 1, wherein said composition further comprises a pharmaceutically acceptable carrier or excipient.

35. The method of claim 34, wherein said composition further comprises an adjuvant.

36. The method of claim 35, wherein said adjuvant is an aluminium salt.

37. The method of claim 35, wherein said adjuvant is MF59.

38. The method of claim 34, wherein said composition is devoid of an adjuvant.

39. The method of claim 34, where said composition is administered to said animal intranasally, orally, subcutaneously, transdermally, intramuscularly or intravenously.

40. The method of claim 34, wherein the animal is a human.

41. The method of claim 40, where said composition is administered to said human subcutaneously.

42. The method of claim 40, where said composition is administered to said human intramuscularly.

43. The method of claim 34, wherein said method comprises two or more immunizations of said individual with said composition.

44. The method of claim 43, wherein the immunizations are by the same route.

45. The method of claim 43, wherein the immunizations are by different routes.

* * * * *

SEQUENCE LISTING

<160> NUMBER OF SEQ ID NOS: 33

<210> SEQ ID NO 1
<211> LENGTH: 185
<212> TYPE: PRT
<213> ORGANISM: Hepatitis B virus

<400> SEQUENCE: 1

```
Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185
```

<210> SEQ ID NO 2
<211> LENGTH: 182
<212> TYPE: PRT
<213> ORGANISM: Escherichia coli

<400> SEQUENCE: 2

```
Met Lys Ile Lys Thr Leu Ala Ile Val Val Leu Ser Ala Leu Ser Leu
 1               5                  10                  15

Ser Ser Thr Thr Ala Leu Ala Ala Thr Thr Val Asn Gly Gly Thr
            20                  25                  30

Val His Phe Lys Gly Glu Val Val Asn Ala Ala Cys Ala Val Asp Ala
        35                  40                  45

Gly Ser Val Asp Gln Thr Val Gln Leu Gly Gln Val Arg Thr Ala Ser
    50                  55                  60

Leu Ala Gln Glu Gly Ala Thr Ser Ser Ala Val Gly Phe Asn Ile Gln
65                  70                  75                  80

Leu Asn Asp Cys Asp Thr Asn Val Ala Ser Lys Ala Ala Val Ala Phe
                85                  90                  95

Leu Gly Thr Ala Ile Asp Ala Gly His Thr Asn Val Leu Ala Leu Gln
            100                 105                 110

Ser Ser Ala Ala Gly Ser Ala Thr Asn Val Gly Val Gln Ile Leu Asp
        115                 120                 125
```

```
Arg Thr Gly Ala Ala Leu Thr Leu Asp Gly Ala Thr Phe Ser Ser Glu
    130                 135                 140

Thr Thr Leu Asn Asn Gly Thr Asn Thr Ile Pro Phe Gln Ala Arg Tyr
145                 150                 155                 160

Phe Ala Thr Gly Ala Ala Thr Pro Gly Ala Ala Asn Ala Asp Ala Thr
                165                 170                 175

Phe Lys Val Gln Tyr Gln
                180

<210> SEQ ID NO 3
<211> LENGTH: 132
<212> TYPE: PRT
<213> ORGANISM: Bacteriophage Qbeta

<400> SEQUENCE: 3

Ala Lys Leu Glu Thr Val Thr Leu Gly Asn Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Ala Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 4
<211> LENGTH: 329
<212> TYPE: PRT
<213> ORGANISM: Bacteriophage Qbeta

<400> SEQUENCE: 4

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125
```

-continued

```
Leu Asn Pro Ala Tyr Trp Thr Leu Leu Ile Ala Gly Gly Ser Gly
        130                 135                 140

Ser Lys Pro Asp Pro Val Ile Pro Asp Pro Ile Asp Pro Pro
145                 150                 155                 160

Gly Thr Gly Lys Tyr Thr Cys Pro Phe Ala Ile Trp Ser Leu Glu Glu
                165                 170                 175

Val Tyr Glu Pro Pro Thr Lys Asn Arg Pro Trp Pro Ile Tyr Asn Ala
            180                 185                 190

Val Glu Leu Gln Pro Arg Glu Phe Asp Val Ala Leu Lys Asp Leu Leu
        195                 200                 205

Gly Asn Thr Lys Trp Arg Asp Trp Asp Ser Arg Leu Ser Tyr Thr Thr
    210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
                245                 250                 255

Gly Lys Lys Pro Gly Ala Phe Gly Asn Ile Glu Arg Phe Ile Tyr Leu
            260                 265                 270

Lys Ser Ile Asn Ala Tyr Cys Ser Leu Ser Asp Ile Ala Ala Tyr His
        275                 280                 285

Ala Asp Gly Val Ile Val Gly Phe Trp Arg Asp Pro Ser Ser Gly Gly
    290                 295                 300

Ala Ile Pro Phe Asp Phe Thr Lys Phe Asp Lys Thr Lys Cys Pro Ile
305                 310                 315                 320

Gln Ala Val Ile Val Val Pro Arg Ala
                325

<210> SEQ ID NO 5
<211> LENGTH: 28
<212> TYPE: DNA
<213> ORGANISM: Artificial Sequence
<220> FEATURE:
<223> OTHER INFORMATION: p1.44 primer
<220> FEATURE:
<221> NAME/KEY: misc_feature
<222> LOCATION: (1)..(2)
<223> OTHER INFORMATION: n can be any nucleotide, preferably a

<400> SEQUENCE: 5
nnccatggca aataagccaa tgcaaccg                                          28

<210> SEQ ID NO 6
<211> LENGTH: 132
<212> TYPE: PRT
<213> ORGANISM: Artificial Sequence
<220> FEATURE:
<223> OTHER INFORMATION: Bacteriophage Qbeta 240 mutant

<400> SEQUENCE: 6

Ala Lys Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
                20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
        50                  55                  60

Gln Val Lys Ile Gln Asn Pro Thr Ala Cys Thr Ala Asn Gly Ser Cys
```

```
                65                  70                  75                  80
Asp Pro Ser Val Thr Arg Gln Lys Tyr Ala Asp Val Thr Phe Ser Phe
                        85                  90                  95

Thr Gln Tyr Ser Thr Asp Glu Glu Arg Ala Phe Val Arg Thr Glu Leu
                100                 105                 110

Ala Ala Leu Leu Ala Ser Pro Leu Leu Ile Asp Ala Ile Asp Gln Leu
        115                 120                 125

Asn Pro Ala Tyr
        130

<210> SEQ ID NO 7
<211> LENGTH: 132
<212> TYPE: PRT
<213> ORGANISM: Artificial Sequence
<220> FEATURE:
<223> OTHER INFORMATION: Bacteriophage Q-beta 243 mutant

<400> SEQUENCE: 7

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
                20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                        85                  90                  95

Thr Gln Tyr Ser Thr Asp Glu Glu Arg Ala Phe Val Arg Thr Glu Leu
                100                 105                 110

Ala Ala Leu Leu Ala Ser Pro Leu Leu Ile Asp Ala Ile Asp Gln Leu
        115                 120                 125

Asn Pro Ala Tyr
        130

<210> SEQ ID NO 8
<211> LENGTH: 132
<212> TYPE: PRT
<213> ORGANISM: Artificial Sequence
<220> FEATURE:
<223> OTHER INFORMATION: Bacteriophage Q-beta 250 mutant

<400> SEQUENCE: 8

Ala Arg Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
                20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                        85                  90                  95
```

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 9
<211> LENGTH: 132
<212> TYPE: PRT
<213> ORGANISM: Artificial Sequence
<220> FEATURE:
<223> OTHER INFORMATION: Bacteriophage Q-beta 251 mutant

<400> SEQUENCE: 9

Ala Lys Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 10
<211> LENGTH: 132
<212> TYPE: PRT
<213> ORGANISM: Artificial Sequence
<220> FEATURE:
<223> OTHER INFORMATION: Bacteriophage Q-beta 259 mutant

<400> SEQUENCE: 10

Ala Arg Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

```
Ala Ala Leu Leu Ala Ser Pro Leu Leu Ile Asp Ala Ile Asp Gln Leu
        115                 120                 125

Asn Pro Ala Tyr
    130

<210> SEQ ID NO 11
<211> LENGTH: 5
<212> TYPE: PRT
<213> ORGANISM: Artificial Sequence
<220> FEATURE:
<223> OTHER INFORMATION: linker

<400> SEQUENCE: 11

Gly Gly Lys Gly Gly
1               5

<210> SEQ ID NO 12
<211> LENGTH: 49
<212> TYPE: PRT
<213> ORGANISM: Artificial Sequence
<220> FEATURE:
<223> OTHER INFORMATION: GCN4

<400> SEQUENCE: 12

Pro Ala Ala Leu Lys Arg Ala Arg Asn Glu Ala Ala Arg Arg Ser Arg
1               5                  10                  15

Ala Arg Lys Leu Gln Arg Met Lys Gln Leu Glu Asp Lys Val Glu Glu
            20                  25                  30

Leu Leu Ser Lys Asn Tyr His Leu Glu Asn Glu Val Ala Arg Leu Lys
        35                  40                  45

Lys

<210> SEQ ID NO 13
<211> LENGTH: 128
<212> TYPE: PRT
<213> ORGANISM: Bacteriophage PP7

<400> SEQUENCE: 13

Met Ser Lys Thr Ile Val Leu Ser Val Gly Glu Ala Thr Arg Thr Leu
1               5                  10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Cys Ser Thr Ser Val Cys Gly Glu Leu Pro Lys Val Arg
65                  70                  75                  80

Tyr Thr Gln Val Trp Ser His Asp Val Thr Ile Val Ala Asn Ser Thr
                85                  90                  95

Glu Ala Ser Arg Lys Ser Leu Tyr Asp Leu Thr Lys Ser Leu Val Ala
            100                 105                 110

Thr Ser Gln Val Glu Asp Leu Val Val Asn Leu Val Pro Leu Gly Arg
        115                 120                 125

<210> SEQ ID NO 14
<211> LENGTH: 131
<212> TYPE: PRT
```

<213> ORGANISM: Bacteriophage AP205

<400> SEQUENCE: 14

```
Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130
```

<210> SEQ ID NO 15
<211> LENGTH: 3635
<212> TYPE: DNA
<213> ORGANISM: Artificial Sequence
<220> FEATURE:
<223> OTHER INFORMATION: Plasmid, pAP283-58, encoding RNA phage AP205 coat protein

<400> SEQUENCE: 15

```
cgagctcgcc cctggcttat cgaaattaat acgactcact atagggagac cggaattcga      60
gctcgcccgg ggatcctcta gaattttctg cgcacccatc ccgggtggcg cccaaagtga     120
ggaaaatcac atggcaaata gccaatgcaa ccgatcaca tctacagcaa ataaaattgt      180
gtggtcggat ccaactcgtt tatcaactac attttcagca agtctgttac gccaacgtgt     240
taaagttggt atagccgaac tgaataatgt ttcaggtcaa tatgtatctg tttataagcg     300
tcctgcacct aaaccggaag gttgtgcaga tgcctgtgtc attatgccga tgaaaaacca     360
atccattcgc acagtgattt cagggtcagc gaaaacttg ctaccttaa aagcagaatg       420
ggaaactcac aaacgtaacg ttgacacact cttcgcgagc ggcaacgccg gtttgggttt     480
ccttgaccct actgcggcta tcgtatcgtc tgatactact gcttaagctt gtattctata     540
gtgtcaccta atcgtatgt gtatgataca taaggttatg tattaattgt agccgcgttc      600
taacgacaat atgtacaagc ctaattgtgt agcatctggc ttactgaagc agaccctatc     660
atctctctcg taaactgccg tcagagtcgg tttggttgga cgaaccttct gagtttctgg     720
taacgccgtt ccgcaccccg gaaatggtca ccgaaccaat cagcagggtc atcgctagcc     780
agatcctcta cgccggacgc atcgtggccg gcatcaccgg cgccacaggt gcggttgctg     840
gcgcctatat cgccgacatc accgatgggg aagatcgggc tcgccacttc gggctcatga     900
gcgcttgttt cggcgtgggt atggtggcag gccccgtggc cggggactg ttgggcgcca      960
tctccttgca tgcaccattc cttgcggcgg cggtgctcaa cggcctcaac ctactactgg    1020
gctgcttcct aatgcaggag tcgcataagg gagagcgtcg atatggtgca ctctcagtac    1080
```

```
aatctgctct gatgccgcat agttaagcca actccgctat cgctacgtga ctgggtcatg    1140
gctgcgcccc gacacccgcc aacacccgct gacgcgcccc gacgggcttg tctgctcccg    1200
gcatccgctt acagacaagc tgtgaccgtc tccgggagct gcatgtgtca gaggttttca    1260
ccgtcatcac cgaaacgcgc gaggcagctt gaagacgaaa gggcctcgtg atacgcctat    1320
ttttataggt taatgtcatg ataataatgg tttcttagac gtcaggtggc acttttcggg    1380
gaaatgtgcg cggaacccct atttgtttat ttttctaaat acattcaaat atgtatccgc    1440
tcatgagaca ataaccctga taaatgcttc aataatattg aaaaggaag agtatgagta    1500 ttcaacattt ccgtgtcgcc cttattccct tttttgcggc attttgcctt cctgtttttg    1560
ctcacccaga aacgctggtg aaagtaaaag atgctgaaga tcagttgggt gcacgagtgg    1620
gttacatcga actggatctc aacagcggta agatccttga gttttcgc cccgaagaac     1680 gttttccaat gatgagcact tttaaagttc tgctatgtgg cgcggtatta tcccgtattg    1740
acgccgggca agagcaactc ggtcgccgca tacactattc tcagaatgac ttggttgagt    1800
actcaccagt cacagaaaag catcttacgg atggcatgac agtaagagaa ttatgcagtg    1860
ctgccataac catgagtgat aacactgcgg ccaacttact tctgacaacg atcggaggac    1920
cgaaggagct aaccgctttt ttgcacaaca tgggggatca tgtaactcgc cttgatcgtt    1980
gggaaccgga gctgaatgaa gccataccaa acgacgagcg tgacaccacg atgcctgtag    2040
caatggcaac aacgttgcgc aaactattaa ctggcgaact acttactcta gcttcccggc    2100
aacaattaat agactggatg gaggcggata aagttgcagg accacttctg cgctcggccc    2160
ttccggctgg ctggtttatt gctgataaat ctggagccgg tgagcgtggg tctcgcggta    2220
tcattgcagc actggggcca gatggtaagc cctcccgtat cgtagttatc tacacgacgg    2280
ggagtcaggc aactatggat gaacgaaata gacagatcgc tgagataggt gcctcactga    2340
ttaagcattg gtaactgtca gaccaagttt actcatatat actttagatt gatttaaaac    2400 ttcatttta atttaaaagg atctaggtga agatcctttt tgataatctc atgaccaaaa    2460
tcccttaacg tgagttttcg ttccactgag cgtcagaccc cgtagaaaag atcaaaggat    2520
cttcttgaga tccttttttt ctgcgcgtaa tctgctgctt gcaaacaaaa aaaccaccgc    2580
taccagcggt ggtttgtttg ccggatcaag agctaccaac tcttttccg aaggtaactg     2640 gcttcagcag agcgcagata ccaaatactg tccttctagt gtagccgtag ttaggccacc    2700
acttcaagaa ctctgtagca ccgcctacat acctcgctct gctaatcctg ttaccagtgg    2760
ctgctgccag tggcgataag tcgtgtctta ccgggttgga ctcaagacga tagttaccgg    2820
ataaggcgca gcggtcgggc tgaacggggg gttcgtgcac acagcccagc ttggagcgaa    2880
cgacctacac cgaactgaga tacctacagc gcgagcattg agaaagcgcc acgcttcccg    2940
aagggagaaa ggcggacagg tatccggtaa gcggcagggt cggaacagga gagcgcacga    3000
gggagcttcc aggggggaaac gcctggtatc tttatagtcc tgtcgggttt cgccacctct    3060
gacttgagcg tcgatttttg tgatgctcgt caggggggcg gagcctatgg aaaaacgcca    3120
gcaacgcggc cttttacgg ttcctggcct tttgctggcc ttttgctcac atgttctttc      3180
ctgcgttatc ccctgattct gtggataacc gtattaccgc ctttgagtga gctgataccg    3240
ctcgccgcag ccgaacgacc gagcgcagcg agtcagtgag cgaggaagcg gaagagcgcc    3300
caatacgcaa accgcctctc cccgcgcgtt ggccgattca ttaatgcagc tgtggtgtca    3360
tggtcggtga tcgccagggt gccgacgcgc atctcgactg catggtgcac caatgcttct    3420
ggcgtcaggc agccatcgga agctgtggta tggccgtgca ggtcgtaaat cactgcataa    3480
```

```
ttcgtgtcgc tcaaggcgca ctcccgttct ggataatgtt ttttgcgccg acatcataac    3540
ggttctggca aatattctga aatgagctgt tgacaattaa tcatcgaact agttaactag    3600
tacgcaagtt cacgtaaaaa gggtatcgcg gaatt                               3635
```

```
<210> SEQ ID NO 16
<211> LENGTH: 57
<212> TYPE: DNA
<213> ORGANISM: Artificial Sequence
<220> FEATURE:
<223> OTHER INFORMATION: putative AP205 ribosomal binding site of
      plasmid pAP283-58

<400> SEQUENCE: 16
```

```
tctagaattt tctgcgcacc catcccgggt ggcgcccaaa gtgaggaaaa tcacatg       57
```

```
<210> SEQ ID NO 17
<211> LENGTH: 35
<212> TYPE: DNA
<213> ORGANISM: Artificial Sequence
<220> FEATURE:
<223> OTHER INFORMATION: Shine Delagarno sequence of vector pQb185

<400> SEQUENCE: 17
```

```
tctagattaa cccaacgcgt aggagtcagg ccatg                               35
```

```
<210> SEQ ID NO 18
<211> LENGTH: 131
<212> TYPE: PRT
<213> ORGANISM: Artificial Sequence
<220> FEATURE:
<223> OTHER INFORMATION: Bacteriophage AP205 mutant

<400> SEQUENCE: 18
```

```
Met Ala Asn Lys Thr Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130
```

```
<210> SEQ ID NO 19
<211> LENGTH: 3613
<212> TYPE: DNA
<213> ORGANISM: Artificial Sequence
<220> FEATURE:
<223> OTHER INFORMATION: Plasmid, pAP281-32, encoding RNA phage AP205
      coat protein

<400> SEQUENCE: 19
```

-continued

```
cgagctcgcc cctggcttat cgaaattaat acgactcact atagggagac cggaattcga      60
gctcgcccgg ggatcctcta gattaaccca acgcgtagga gtcaggccat ggcaaataag     120
acaatgcaac cgatcacatc tacagcaaat aaaattgtgt ggtcggatcc aactcgttta     180
tcaactacat tttcagcaag tctgttacgc aacgtgtta aagttggtat agccgaactg     240
aataatgttt caggtcaata tgtatctgtt tataagcgtc ctgcacctaa accgaaggt     300
tgtgcagatg cctgtgtcat tatgccgaat gaaaaccaat ccattcgcac agtgatttca     360
gggtcagccg aaaacttggc taccttaaaa gcagaatggg aaactcacaa acgtaacgtt     420
gacacactct tcgcgagcgg caacgccggt ttgggtttcc ttgaccctac tgcggctatc     480
gtatcgtctg atactactgc ttaagcttgt attctatagt gtcacctaaa tcgtatgtgt     540
atgatacata aggttatgta ttaattgtag ccgcgttcta acgacaatat gtacaagcct     600
aattgtgtag catctggctt actgaagcag accctatcat ctctctcgta aactgccgtc     660
agagtcggtt tggttggacg aaccttctga gtttctggta acgccgttcc gcaccccgga     720
aatggtcacc gaaccaatca gcagggtcat cgctagccag atcctctacg ccggacgcat     780
cgtggccggc atcaccggcg ccacaggtgc ggttgctggc gcctatatcg ccgacatcac     840
cgatggggaa gatcgggctc gccacttcgg gctcatgagc gcttgtttcg gcgtgggtat     900
ggtggcaggc cccgtggccg ggggactgtt gggcgccatc tccttgcatg caccattcct     960
tgcggcggcg gtgctcaacg gcctcaacct actactgggc tgcttcctaa tgcaggagtc    1020
gcataaggga gagcgtcgat atggtgcact ctcagtacaa tctgctctga tgccgcatag    1080
ttaagccaac tccgctatcg ctacgtgact gggtcatggc tgcgccccga cacccgccaa    1140
cacccgctga cgcgccctga cgggcttgtc tgctcccggc atccgcttac agacaagctg    1200
tgaccgtctc cgggagctgc atgtgtcaga ggttttcacc gtcatcaccg aaacgcgcga    1260
ggcagcttga agacgaaagg gcctcgtgat acgcctattt ttataggtta atgtcatgat    1320
aataatggtt tcttagacgt caggtggcac ttttcgggga aatgtgcgcg gaacccctat    1380
ttgtttattt ttctaaatac attcaaatat gtatccgctc atgagacaat aaccctgata    1440
aatgcttcaa taatattgaa aaaggaagag tatgagtatt caacatttcc gtgtcgccct    1500
tattccctttt tttgcggcat tttgccttcc tgttttgct cacccagaaa cgctggtgaa    1560
agtaaaagat gctgaagatc agttgggtgc acgagtgggt tacatcgaac tggatctcaa    1620
cagcggtaag atccttgaga gttttcgccc cgaagaacgt tttccaatga tgagcacttt    1680
taaagttctg ctatgtggcg cggtattatc ccgtattgac gccgggcaag agcaactcgg    1740
tcgccgcata cactattctc agaatgactt ggttgagtac tcaccagtca cagaaaagca    1800
tcttacggat ggcatgacag taagagaatt atgcagtgct gccataacca tgagtgataa    1860
cactgcggcc aacttacttc tgacaacgat cggaggaccg aaggagctaa ccgcttttt    1920
gcacaacatg ggggatcatg taactcgcct tgatcgttgg gaaccggagc tgaatgaagc    1980
cataccaaac gacgagcgtg acaccacgat gcctgtagca atggcaacaa cgttgcgcaa    2040
actattaact ggcgaactac ttactctagc ttcccggcaa caattaatag actggatgga    2100
ggcggataaa gttgcaggac cacttctgcg ctcggccctt ccggctggct ggtttattgc    2160
tgataaatct ggagccggtg agcgtgggtc tcgcggtatc attgcagcac tggggccaga    2220
tggtaagccc tcccgtatcg tagttatcta cacgacgggg agtcaggcaa ctatggatga    2280
acgaaataga cagatcgctg agataggtgc ctcactgatt aagcattggt aactgtcaga    2340
```

-continued

```
ccaagtttac tcatatatac tttagattga tttaaaactt catttttaat ttaaaaggat    2400
ctaggtgaag atccttttg ataatctcat gaccaaaatc ccttaacgtg agttttcgtt    2460
ccactgagcg tcagacccccg tagaaaagat caaaggatct tcttgagatc ctttttttct    2520
gcgcgtaatc tgctgcttgc aaacaaaaaa accaccgcta ccagcggtgg tttgtttgcc    2580
ggatcaagag ctaccaactc tttttccgaa ggtaactggc ttcagcagag cgcagatacc    2640
aaatactgtc cttctagtgt agccgtagtt aggccaccac ttcaagaact ctgtagcacc    2700
gcctacatac ctcgctctgc taatcctgtt accagtggct gctgccagtg gcgataagtc    2760
gtgtcttacc gggttggact caagacgata gttaccggat aaggcgcagc ggtcgggctg    2820
aacggggggt tcgtgcacac agcccagctt ggagcgaacg acctacaccg aactgagata    2880
cctacagcgc gagcattgag aaagcgccac gcttcccgaa gggagaaagg cggacaggta    2940
tccggtaagc ggcagggtcg gaacaggaga gcgcacgagg gagcttccag ggggaaacgc    3000
ctggtatctt tatagtcctg tcgggtttcg ccacctctga cttgagcgtc gatttttgtg    3060
atgctcgtca ggggggcgga gcctatggaa aaacgccagc aacgcggcct ttttacggtt    3120
cctggccttt tgctggcctt tgctcacat gttctttcct gcgttatccc ctgattctgt    3180
ggataaccgt attaccgcct ttgagtgagc tgataccgct cgccgcagcc gaacgaccga    3240
gcgcagcgag tcagtgagcg aggaagcgga agagcgccca atacgcaaac cgcctctccc    3300
cgcgcgttgg ccgattcatt aatgcagctg tggtgtcatg gtcggtgatc gccagggtgc    3360
cgacgcgcat ctcgactgca tggtgcacca atgcttctgg cgtcaggcag ccatcggaag    3420
ctgtggtatg gccgtgcagg tcgtaaatca ctgcataatt cgtgtcgctc aaggcgcact    3480
cccgttctgg ataatgtttt ttgcgccgac atcataacgg ttctggcaaa tattctgaaa    3540
tgagctgttg acaattaatc atcgaactag ttaactagta cgcaagttca cgtaaaaagg    3600
gtatcgcgga att                                                       3613
```

<210> SEQ ID NO 20
<211> LENGTH: 30
<212> TYPE: DNA
<213> ORGANISM: Artificial Sequence
<220> FEATURE:
<223> OTHER INFORMATION: p1.45 primer
<220> FEATURE:
<221> NAME/KEY: misc_feature
<222> LOCATION: (1)..(2)
<223> OTHER INFORMATION: n can be any nucleotide, preferably a

<400> SEQUENCE: 20
nntctagaat tttctgcgca cccatcccgg                                      30

<210> SEQ ID NO 21
<211> LENGTH: 31
<212> TYPE: DNA
<213> ORGANISM: Artificial Sequence
<220> FEATURE:
<223> OTHER INFORMATION: p1.46 primer
<220> FEATURE:
<221> NAME/KEY: misc_feature
<222> LOCATION: (1)..(2)
<223> OTHER INFORMATION: n can be any nucleotide, preferably a

<400> SEQUENCE: 21
nnaagcttaa gcagtagtat cagacgatac g                                    31

<210> SEQ ID NO 22
<211> LENGTH: 43

-continued

```
<212> TYPE: DNA
<213> ORGANISM: Artificial Sequence
<220> FEATURE:
<223> OTHER INFORMATION: p1.47 primer

<400> SEQUENCE: 22
gagtgatcca actcgtttat caactacatt ttcagcaagt ctg          43

<210> SEQ ID NO 23
<211> LENGTH: 43
<212> TYPE: DNA
<213> ORGANISM: Artificial Sequence
<220> FEATURE:
<223> OTHER INFORMATION: p1.48 primer

<400> SEQUENCE: 23
cagacttgct gaaaatgtag ttgataaacg agttggatca ctc          43

<210> SEQ ID NO 24
<211> LENGTH: 129
<212> TYPE: PRT
<213> ORGANISM: Bacteriophage R17

<400> SEQUENCE: 24
```

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
                20                  25                  30

Ile Ser Ser Asn Ser Arg Ser Gln Ala Tyr Lys Val Thr Cys Ser Val
            35                  40                  45

Arg Gln Ser Ser Ala Gln Asn Arg Lys Tyr Thr Ile Lys Val Glu Val
        50                  55                  60

Pro Lys Val Ala Thr Gln Thr Val Gly Gly Val Glu Leu Pro Val Ala
65                  70                  75                  80

Ala Trp Arg Ser Tyr Leu Asn Met Glu Leu Thr Ile Pro Ile Phe Ala
                85                  90                  95

Thr Asn Ser Asp Cys Glu Leu Ile Val Lys Ala Met Gln Gly Leu Leu
                100                 105                 110

Lys Asp Gly Asn Pro Ile Pro Ser Ala Ile Ala Ala Asn Ser Gly Ile
            115                 120                 125

Tyr

```
<210> SEQ ID NO 25
<211> LENGTH: 130
<212> TYPE: PRT
<213> ORGANISM: Bacteriophage fr

<400> SEQUENCE: 25
```

Met Ala Ser Asn Phe Glu Glu Phe Val Leu Val Asp Asn Gly Gly Thr
1               5                   10                  15

Gly Asp Val Lys Val Ala Pro Ser Asn Phe Ala Asn Gly Val Ala Glu
                20                  25                  30

Trp Ile Ser Ser Asn Ser Arg Ser Gln Ala Tyr Lys Val Thr Cys Ser
            35                  40                  45

Val Arg Gln Ser Ser Ala Asn Asn Arg Lys Tyr Thr Val Lys Val Glu
        50                  55                  60

Val Pro Lys Val Ala Thr Gln Val Gln Gly Gly Val Glu Leu Pro Val
65                  70                  75                  80

Ala Ala Trp Arg Ser Tyr Met Asn Met Glu Leu Thr Ile Pro Val Phe

```
                    85                  90                  95
Ala Thr Asn Asp Asp Cys Ala Leu Ile Val Lys Ala Leu Gln Gly Thr
            100                 105                 110

Phe Lys Thr Gly Asn Pro Ile Ala Thr Ala Ile Ala Ala Asn Ser Gly
        115                 120                 125

Ile Tyr
    130

<210> SEQ ID NO 26
<211> LENGTH: 130
<212> TYPE: PRT
<213> ORGANISM: Bacteriophage GA

<400> SEQUENCE: 26

Met Ala Thr Leu Arg Ser Phe Val Leu Val Asp Asn Gly Gly Thr Gly
1               5                   10                  15

Asn Val Thr Val Val Pro Val Ser Asn Ala Asn Gly Val Ala Glu Trp
            20                  25                  30

Leu Ser Asn Asn Ser Arg Ser Gln Ala Tyr Arg Val Thr Ala Ser Tyr
        35                  40                  45

Arg Ala Ser Gly Ala Asp Lys Arg Lys Tyr Ala Ile Lys Leu Glu Val
    50                  55                  60

Pro Lys Ile Val Thr Gln Val Val Asn Gly Val Glu Leu Pro Gly Ser
65                  70                  75                  80

Ala Trp Lys Ala Tyr Ala Ser Ile Asp Leu Thr Ile Pro Ile Phe Ala
                85                  90                  95

Ala Thr Asp Asp Val Thr Val Ile Ser Lys Ser Leu Ala Gly Leu Phe
            100                 105                 110

Lys Val Gly Asn Pro Ile Ala Glu Ala Ile Ser Ser Gln Ser Gly Phe
        115                 120                 125

Tyr Ala
    130

<210> SEQ ID NO 27
<211> LENGTH: 132
<212> TYPE: PRT
<213> ORGANISM: Bacteriophage SP

<400> SEQUENCE: 27

Met Ala Lys Leu Asn Gln Val Thr Leu Ser Lys Ile Gly Lys Asn Gly
1               5                   10                  15

Asp Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Phe Lys
    50                  55                  60

Val Gln Ile Lys Leu Gln Asn Pro Thr Ala Cys Thr Arg Asp Ala Cys
65                  70                  75                  80

Asp Pro Ser Val Thr Arg Ser Ala Phe Ala Asp Val Thr Leu Ser Phe
                85                  90                  95

Thr Ser Tyr Ser Thr Asp Glu Glu Arg Ala Leu Ile Arg Thr Glu Leu
            100                 105                 110

Ala Ala Leu Leu Ala Asp Pro Leu Ile Val Asp Ala Ile Asp Asn Leu
        115                 120                 125

Asn Pro Ala Tyr
```

<210> SEQ ID NO 28
<211> LENGTH: 329
<212> TYPE: PRT
<213> ORGANISM: Bacteriophage SP

<400> SEQUENCE: 28

Ala Lys Leu Asn Gln Val Thr Leu Ser Lys Ile Gly Lys Asn Gly Asp
1               5                   10                  15

Gln Thr Leu Thr Leu Thr Pro Arg Gly Val Asn Pro Thr Asn Gly Val
            20                  25                  30

Ala Ser Leu Ser Glu Ala Gly Ala Val Pro Ala Leu Glu Lys Arg Val
        35                  40                  45

Thr Val Ser Val Ala Gln Pro Ser Arg Asn Arg Lys Asn Phe Lys Val
50                  55                  60

Gln Ile Lys Leu Gln Asn Pro Thr Ala Cys Thr Arg Asp Ala Cys Asp
65                  70                  75                  80

Pro Ser Val Thr Arg Ser Ala Phe Ala Asp Val Thr Leu Ser Phe Thr
                85                  90                  95

Ser Tyr Ser Thr Asp Glu Glu Arg Ala Leu Ile Arg Thr Glu Leu Ala
            100                 105                 110

Ala Leu Leu Ala Asp Pro Leu Ile Val Asp Ala Ile Asp Asn Leu Asn
        115                 120                 125

Pro Ala Tyr Trp Ala Ala Leu Leu Val Ala Ser Ser Gly Gly Gly Asp
130                 135                 140

Asn Pro Ser Asp Pro Asp Val Pro Val Val Pro Asp Val Lys Pro Pro
145                 150                 155                 160

Asp Gly Thr Gly Arg Tyr Lys Cys Pro Phe Ala Cys Tyr Arg Leu Gly
                165                 170                 175

Ser Ile Tyr Glu Val Gly Lys Glu Gly Ser Pro Asp Ile Tyr Glu Arg
            180                 185                 190

Gly Asp Glu Val Ser Val Thr Phe Asp Tyr Ala Leu Glu Asp Phe Leu
        195                 200                 205

Gly Asn Thr Asn Trp Arg Asn Trp Asp Gln Arg Leu Ser Asp Tyr Asp
210                 215                 220

Ile Ala Asn Arg Arg Cys Arg Gly Asn Gly Tyr Ile Asp Leu Asp Asp
225                 230                 235                 240

Ala Thr Ala Met Gln Ser Asp Asp Phe Val Leu Ser Gly Arg Tyr Gly
                245                 250                 255

Val Arg Lys Val Lys Phe Pro Gly Ala Phe Gly Ser Ile Lys Tyr Leu
            260                 265                 270

Leu Asn Ile Gln Gly Asp Ala Trp Leu Asp Leu Ser Glu Val Thr Ala
        275                 280                 285

Tyr Arg Ser Tyr Gly Met Val Ile Gly Phe Trp Thr Asp Ser Lys Ser
290                 295                 300

Pro Gln Leu Pro Thr Asp Phe Thr Gln Phe Asn Ser Ala Asn Cys Pro
305                 310                 315                 320

Val Gln Thr Val Ile Ile Ile Pro Ser
                325

<210> SEQ ID NO 29
<211> LENGTH: 130
<212> TYPE: PRT
<213> ORGANISM: Bacteriophage MS2

<400> SEQUENCE: 29

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 30
<211> LENGTH: 133
<212> TYPE: PRT
<213> ORGANISM: Bacteriophage M11

<400> SEQUENCE: 30

Met Ala Lys Leu Gln Ala Ile Thr Leu Ser Gly Ile Gly Lys Lys Gly
1               5                   10                  15

Asp Val Thr Leu Asp Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ser Asp Val Thr Phe Ser
                85                  90                  95

Phe Thr Gln Tyr Ser Thr Val Glu Glu Arg Ala Leu Val Arg Thr Glu
            100                 105                 110

Leu Gln Ala Leu Leu Ala Asp Pro Met Leu Val Asn Ala Ile Asp Asn
        115                 120                 125

Leu Asn Pro Ala Tyr
    130

<210> SEQ ID NO 31
<211> LENGTH: 133
<212> TYPE: PRT
<213> ORGANISM: Bacteriophage MX1

<400> SEQUENCE: 31

Met Ala Lys Leu Gln Ala Ile Thr Leu Ser Gly Ile Gly Lys Asn Gly
1               5                   10                  15

Asp Val Thr Leu Asn Leu Asn Pro Arg Gly Val Asn Pro Thr Asn Gly
            20                  25                  30

Val Ala Ala Leu Ser Glu Ala Gly Ala Val Pro Ala Leu Glu Lys Arg

```
            35                  40                  45
Val Thr Ile Ser Val Ser Gln Pro Ser Arg Asn Arg Lys Asn Tyr Lys
     50                  55                  60

Val Gln Val Lys Ile Gln Asn Pro Thr Ser Cys Thr Ala Ser Gly Thr
 65                  70                  75                  80

Cys Asp Pro Ser Val Thr Arg Ser Ala Tyr Ala Asp Val Thr Phe Ser
                 85                  90                  95

Phe Thr Gln Tyr Ser Thr Asp Glu Glu Arg Ala Leu Val Arg Thr Glu
             100                 105                 110

Leu Lys Ala Leu Leu Ala Asp Pro Met Leu Ile Asp Ala Ile Asp Asn
         115                 120                 125

Leu Asn Pro Ala Tyr
         130

<210> SEQ ID NO 32
<211> LENGTH: 330
<212> TYPE: PRT
<213> ORGANISM: Bacteriophage NL95

<400> SEQUENCE: 32

Met Ala Lys Leu Asn Lys Val Thr Leu Thr Gly Ile Gly Lys Ala Gly
 1               5                  10                  15

Asn Gln Thr Leu Thr Leu Thr Pro Arg Gly Val Asn Pro Thr Asn Gly
             20                  25                  30

Val Ala Ser Leu Ser Glu Ala Gly Ala Val Pro Ala Leu Glu Lys Arg
         35                  40                  45

Val Thr Val Ser Val Ala Gln Pro Ser Arg Asn Arg Lys Asn Tyr Lys
     50                  55                  60

Val Gln Ile Lys Leu Gln Asn Pro Thr Ala Cys Thr Lys Asp Ala Cys
 65                  70                  75                  80

Asp Pro Ser Val Thr Arg Ser Gly Ser Arg Asp Val Thr Leu Ser Phe
                 85                  90                  95

Thr Ser Tyr Ser Thr Glu Arg Glu Arg Ala Leu Ile Arg Thr Glu Leu
             100                 105                 110

Ala Ala Leu Leu Lys Asp Asp Leu Ile Val Asp Ala Ile Asp Asn Leu
         115                 120                 125

Asn Pro Ala Tyr Trp Ala Leu Leu Ala Ala Ser Pro Gly Gly Gly
         130                 135                 140

Asn Asn Pro Tyr Pro Gly Val Pro Asp Ser Pro Asn Val Lys Pro Pro
145                 150                 155                 160

Gly Gly Thr Gly Thr Tyr Arg Cys Pro Phe Ala Cys Tyr Arg Arg Gly
                 165                 170                 175

Glu Leu Ile Thr Glu Ala Lys Asp Gly Ala Cys Ala Leu Tyr Ala Cys
             180                 185                 190

Gly Ser Glu Ala Leu Val Glu Phe Glu Tyr Ala Leu Glu Asp Phe Leu
         195                 200                 205

Gly Asn Glu Phe Trp Arg Asn Trp Asp Gly Arg Leu Ser Lys Tyr Asp
         210                 215                 220

Ile Glu Thr His Arg Arg Cys Arg Gly Asn Gly Tyr Val Asp Leu Asp
225                 230                 235                 240

Ala Ser Val Met Gln Ser Asp Glu Tyr Val Leu Ser Gly Ala Tyr Asp
                 245                 250                 255

Val Val Lys Met Gln Pro Pro Gly Thr Phe Asp Ser Pro Arg Tyr Tyr
             260                 265                 270
```

-continued

```
Leu His Leu Met Asp Gly Ile Tyr Val Asp Leu Ala Glu Val Thr Ala
        275                 280                 285

Tyr Arg Ser Tyr Gly Met Val Ile Gly Phe Trp Thr Asp Ser Lys Ser
        290                 295                 300

Pro Gln Leu Pro Thr Asp Phe Thr Arg Phe Asn Arg His Asn Cys Pro
305                 310                 315                 320

Val Gln Thr Val Ile Val Ile Pro Ser Leu
                325                 330

<210> SEQ ID NO 33
<211> LENGTH: 129
<212> TYPE: PRT
<213> ORGANISM: Bacteriophage f2

<400> SEQUENCE: 33

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
                20                  25                  30

Ile Ser Ser Asn Ser Arg Ser Gln Ala Tyr Lys Val Thr Cys Ser Val
            35                  40                  45

Arg Gln Ser Ser Ala Gln Asn Arg Lys Tyr Thr Ile Lys Val Glu Val
        50                  55                  60

Pro Lys Val Ala Thr Gln Thr Val Gly Gly Val Glu Leu Pro Val Ala
65                  70                  75                  80

Ala Trp Arg Ser Tyr Leu Asn Leu Glu Leu Thr Ile Pro Ile Phe Ala
                85                  90                  95

Thr Asn Ser Asp Cys Glu Leu Ile Val Lys Ala Met Gln Gly Leu Leu
                100                 105                 110

Lys Asp Gly Asn Pro Ile Pro Ser Ala Ile Ala Ala Asn Ser Gly Ile
            115                 120                 125

Tyr
```